United States Patent
Sydora

(10) Patent No.: US 8,450,511 B1
(45) Date of Patent: May 28, 2013

(54) ANHYDROUS CHROMIUM(III) HALIDE COMPLEX PREPARATION

(75) Inventor: Orson L Sydora, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 7 days.

(21) Appl. No.: 13/323,265

(22) Filed: Dec. 12, 2011

(51) Int. Cl.
*C07F 11/00* (2006.01)

(52) U.S. Cl.
USPC ............................................ 556/57; 549/206

(58) Field of Classification Search
USPC ............................................ 556/57; 549/206
See application file for complete search history.

(56) References Cited

PUBLICATIONS

"Software Estimates Chemical, Physical Properties", Feb. 4, 1985, C&EN, p. 27.
Herwig, W., et al., "Chromium Trichloride Tetrahydrofuranate", Sep. 1958, pp. 1404-1405, vol. 23.
Jones, Peter J., et al., "Synthesis and Properties of Tetrahydrofuran Complexes of Chromium (III), [Cr(THF)$_3$X$_3$] (X = Cl, Br, I), [Cr(THF)$_2$X$_4$]·(X = Cl, Br, I, NCS), and "[Cr(THF)$_6$](BF$_4$)$_3$'", Inorg. Chem., 1983, pp. 2642-2644, vol. 22, American Chemical Society.
Kern, R.J., "Tetrahydrofuran Complexes of Transition Metal Chlorides", J Inorg. Nucl. Chem., 1962, pp. 1105-1109, vol. 24, Pergamon Press Ltd., England.
Pray, Alfred R., "Anhydrous Metal Chlorides", Inorganic Synthesis, 1957, pp. 153-156, vol. 5, McGraw-Hill Book Company, Inc.
So, Jeung-Ho, et al., "A Convenient Synthesis of Solvated and Unsolvated Anhydrous Metal Chlorides via Dehydration of Metal Chloride Hydrates with Trimethylchlorosilane", Inorg. Chem., 1990, pp. 1592-1593, vol. 29, American Chemical Society.
Tyree Jr., S.Y., "Anhydrous Metal Halides", Inorganic Syntheses, 1953, pp. 104-111, vol. 4, McGraw-Hill Book Company, Inc.

*Primary Examiner* — Porfirio Nazario Gonzalez
(74) *Attorney, Agent, or Firm* — Conley Rose, P.C.; Rodney B. Carroll; Lynda S. Jolly

(57) ABSTRACT

This disclosure provides a process for preparing an anhydrous chromium(III) halide complex, comprising contacting a chromium(III) halide hydrate, a water absorption agent, and a coordinating solvent, L, and forming a chromium(III) halide complex having the formula CrX$_3$.mL, wherein X is a halide and m is the number of moles of L per mole of chromium. This process is exemplified in the preparation of the substantially anhydrous or anhydrous CrCl$_3$(THF)$_3$, the process comprising contacting CrCl$_3$.6H$_2$O, tetrahydrofuran, and 3 Å, 4 Å, 5 Å, 10×, or 13× molecular sieves; forming CrCl$_3$(THF)$_3$; and isolating the CrCl$_3$(THF)$_3$ having a water content of less than or equal to 100 ppm.

20 Claims, 2 Drawing Sheets

ANHYDROUS CHROMIUM(III) HALIDE COMPLEX PREPARATION

TECHNICAL FIELD OF THE INVENTION

This disclosure relates to synthetic methods for preparing substantially anhydrous metal halide complexes, such as substantially anhydrous first-row transition metal halide complexes, and in particular, substantially anhydrous chromium halide complexes, including chromium(III) halide complexes.

BACKGROUND OF THE INVENTION

Substantially anhydrous and/or anhydrous chromium(III) halide complexes (e.g., $CrCl_3(THF)_3$) are useful materials for producing coordination and organometallic chromium compounds. Substantially anhydrous and/or anhydrous chromium complexes of this type generally are expensive to produce and few convenient synthetic techniques are available. For example, current methods can require either the separate formation of the substantially anhydrous and/or anhydrous $CrCl_3$ from $CrCl_3$ hydrate, or employ dehydrating agents that produce acid as a result of their dehydrating action. Such methods typically require heating and/or vacuum, and the presence of acid. Chromium(III) halide complexes produced via these methods can contain impurities or by-products which can be detrimental to preparing coordination and organometallic chromium compounds and/or catalyst systems containing the prepared coordination and organometallic chromium compounds. Therefore, more convenient and simpler methods to form substantially anhydrous and/or anhydrous chromium(III) halide complexes such as $CrCl_3(THF)_3$ are needed. Moreover, methods to form substantially anhydrous and/or anhydrous chromium(III) halide complexes such as $CrCl_3(THF)_3$ that do not require substantial heating under vacuum or produce acid as a result of the dehydration process would be desirable.

SUMMARY OF THE INVENTION

Among other things, this disclosure provides a process for preparing chromium(III) halide complexes, the process comprising: contacting 1) a chromium(III) halide hydrate, 2) a water absorption agent, and 3) a coordinating compound, L, to form a chromium(III) halide complex of the formula $CrX_3.mL$. Generally, X represents a halide, L represents the coordinating compound, and m is the number of moles of L per mole of chromium. In any aspect or embodiment, the halide X can be F, Cl, Br, or I. In any aspect or embodiment, m can be from about 0.25 to about 10. In an aspect, the process can further comprise isolating the chromium(III) halide complex. In one aspect, the chromium(III) halide hydrate can have the formula $CrX_3(L^1)_q.nH_2O$; or alternatively, $CrX_3.H_2O$. Generally, X represents a halide, $L^1$ represents a coordinating ligand, q represents the number of coordinating ligands, and n represent the number of moles of $H_2O$ per mole of chromium. In some embodiments, the chromium(III) halide complex, $CrX_3.mL$, can be formed under conditions capable of forming $CrX_3.mL$. In some embodiments, $CrX_3.mL$ can be formed without heating and/or without applying vacuum.

In another aspect, this disclosure provides a process for preparing $CrCl_3(THF)_3$, the process comprising: contacting 1) a chromium(III) chloride hydrate, 2) a water absorption agent, and 3) tetrahydrofuran to form $CrCl_3(THF)_3$. In an aspect, the process can further comprise isolating the $CrCl_3(THF)_3$. In any aspect or embodiment, the chromium(III) halide hydrate can be $CrCl_3(THF)_2(H_2O)$; or alternatively, $CrCl_3.6H_2O$. In some embodiments, the forming of $CrCl_3(THF)_3$ can be formed under conditions capable of forming $CrCl_3(THF)_3$. In some embodiments, $CrCl_3(THF)_3$ can be formed without heating and/or without applying vacuum.

In any aspect of or embodiment, the contacting step can occur by flowing a solution comprising 1) the chromium(III) halide hydrate (e.g., a chromium(III) chloride hydrate) and 2) the coordinating compound (e.g., tetrahydrofuran) through or over a fixed bed of a solid water absorption agent. In a aspect, this disclosure provides a process for preparing a chromium (III) halide complex, the process comprising: flowing a mixture comprising 1) a chromium(III) halide hydrate (e.g., a chromium(III) chloride hydrate) and 2) a coordinating compound, L (e.g., tetrahydrofuran), through a bed comprising a solid water absorption agent to form a chromium chromium (III) halide complex having the formula $CrX_3.mL$ (e.g., $CrCl_3(THF)_3$). Generally, X represents a halide, L represents the coordinating compound, and m is the number of moles of L per mole of chromium. In any aspect or embodiment, the halide X can be F, Cl, Br, or I. In any aspect or embodiment, m can be from about 0.25 to about 10. In an aspect, the process can further comprise isolating the chromium(III) halide complex. In one aspect, the chromium(III) halide hydrate can have the formula $CrX_3(L^1)_q.nH_2O$; or alternatively, $CrX_3.nH_2O$. Generally, X represents a halide, $L^1$ represents a coordinating ligand, q represents the number of coordinating ligands, and n represents the number of moles of $H_2O$ per mole of chromium. In some embodiments, the chromium(III) halide complex, $CrX_3.mL$, can be formed under conditions capable of forming $CrX_3.mL$. In some embodiments, the chromium(III) halide hydrate to water absorption agent weight hourly space velocity ranges from 0.1 to 10.

In an embodiment, the isolated chromium(III) halide complex (e.g., $CrCl_3(THF)_3$) can have a water content of less than or equal to 100 ppm. In an embodiment, the contacting of the chromium(III) halide hydrate (e.g., $CrCl_3(THF)_2(H_2O)$ or $CrCl_3.6H_2O$), the water absorption agent (e.g., molecular sieves), and the coordinating compound (e.g., tetrahydrofuran) forms a solution comprising the chromium halide complex (e.g., $CrCl_3(THF)_3$) and the coordinating compound (e.g., tetrahydrofuran). In any aspect or embodiment of this disclosure, the formed chromium(III) halide complex (e.g., $CrCl_3(THF)_3$) can be isolated. In any aspect or embodiment, the process for the isolation of the chromium(III) halide complex (e.g., $CrCl_3(THF)_3$) can comprise: filtering the solution and any one of the following:

i) concentrating the filtered chromium halide complex/coordinating compound solution (e.g., $CrCl_3(THF)_3$/tetrahydrofuran solution);

ii) cooling the filtered chromium halide complex/coordinating compound solution (e.g., $CrCl_3(THF)_3$/tetrahydrofuran solution);

iii) contacting the filtered chromium halide complex/coordinating compound solution (e.g., $CrCl_3(THF)_3$/tetrahydrofuran solution) with a non-coordinating solvent; or iv) any combination thereof i), ii), and/or iii).

In an aspect, the water absorption agent can be a solid. In any aspect or embodiment, the water absorption agent can be an alumina, a silica gel, a silica-alumina, gypsum, montmorillonite, a molecular sieve, a zeolite, or any combination thereof. In any aspect or embodiment, the water absorption agent can be a 3 Å molecular sieve, a 4 Å molecular sieve, a 5 Å molecular sieve, a 10× molecular sieve, a 13× molecular sieve, or any combination thereof.

In an aspect, the coordinating compound can be a $C_2$-$C_{20}$ acyclic ether, a $C_3$-$C_{20}$ cyclic ether, a $C_2$-$C_{20}$ acyclic thioether, a $C_3$-$C_{20}$ cyclic thioether, a $C_2$-$C_{20}$ nitrile, a $C_1$-$C_{20}$ acyclic amine, a $C_3$-$C_{20}$ cyclic amine, a $C_3$-$C_{20}$ heterocycle, or any combination thereof. In an embodiment, the coordinating compound can be a substituted or an unsubstituted cyclic ether. In other embodiments, the coordinating compound can be tetrahydrofuran.

These and other aspects and embodiments of the process for preparing anhydrous metal halides, anhydrous first-row transition metal halides, and in particular, anhydrous halides of chromium, including anhydrous chromium(III) halide complexes such as $CrCl_3(THF)_3$ are described more fully in the Detailed Description and Claims and the further disclosure provided herein.

DETAILED DESCRIPTION OF THE INVENTION

Figure 1:
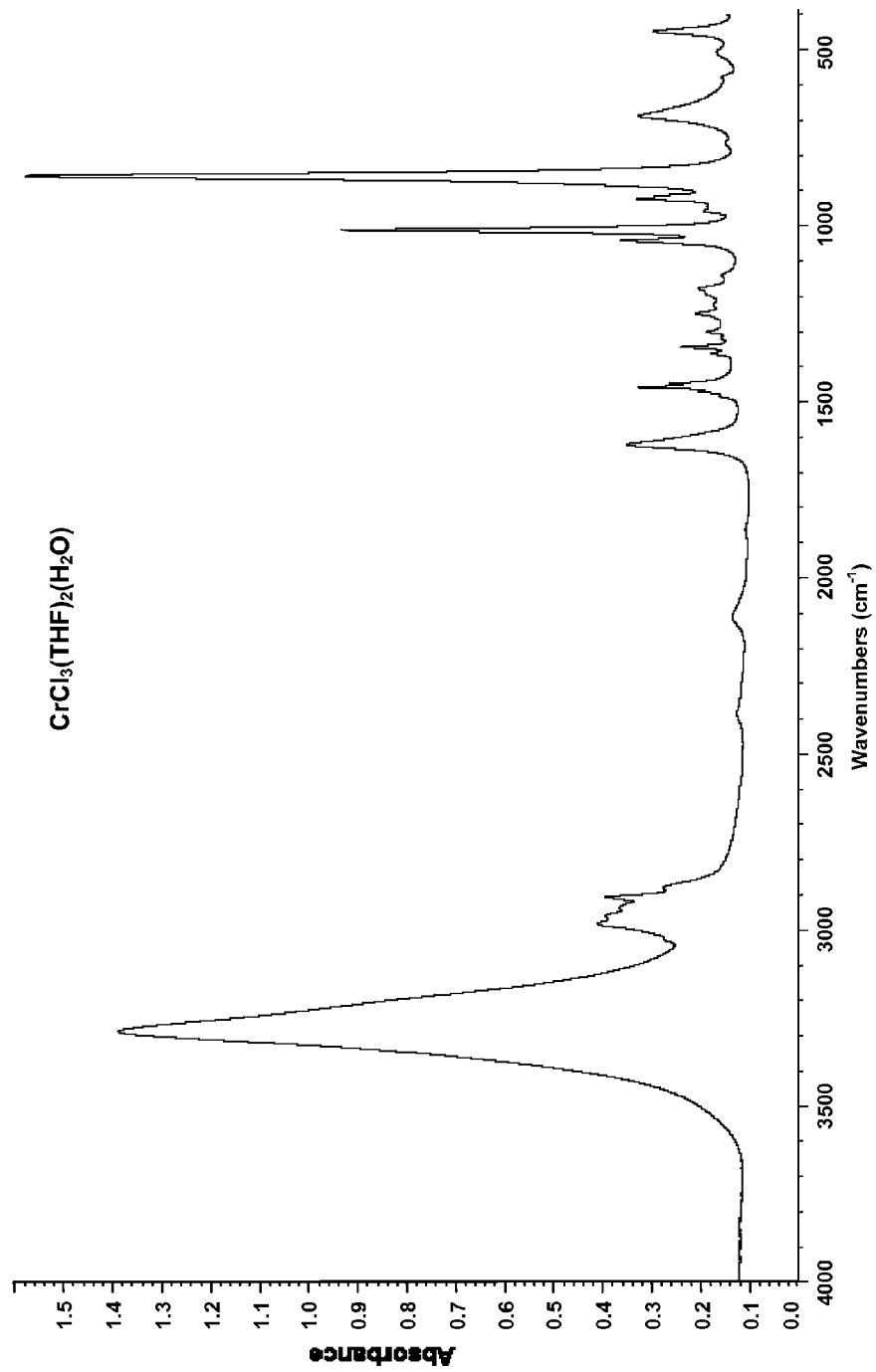
FIG. 1 provides the infrared spectrum of a $CrCl_3(THF)_2(H_2O)$ sample analyzed as an admixture with KBr pressed into a 10 mm pellet.

The selective trimerization of ethylene to 1-hexene represents a commercially significant process for producing 1-hexene. Many catalyst systems utilized in the selective trimerization of ethylene employ a chromium carboxylate as a constituent. While chromium compounds of carboxylates having low carbon numbers (e.g., chromium acetate) are readily available as well-defined and well-characterized materials, chromium compounds of carboxylates having higher carbon numbers (e.g., $C_3$ and higher carboxylates) generally are not pure compounds, contain mixtures of compounds, and/or are not well-defined. While not wishing to be bound by theory, it is believed that this feature of chromium carboxylates of higher carbon numbered carboxylates arises because the higher carbon numbered chromium carboxylates are typically produced by displacing a low carbon number carboxylate ion from a chromium carboxylate with a higher carbon numbered carboxylate in the form of a higher carbon numbered carboxylic acid. Typically, this process can require an excess quantity of the higher carbon numbered carboxylic acid in order to effectively displace the lower carbon numbered carboxylate. Removal of the excess carboxylic acid often can be difficult and/or can cause compositional changes in the chromium carboxylate composition. Additionally, an incomplete reaction can occur, which can result in a chromium carboxylate composition comprising more than one chromium carboxylate species and/or excess carboxylic acid that cannot be removed while maintaining the quality of the chromium carboxylate. Additionally, chromium carboxylates of carboxylates having a low carbon number often can be hydrates, and water must be reduced to provide a suitable chromium carboxylate compound for further use.

It has recently been discovered that improved chromium carboxylate compositions wherein the carboxylate has more than two carbon atoms can be produced by metathesis reactions of chromium halide complexes. However, the syntheses of these chromium carboxylates can be best performed using substantially anhydrous or anhydrous chromium halide complexes (e.g., $CrCl_3(THF)_3$).

The chromium(III) precursors most widely-used as a catalyst system component for selective alpha-olefin preparation are chromium(III) carboxylates using carboxylates having at least 4 carbon atoms (e.g., tris(2-ethylhexanoate) chromium (III)—sometimes referred to as $Cr(EH)_3$). However, these chromium carboxylates are mixtures of several chromium carboxylate species. A recently discovered method for preparing the chromium(III) carboxylates uses substantially anhydrous chromium(III) halide complexes or anhydrous chromium(III) halide complexes as the starting material. The recently discovered method for preparing the chromium(III) carboxylates is disclosed in co-pending U.S. patent application Ser. No. 13/323,191 filed on Dec. 12, 2011. The prototypical substantially anhydrous chromium(III) halide complex or anhydrous chromium(III) halide complex is the tetrahydrofuran complex, $CrCl_3(THF)_3$. The general paucity of simple techniques for synthesizing this THF complex can make it an inconvenient and expensive starting material. For example, several methods of producing $CrCl_3(THF)_3$ can require the initial formation of the unsolvated chromium(III) chloride $CrCl_3$, which itself can be formed from heating and drying hydrated chromic chloride with reagents that can consume water, such as thionyl chloride, acetic anhydride, or trimethylchlorosilane. The neutral ligand-free or solvent-free halides $CrX_3$ (wherein X is a halide), in turn, can be converted to the chromium(III) halide complexes such as $CrX_3L_3$ by coordination with a non-aqueous neutral ligand, L, such as tetrahydrofuran (THF). The Soxhlet extraction of anhydrous chromic chloride with THF using zinc metal similarly can require an unsolvated chromium(III) chloride $CrCl_3$ starting material. Moreover, simply heating the hydrated metal halides of the electrophilic early transition metals typically does not constitute a viable method for preparing anhydrous metal halide complexes.

Among other things, this disclosure provides simple routes for the preparation of solvated anhydrous metal halides, such as anhydrous first-row transition metal halides, and in particular, anhydrous halides of chromium, including those of chromium(III). Examples of chromium(III) complex preparations can be found in the following references: Tyree, S. Y., Jr. Inorg. Synth. 1953, 4, 105; Herwig, W. and Zeiss, H. H. J. Org. Chem. 1958, 23, 1404; Pray, A. R. Inorg. Synth. 1957, 5, 153; Kern, R. J. J. Inorg. Nucl. Chem. 1962, 24, 1105; Jones, P. J. et al. Inorg. Chem. 1983, 22, 2642; and So, J.-H. and Boudjouk, P. Inorg. Chem. 1990, 29, 1592. Each of these documents publications are incorporated herein by reference in their entirety.

In one aspect of this disclosure, there is provided a process for preparing a chromium(III) halide complex, comprising: contacting 1) a chromium(III) halide hydrate, 2) a water absorption agent, and 3) a coordinating compound, L, to form a chromium(III) halide complex having the formula $CrX_3 \cdot mL$. Within the chromium(III) halide complex having the formula $CrX_3 \cdot mL$, X represents a halide, L represents a coordinated coordinating compound (also referred to as a coordinating ligand), and m represents the number of moles of coordinating compounds (or coordinated ligands) per mole of chromium. In an embodiment, the chromium(III) halide complex of the formula $CrX_3 \cdot mL$ can be isolated. In an aspect, the chromium(III) halide complex can have a water content of less than or equal to 100 ppm; alternatively, less than or equal to 70 ppm; alternatively, less than or equal to 50 ppm; or alternatively, less than or equal to 20 ppm. Generally, the water content of the chromium(III) halide complex is based upon the weight percentage of water in the chromium (III) halide complex. In another aspect of this disclosure and in any disclosed embodiment, the chromium(III) halide complex, $CrX_3 \cdot mL$, can be formed under condition capable of forming the chromium(III) halide complex. In some embodiments, the chromium(III) halide complex can be formed at ambient temperature and atmospheric pressure. Thus, contact conditions can include simply contacting the recited components at ambient temperature (15° C. to 35° C.), at the atmospheric pressure (about 1 atmosphere).

While not intending to be limiting as a method of preparing chromium(II) chloride complexes or as a method of preparing specific chromium(III) halide complexes such as $CrCl_3(THF)_3$, the process as applied to the preparation of $CrCl_3(THF)_3$ can be instructive as to how this method can be generally carried out, and is used as an example throughout. Thus, not as a limitation, the present disclosure provides, among other things, a process for preparing $CrCl_3(THF)_3$, the process comprising: contacting 1) a chromium(III) chloride hydrate, 2) a water absorption agent, and 3) tetrahydrofuran to form $CrCl_3(THF)_3$. In some embodiments, the process for preparing $CrCl_3(THF)_3$ can comprise: contacting 1) $CrCl_3 \cdot 6H_2O$, 2) tetrahydrofuran, and 3) 3 Å, 4 Å, 5 Å, 10×, or 13× molecular sieves to form $CrCl_3(THF)_3$. In some embodiments, there is provided an additional step of isolating the $CrCl_3(THF)_3$. In other embodiments, the $CrCl_3(THF)_3$ can have a water content of less than 100 ppm (or any other chromium(III) halide complex water content disclosed herein). In another embodiment, $CrCl_3(THF)_3$ can be formed under condition capable of forming $CrCl_3(THF)_3$. In yet other embodiments, $CrCl_3(THF)_3$ can be formed at ambient temperature and atmospheric pressure.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the table are indicated using the numbering scheme indicated in the version of the periodic table of elements published in Chemical and Engineering News, 63(5), 27, 1985. In some instances a group of elements can be indicated using a common name assigned to the group; for example alkali metals for Group 1 elements, alkaline earth metals for Group 2 elements, transition metals for Group 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class which is utilized and it is possible to have different transitional terms or phrases utilized with different features within a claim. For example, a method can comprise several recited steps (and other non-recited steps) but utilize a catalyst system preparation consisting of specific or alternatively consist of specific steps and/or utilize a catalyst system comprising recited components and other non-recited components.

Within this disclosure, use of "comprising" or an equivalent expression contemplates the use of the phrase "consisting essentially of," "consists essentially of," or equivalent expressions as an alternative embodiments to the open-ended expression. Additionally, use of "comprising" or an equivalent expression or use of "consisting essentially of" in the specification contemplates the use of the phrase "consisting of," "consists of," or equivalent expression as an alternative to the open-ended expression or middle ground expression, respectively. For example, "comprising" should be understood to include "consisting essentially of," and "consisting of" as alternative embodiments for the aspect, features, and/or elements presented in the specification unless specifically indicated otherwise.

The terms "a," "an," and "the" are intended, unless specifically indicated otherwise, to include plural alternatives (e.g., at least one). For instance, the disclosure of "a chromium halide hydrate" is meant to encompass one chromium halide hydrate, or mixtures or combinations of more than one chromium halide hydrate unless otherwise specified.

In this disclosure, the terms first, second, and third, among others, can be utilized to differentiate multiple occurrences of a similar element. For example a process can utilize two or more solvents in one or more steps of a process, or alternatively two different solvents in a mixture. The differentiating term can be applied to any element described herein when necessary to provide a differentiation. It should be understood that the numerical or alphabetical precedence of the differentiating terms do not imply a particular order or preference of the element in a method or compound described herein unless specifically specified otherwise.

In this disclosure, a process can have multiple steps or can include features having a number of different elements (e.g., components in a catalyst system or components in an olefin trimerization oligomerization process, among other features). This steps and/or elements can be designated utilizing the series a), b), c), etc., i), ii), iii), etc., (a), (b), (c), etc., and/or (i), (ii), (iii), etc. (among other designation series) as necessary to provide a designation for each process step and/or element. It should be understood that the numerical or alphabetical precedence of the designations within a designation series does not imply a particular order or preference of the process step in a process described herein, the feature(s) described herein, and/or an element(s) in a feature unless specifically specified otherwise or necessitated by other process steps, elements, and/or element features. Additionally, these designations series are provided to differentiate different process steps and/or elements in a feature and can be utilized as necessary, and without regard to the designation series utilized for a particular step, element, or feature utilized within this description as long as the designation series consistently distinguish different features, different process steps, and/or different elements of a feature.

The term "substantially anhydrous," when referring to a compound, solution, solvent, or general conditions, means that the concentration of water is less than or equal to 100 ppm (by weight) based upon the weight of the compound, solution, or solvent. The term "substantially dry," when referring to an atmosphere, means that the atmosphere, regardless of the atmosphere's composition, means that the amount of water in the atmosphere is less than or equal to 100 ppm, by weight.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel.

The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

A "water absorption agent" is used herein to refer to any compound or composition that can be employed as a dehydrating agent without chemically breaking a water oxygen-hydrogen bond, that is, without forming $H^+$ or $OH^-$ or forming a reaction product with the dehydrating agent as a result of its dehydrating action. In an aspect, the "water absorption agent" can be a solid. In another aspect, the "water absorption agent" can refer to any solid compound or composition that can be employed as a dehydrating agent without the formation of acid or base as a result of its dehydrating action. For example, solids such as zeolites and molecular are examples of "water absorption agents" according to this disclosure, but solids such as $P_2O_5$ are not included in this description. The term "absorption" is used as a general indication of dehydrating action when the agent or substance takes in water, and is not limited to any particular mechanism or type of molecular, bulk, or surface phenomenon. Thus, the term "absorption" is used regardless of whether the water being removed enters some bulk phase or volume of the substance (e.g., a pore of a zeolite of molecular sieve), or whether the water being removed is taken up by the surface of the substance, or a combination thereof. Consequently, the use of term "absorption" in this disclosure encompasses both "absorption" and "adsorption" processes.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise. Other identifiers or qualifying terms may be utilized to indicate the presence or absence of a particular substituent, a particular regiochemistry and/or stereochemistry, or the presence or absence of a branched underlying structure or backbone.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

A "nitrile" is an organic compound having the formula $R^1C\equiv N$, wherein $R^1$ is provided herein. Aliphatic nitriles are nitriles which do not contain aromatic groups. Aromatic nitriles are nitriles which have aromatic groups (e.g., benzonitrile).

An "ether" is an organic compound having the formula $R^2$—O—$R^3$ wherein $R^2$ and $R^3$ are provided herein. Aliphatic ethers are ethers which do not have aromatic groups. Aromatic ethers are ethers which have aromatic groups (either containing or not containing the ether oxygen atom). Acyclic ethers are ethers in which the ether oxygen atom is not contained in a ring (but can have a ring, aliphatic or aromatic, as or within $R^2$ and/or $R^3$). Cyclic ethers are ethers wherein the ether oxygen atom is incorporated within a ring (either an aliphatic ring or aromatic ring). Aliphatic cyclic ethers are cyclic ethers wherein the ether oxygen atom is incorporated within an aliphatic ring (e.g., tetrahydrofuran, 2,3-dihydrofuran, pyran, among others). Aromatic cyclic ethers are ethers wherein the ether oxygen atom is incorporated within an aromatic ring or aromatic ring system (e.g., furan, benzofuran, isobenzofuran, among others).

A "thioether" is an organic compound having the formula $R^4$—S—$R^5$ wherein $R^4$ and $R^5$ are provided herein. Aliphatic thioethers are thioethers which do not have aromatic groups.

Aromatic thioethers are ethers which have aromatic groups (either containing or not containing the thioether sulfur atom). Acyclic thioethers are thioethers in which the thioether sulfur atom is not contained in a ring (but can have ring, aliphatic or aromatic, as or within $R^4$ and/or $R^5$). Cyclic thioethers are thioethers wherein the thioether sulfur atom is incorporated within a ring (either an aliphatic ring or aromatic ring). Aliphatic cyclic thioethers are cyclic thioethers wherein the thioether sulfur atom is incorporated within an aliphatic ring (e.g., tetrahydrothiophene, thiane, among others). Aromatic cyclic thioethers are thioethers wherein the thioether sulfur atom is incorporated within an aromatic ring or aromatic ring system (e.g., thiophene, benzothiophene, among others).

An "amine" is an organic compound having the formula $NR^6R^7R^8$, $NHR^6R^7$, $NH_2R^6$, or $NH_3$, wherein $R^6$, $R^7$, and $R^8$ are provided herein. Aliphatic amines are amines which do not have aromatic groups. Aromatic amines are amines which have aromatic groups (either containing or not containing the amine nitrogen atom). Acyclic amines are amines in which the amine nitrogen atom is not contained in a ring (but can have a ring, aliphatic or aromatic, as or within $R^6$, $R^7$, and/or $R^8$). Cyclic amines are amines wherein the amine nitrogen atom is incorporated within a ring (either an aliphatic ring or aromatic ring). Aliphatic cyclic amines are cyclic amines wherein the amine nitrogen atom is incorporated within an aliphatic ring (e.g., pyrrolidine, piperidine, among others). Aromatic cyclic amines are amines wherein the amine nitrogen atom is incorporated within an aromatic ring or aromatic ring system (e.g., pyridine, pyrrole, indole, among others).

A "phosphine" is an organic compound having the formula $PR^9R^{10}R^{11}$, $PHR^9R^{10}$, or $PH_2R^9$, wherein $R^9$, $R^{10}$, and $R^{11}$ are provided herein. Aliphatic phosphines are phosphines which do not have aromatic groups. Aromatic phosphines are phosphines which have aromatic groups (either containing or not containing the phosphine phosphorus atom). Acyclic phosphines are phosphines in which the phosphine phosphorus atom is not contained in a ring (but can have a ring, aliphatic or aromatic, as or within $R^9$, $R^{10}$, and/or $R^{11}$). Cyclic phosphines are phosphines wherein the phosphine phosphorus atom is incorporated within a ring (either an aliphatic ring or aromatic ring). Aliphatic cyclic phosphines are cyclic phosphines wherein the phosphine phosphorus atom is incorporated within an aliphatic ring (e.g., phospholane, phosphinane, among others). Aromatic cyclic phosphines are phosphines wherein the phosphine phosphorus atom is incorporated within an aromatic ring or aromatic ring system (e.g., phosphole, among others).

A "phosphite" is an organic compound having the formula $P(OR^{12})(OR^{13})(OR^{14})$ or $PH(O)(OR^{12})(OR^{13})$, wherein $R^{12}$, $R^{13}$, and $R^{14}$ are provided herein. Aliphatic phosphites are phosphites which do not have aromatic groups. Aromatic phosphites are phosphites which have aromatic groups (either containing or not containing the phosphite phosphorus atom). Acyclic phosphites are phosphites in which the phosphite phosphorus atom is not contained in a ring (but can have a ring, aliphatic or aromatic, as or within $R^{12}$, $R^{13}$, and/or $R^{14}$). Cyclic phosphites are phosphites wherein the phosphite phosphorus atom is incorporated within a ring (either an aliphatic ring or aromatic ring). Aliphatic cyclic phosphites are cyclic phosphites wherein the phosphite phosphorus atom is incorporated within an aliphatic ring. Aromatic cyclic phosphites are phosphites wherein the phosphite phosphorus atom is incorporated within an aromatic ring or aromatic ring system.

The term "cyclic" as compared to an "acyclic" when referring to an ether, thioether, amine, phosphine, or phosphite is used to refer to a compound in which the heteroatom O, S, N, or P, respectively, is encompassed within a cyclic structure, which also encompasses the $R^2$ and $R^3$ groups of the ether $R^2$—O—$R^3$, the $R^4$ and $R^5$ groups of the thioether $R^4$—S—$R^5$, any combination of $R^6$, $R^7$, and $R^8$ of the amine $NR^6R^7R^8$ or $NHR^6R^7$, any combination of $R^9$, $R^{10}$, and $R^{11}$ of the phosphine $PR^9R^{10}R^{11}$ or $PHR^9R^{10}$, or any combination of $R^{12}$, $R^{13}$, and $R^{14}$ of the phosphite $P(OR^{12})(OR^{13})(OR^{14})$ or $PH(O)(OR^{12})(OR^{13})$. For example, a "cyclic ether" is an analog of the acyclic ether structure $R^2$—O—$R^3$, in which $R^2$ and $R^3$ are generally as provided above in describing the (acyclic) ether $R^2$—O—$R^3$, except that $R^2$ and $R^3$ are linked or bonded to each other by removing a hydrogen atom from each of $R^2$ and $R^3$ and forming a bond between $R^2$ and $R^3$ where the hydrogen atoms were removed so as to form a cyclic structure that includes the ether oxygen. Tetrahydrofuran (THF) is a prototypical cyclic ether that can be formally derived by removing a hydrogen atom from each $CH_3$ groups of diethyl ether ($CH_3CH_2OCH_2CH_3$) or a hydrogen atom from each $CH_3$ groups of methyl n-propyl ether ($CH_3CH_2CH_2OCH_3$), followed by linking or bonding the two carbons from which the hydrogen atoms are removed. Similarly, the cyclic ether 2-methyloxetane can be formally derived by removing a hydrogen atom from the $CH_3$ group of one ethyl group of ethyl ether and a hydrogen atom from the $CH_2$ of the other ethyl group of diethyl ether ($CH_3CH_2OCH_2CH_3$), followed by a formal linking of the two carbons from which the hydrogen atoms are removed.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group that can comprise functional groups and/or atoms in addition to carbon and hydrogen. For instance, non-limiting examples of atoms other than carbon and hydrogen can include, but is not limited to, halogens, oxygen, nitrogen, and phosphorus, among other elements. Non-limiting examples of functional groups include ethers, aldehydes, ketones, esters, sulfides, amines, and phosphines, and so forth. In one aspect, the hydrogen atom(s) removed to form the "organyl group," "organylene group," or "organic group" can be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), a N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" can be attached to a carbon atom not belonging to, and remote from, a functional group, for example, —CH$_2$C(O)CH$_3$, and —CH$_2$NR$_2$, among others. An "organyl group," "organylene group," or "organic group" can be aliphatic, inclusive of being cyclic or acyclic, or can be aromatic. "Organyl groups," "organylene groups," and "organic groups" also can encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene groups, alkyl, alkylene, alkane group, cycloalkyl, cycloalkylene, cycloalkane groups, aralkyl, aralkylene, and aralkane groups, respectively, among other groups as members.

An aliphatic compound is an acyclic or cyclic, saturated or unsaturated, carbon compound, excluding aromatic compounds. An "aliphatic group" is a generalized group formed by removing one or more hydrogen atoms (as necessary for the particular group) from the carbon atom of an aliphatic compound. Aliphatic compounds and aliphatic groups can contain organic functional group(s) and/or atom(s) other than carbon and hydrogen.

The term "alkane" whenever used in this specification and claims refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl group are derived by removal of a hydrogen atom from a primary, secondary, tertiary carbon atom, respectively, of an alkane. The n-alkyl group derived by removal of a hydrogen atom from a terminal carbon atom of a linear alkane. The groups $RCH_2$ (where R is not H), $R_2CH$ (where R is not H), and $R_3C$ (where R is not H) are primary, secondary, and tertiary alkyl groups, respectively.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, and so forth, endocyclic double or triple bonds can be identified by use of the term "mono," "di," "tri," and so forth, within the name of the cycloalkene or cycloalkyne. Cycloalkenes and cycloalkynes can further identify the position of the endocyclic double or triple bonds. Other identifiers can be utilized to indicate the presence of particular groups in the cycloalkane (e.g., halogenated cycloalkane indicates that the presence of one or more halogen atoms replacing an equivalent number of hydrogen atoms in the cycloalkane).

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

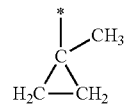

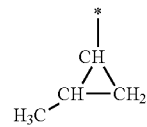

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g., a methylcyclo-propyl group) and is member of the group of hydrocarbon groups. However, when referring to a cycloalkane group having a specified number of cycloalkane ring carbon atoms (e.g., cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g., substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

The term "olefin" whenever used in this specification and claims refers to compounds that have at least one carbon-carbon double bond that is not part of an aromatic ring or ring system. The term "olefin" includes aliphatic and aromatic, cyclic and cyclic, and/or linear and branched compounds having at least one carbon-carbon double bond that is not part of an aromatic ring or ring system unless specifically stated otherwise. The term "olefin," by itself, does not indicate the presence or absence of heteroatoms and/or the presence or absence of other carbon-carbon double bonds unless explicitly indicated. Olefins having only one, only two, only three, and so forth, carbon-carbon double bonds can be identified by use of the term "mono," "di," "tri," and so forth, within the name of the olefin. The olefins can be further identified by the position of the carbon-carbon double bond(s).

The term "alkene" whenever used in this specification and claims refers to a hydrocarbon olefin that has at least one non-aromatic carbon-carbon double bond. The term "alkene" includes aliphatic or aromatic (an alkene having an aromatic substituent within the compound), cyclic or acyclic, and/or linear and branched compounds having at least one non-aromatic carbon-carbon double bond unless expressly stated otherwise. Alkenes having only one, only two, only three, and so forth, carbon-carbon double bonds can be identified by use of the term "mono," "di," "tri," and so forth, within the name. For example, alkamonoenes, alkadienes, and alkatrienes refer to a linear or branched hydrocarbon olefins having only one carbon-carbon double bond (general formula $C_nH_{2n}$), only two carbon-carbon double bonds (general formula $C_nH_{2n-2}$), and only three carbon-carbon double bonds (general formula $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replace with a halogen atom.

An "alkenyl group" is a univalent group derived from an alkene by removal of a hydrogen atom from any carbon atom of the alkene. Thus, "alkenyl group" includes groups in which the hydrogen atom is formally removed from a sp2 hybridized (olefinic) carbon atom and groups in which the hydrogen atom is formally removed from any other carbon atom. For example and unless otherwise specified, propen-1-yl (—CH=CHCH$_3$), propen-2-yl[(CH$_3$)C=CH$_2$], and propen-3-yl (—CH$_2$CH=CH$_2$) groups are all encompassed with the term "alkenyl group." Similarly, an "alkenylene group" refers to a group formed by formally removing two hydrogen atoms from an alkene, either two hydrogen atoms from one carbon atom or one hydrogen atom from two different carbon atoms. An "alkene group" refers to a generalized group formed by removing one or more hydrogen atoms (as necessary for the particular group) from an alkene. When the hydrogen atom is removed from a carbon atom participating in a carbon-carbon double bond, the regiochemistry of the carbon from which the hydrogen atom is removed, and regiochemistry of the carbon-carbon double bond can both be specified. Alkenyl groups can also have more than one such multiple bond. The alkene group can also be further identified by the position of the carbon-carbon double bond(s). Other identifiers can be utilized to indicate the presence or absence of particular groups within an alkene group. For example, a haloalkene group refers to an alkene group having one or more hydrogen atoms replaced with a halogen atom.

The term "alkyne" is used in this specification and claims to refer to a hydrocarbon compound that has at least one non-aromatic carbon-carbon triple bond. The term "alkyne" includes aliphatic or aromatic (an alkyne having an aromatic substituent within the compound), cyclic or acyclic, and/or linear and branched compounds having at least one non-aromatic carbon-carbon triple bond unless expressly stated otherwise. Alkynes having only one, only two, only three, and so forth, carbon-carbon triple bonds can be identified by use of the term "mono," "di," "tri," and so forth, within the name. For example, alkamonoynes, alkadiynes, and alkatriynes refer to a linear or branched hydrocarbon olefins having only one carbon-carbon triple bond (general formula $C_nH_{2n-2}$), only two carbon-carbon triple bonds (general formula $C_nH_{2n-6}$), and only three carbon-carbon triple bonds (general formula $C_nH_{2n-10}$), respectively. Alkynes can be further identified by the position of the carbon-carbon triple bond(s). Other identifiers can be utilized to indicate the presence or absence of particular groups within an alkyne. For example, a haloalkyne refers to an alkyne having one or more hydrogen atoms replace with a halogen atom.

An "alkynyl group" is a univalent group derived from an alkyne by removal of a hydrogen atom from any carbon atom of the alkyne. Thus, "alkynyl group" includes groups in which the hydrogen atom is formally removed from a sp hybridized (acetylenic) carbon atom and groups in which the hydrogen atom is formally removed from any other carbon atom. For example and unless otherwise specified, propyn-1-yl (—C≡CCH$_3$) and propyn-1-yl (HC≡CCH$_2$—) groups are all encompassed with the term "alkynyl group." Similarly, an "alkynylene group" refers to a group formed by formally removing two hydrogen atoms from an alkyne, either two hydrogen atoms from one carbon atom if possible or one hydrogen atom from two different carbon atoms. An "alkyne group" refers to a generalized group formed by removing one or more hydrogen atoms (as necessary for the particular group) from an alkyne. Alkynyl groups can also have more than one such multiple bond. The alkyne group can also be further identified by the position of the carbon-carbon triple bond(s). Other identifiers can be utilized to indicate the presence or absence of particular groups within an alkyne group. For example, a haloalkyne group refers to an alkyne group having one or more hydrogen atoms replaced with a halogen atom.

A "heterocyclic compound" is a cyclic compound having at least two different elements as ring member atoms. For example, heterocyclic compounds can comprise rings containing carbon and nitrogen (for example, tetrahydropyrrole and pyrrole, among others), carbon and oxygen (for example, tetrahydrofuran and furan, among others), or carbon and sulfur (for example, tetrahydrothiophene and thiophene, among others). Heterocyclic compounds and heterocyclic groups can be either aliphatic or aromatic.

A "heterocyclyl group" is a univalent group formed by removing a hydrogen atom from a heterocyclic ring or ring system carbon atom of a heterocyclic compound. By specifying that the hydrogen atom is removed from a heterocyclic ring or ring system carbon atom, a "heterocyclyl group" is distinguished from a "cycloheteryl group," in which a hydrogen atom is removed from a heterocyclic ring or ring system heteroatom. For example, a pyrrolidin-2-yl group illustrated below is one example of a "heterocyclyl group," and a pyrrolidin-1-yl group illustrated below is one example of a "cycloheteryl" group."

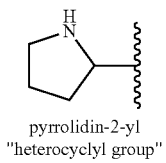

pyrrolidin-2-yl
"heterocyclyl group"

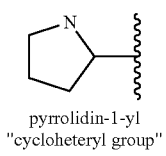

pyrrolidin-1-yl
"cycloheteryl group"

Similarly, a "heterocyclylene group" or more simply, a "heterocyclene group," refers to a group formed by removing two hydrogen atoms from a heterocyclic compound, at least one of which is from a heterocyclic ring or ring system carbon. Thus, in a "heterocyclylene group," at least one hydrogen is removed from a heterocyclic ring or ring system carbon atom, and the other hydrogen atom can be removed from any other carbon atom, including for example, the same heterocyclic ring or ring system carbon atom, a different heterocyclic ring or ring system ring carbon atom, or a non-ring carbon atom. A "heterocyclic group" refers to a generalized group formed by removing one or more hydrogen atoms (as necessary for the particular group and at least one of which is a heterocyclic ring carbon atom) from a heterocyclic compound.

A "cycloheteryl group" is a univalent group formed by removing a hydrogen atom from a heterocyclic ring or ring system heteroatom of a heterocyclic compound, as illustrated herein. By specifying that the hydrogen atom is removed from a heterocyclic ring or ring system heteroatom and not from a ring carbon atom, a "cycloheteryl group" is distinguished from a "heterocyclyl group" in which a hydrogen atom is removed from a heterocyclic ring or ring system carbon atom. Similarly, a "cycloheterylene group" refers to a group formed by removing two hydrogen atoms from an heterocyclic compound, at least one of which is removed from a heterocyclic ring or ring system heteroatom of the heterocyclic compound; the other hydrogen atom can be removed from any other atom, including for example, a heterocyclic ring or ring system ring carbon atom, another heterocyclic ring or ring system heteroatom, or a non-ring atom (carbon or heteroatom). A "cyclohetero group" refers to a generalized group formed by removing one or more hydrogen atoms (as necessary for the particular group and at least one of which is from a heterocyclic ring or ring system heteroatom) from a heterocyclic compound.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen—diphenyl ether; nitrogen—triphenyl amine; among other linking groups). As disclosed herein, the term "substituted" can be used to describe an aromatic group, an arene, or a heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An arene is an aromatic hydrocarbon, with or without side chains (e.g., benzene, toluene, or xylene, among others). An "aryl group" is a group derived from the formal removal of a hydrogen atom from an aromatic ring carbon of an arene. It should be noted that the arene can contain a single aromatic hydrocarbon ring (e.g., benzene, or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane). One example of an "aryl group" is ortho-tolyl (o-tolyl), the structure of which is shown here.

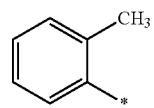 [SMILES: *c1ccccc1C]

Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. However, if a group contains separate and distinct arene and heteroarene rings or ring systems (e.g., the phenyl and benzofuran moieties in 7-phenyl-benzofuran) its classification depends upon the particular ring or ring system from which the hydrogen atom was removed, that is, an arene group if the removed hydrogen came from the aromatic hydrocarbon ring or ring system carbon atom (e.g., the 2 carbon atom in the phenyl group of 6-phenylbenzofuran) and a heteroarene group if the removed hydrogen carbon came from a heteroaromatic ring or ring system carbon atom (e.g., the 2 or 7 carbon atom of the benzofuran group or 6-phenylbenzofuran). It should be noted that according the definitions provided herein, general arene groups (including an aryl group and an arylene group) include those having zero, one, or more than one hydrocarbyl substituent groups located on an aromatic hydrocarbon ring or ring system carbon atom (e.g., a toluene group or a xylene group, among others) and is a member of the group of hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, or hydrocarboxy groups, among others) located on an aromatic hydrocarbon ring or ring system carbon atom. When the substituted phenyl group and/or substituted naphthyl group is a member of the group of hydrocarbon groups (or a member of the general group of arene groups), each substituent is limited to a hydrocarbyl substituent group. One can readily discern and select general substituted phenyl and/or substituted naphthyl groups, specific substituted phenyl and/or substituted naphthyl groups, and/or individual substituted phenyl or substituted naphthyl groups which can be utilized as a member of the group of hydrocarbon groups (or a member of the general group of arene groups).

A heteroarene is aromatic compound, with or without side chains, having a heteroatom within the aromatic ring or aromatic ring system (e.g., pyridine, indole, or benzofuran, among others). A "heteroaryl group" is a class of "heterocyclyl group" and is a univalent group formed by removing a hydrogen atom from a heteroaromatic ring or ring system carbon atom of a heteroarene compound. By specifying that the hydrogen atom is removed from a ring carbon atom, a "heteroaryl group" is distinguished from an "arylheteryl group," in which a hydrogen atom is removed from a heteroaromatic ring or ring system heteroatom. For example, an indol-2-yl group illustrated below is one example of a "heteroaryl group," and an indol-1-yl group illustrated below is one example of an "arylheteryl" group."

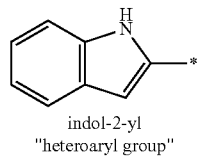 [SMILES: *c1cc2ccccc2[nH]1]

indol-2-yl
"heteroaryl group"

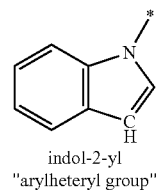

indol-2-yl
"arylheteryl group"

Similarly, a "heteroarylene group" refers to a group formed by removing two hydrogen atoms from a heteroarene compound, at least one of which is from a heteroarene ring or ring system carbon atom. Thus, in a "heteroarylene group," at least one hydrogen is removed from a heteroarene ring or ring system carbon atom, and the other hydrogen atom can be removed from any other carbon atom, including for example, a heteroarene ring or ring system carbon atom, or a non-heteroarene ring or ring system atom. A "heteroarene group" refers to a generalized group formed by removing one or more hydrogen atoms (as necessary for the particular group and at least one of which is a heteroarene ring or ring system carbon atom) from a heteroarene compound. If a hydrogen atom is removed from a heteroaromatic ring or ring system heteroatom and from a heteroaromatic ring or ring system carbon atom or an aromatic hydrocarbon ring or ring system carbon atom, the group is classified as an "arylheterylene group" or an "arylhetero group."

An "arylheteryl group" is a class of "cycloheteryl group" and is a univalent group formed by removing a hydrogen atom from a heteroaromatic ring or ring system heteroatom, as illustrated. By specifying that the hydrogen atom is removed from of a heteroaromatic ring or ring system heteroatom and not from a heteroaromatic ring or ring system carbon atom, an "arylheteryl group" is distinguished from a "heteroaryl group" in which a hydrogen atom is removed from a heteroaromatic ring or a ring system carbon atom. Similarly, an "arylheterylene group" refers to a group formed by removing two hydrogen atoms from a heteroaryl compound, at least one of which is removed from a heteroaromatic ring or ring system heteroatom of the heteroaryl compound; the other hydrogen atom can be removed from any other atom, including for example, a heteroaromatic ring or ring system carbon atom, another heteroaromatic ring or ring system heteroatom, or a non-ring atom (carbon or heteroatom) from a heteroaromatic compound. An "arylhetero group" refers to a generalized group formed by removing one or more hydrogen atoms (as necessary for the particular group and at least one of which is from a heteroaromatic ring or ring system) heteroatom from a heteroarene compound.

An "aralkyl group" is an aryl-substituted alkyl group having a free valance at a non-aromatic carbon atom (e.g., a benzyl group, or a 2-phenyleth-1-yl group, among others). Similarly, an "aralkylene group" is an aryl-substituted alkylene group having two free valencies at a single non-aromatic carbon atom or a free valence at two non-aromatic carbon atoms while an "aralkane group" is a generalized is an aryl-substituted alkane group having one or more free valencies at a non-aromatic carbon atom(s). A "heteroaralkyl group" is a heteroaryl-substituted alkyl group having a free valence at a non-hetero-aromatic ring or ring system carbon atom. Similarly a "heteroaralkylene group" is a heteroaryl-substituted alkylene group having two free valencies at a single non-heteroaromatic ring or ring system carbon atom or a free valence at two non-heteroaromatic ring or ring system carbon atoms while a "heteroaralkane group" is a generalized aryl-substituted alkane group having one or more free valencies at a non-heteroaromatic ring or ring system carbon atom(s). It should be noted that according the definitions provided herein, general aralkane groups include those having zero, one, or more than one hydrocarbyl substituent groups located on an aralkane aromatic hydrocarbon ring or ring system carbon atom and is a member of the group of hydrocarbon groups. However, specific aralkane groups specifying a particular aryl group (e.g., the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "halide" has its usual meaning; therefore, examples of halides include fluoride, chloride, bromide, and iodide.

An "organoheteryl group" is a univalent group containing carbon, which are thus organic, but which have their free valence at an atom other than carbon. Thus, organoheteryl and organyl groups are complementary and mutually exclusive. Organoheteryl groups can be cyclic or acyclic, and/or aliphatic or aromatic, and thus encompasses aliphatic "cycloheteryl groups" (e.g., pyrrolidin-1-yl or morpholin-1-yl, among others), aromatic "arylheteryl groups" (e.g., pyrrol-1-yl or indol-1-yl, among others), and acyclic groups (e.g., organylthio, trihydrocarbylsilyl, aryloxy, or alkoxy, among others). Similarly, an "organoheterylene group" is a divalent group containing carbon and at least one heteroatom having two free valencies, at least one of which is at a heteroatom. An "organohetero group" is a generalized group containing carbon and at least one heteroatom having one or more free valencies (as necessary for the particular group and at least one of which is at a heteroatom) from an organohetero compound.

If a compound or group contains more than one moiety it is formally a member of the group having the highest naming priority as stipulated by IUPAC. For example 4-phenylpyridine is a heteroaromatic compound and a 4-(phen-2-ylene) pyridin-2-yl group is heteroaromatic group because the highest naming group is the pyridine group and the pyridin-2-yl group respectively.

In an aspect, this disclosure provides for methods for preparing chromium(III) halide complexes, comprising: contacting 1) a chromium(III) halide hydrate, 2) a water absorption agent, and 3) a coordinating compound, L, to form a chromium(III) halide complex having the formula $CrX_3 \cdot mL$. In an embodiment, the chromium(III) halide complex can be formed under conditions capable of forming a chromium halide complex. In another embodiment, the chromium(III) halide complex can be isolated; alternatively, purified, or alternatively, isolated and purified. Generally, the chromium (III) halide hydrate, the water absorption agent, the coordinating compound, the chromium(III) halide complex formation conditions, the method of isolation and/or purifying the chromium(III) halide complex, among other method elements, are independent elements of the method to prepare chromium(III) halide complexes. Each of these method elements, and other elements, are independently described in this disclosure and can be combined in any fashion to describe the method for preparing chromium(III) halide complexes.

In one aspect, the chromium(III) halide hydrate can have the formula $CrX_3(L^1)_q \cdot nH_2O$; or alternatively, have the formula $CrX_3 \cdot nH_2O$. Within the chromium(III) halide hydrate formulas, X represent a halide, $L^1$ represents a coordinating neutral ligand, q represent the number of $L^1$ coordinating ligands per mole of chromium, and n is the number of moles of $H_2O$ per mole of chromium. X, $L^1$, q, and n are independent elements of the chromium(III) halide hydrate having formula $CrX_3(L^1)_q \cdot nH_2O$ or $CrX_3 \cdot nH_2O$. Each of these chromium (III) halide hydrate elements, and other elements, are independently described in this disclosure and can be utilized, without limitation, to describe the chromium(III) halide hydrate having formula $CrX_3(L^1)_q \cdot nH_2O$ or $CrX_3 \cdot nH_2O$.

In an embodiment, each halide, X, independently can be F (fluorine), Cl (chlorine), Br, (bromine), or I (iodine). In some embodiments, each halide, X, can be F; alternatively, Cl; alternatively, Br; or alternatively, I.

In an embodiment, n can be a positive number (integer or non-integer); or alternatively, n can be a positive integer. By describing the chromium(III) halide hydrate with the formula $CrX_3(L^1)_q \cdot nH_2O$ or the formula $CrX_3 \cdot H_2O$, it is intended to reflect a general formula that includes all polymorphs of chromium(III) halide hydrates, including those in which the $H_2O$ is coordinated, those in which $H_2O$ is interstitial or situated in the crystalline lattice, and/or those in which a combination of coordinated $H_2O$ and lattice $H_2O$ are present. In this aspect, the use of any particular chromium(III) halide hydrate in the disclosed methods is not limited to the number of associated $H_2O$ molecules in the formula $CrX_3 \cdot H_2O$, and includes the use of chromium(III) halide hydrate that cannot have been reported as of the filing date of this disclosure.

In an embodiment, the number of moles of $H_2O$, n, per mole of chromium in the chromium(III) halide hydrate having the formula $CrX_3(L^1)_q \cdot nH_2O$ or $CrX_3 \cdot H_2O$ can be from 0.25 to 10; alternatively, from 0.3 to 9.5; alternatively, from 0.4 to 9.0; alternatively, from 0.5 to 8.5; alternatively, from 0.6 to 8.0; alternatively, from 0.7 to 7.5; alternatively, from 0.8 to 7.0; alternatively, from 0.9 to 6.5; alternatively, from 1.0 to 6.0; alternatively, from 1.25 to 5.5; alternatively, from 1.50 to 5.0; alternatively, from 1.75 to 4.5; or alternatively, from 2.0 to 4.0. In some embodiments, the number of moles of $H_2O$, n, per mole of chromium in the chromium(III) halide hydrate having the formula $CrX_3(L^1)_q \cdot nH_2O$ or $CrX_3 \cdot nH_2O$ can be about 0.25; alternatively, about 0.5; alternatively, about 0.75; alternatively, about 1; alternatively, about 1.5; alternatively, about 2; alternatively, about 2.5; alternatively, about 3; alternatively, about 3.5; alternatively, about 4; alternatively, about 4.5; alternatively, about 5; alternatively, about 5.5; alternatively, about 6; alternatively, about 7; alternatively, about 8; alternatively about 9; or alternatively, about 10. In other embodiments, the number of moles of $H_2O$, n, per mole of chromium in the chromium(III) halide hydrate having the formula $CrX_3(L^1)_q \cdot nH_2O$ or $CrX_3 \cdot H_2O$ can be an integer from 1 to 10; alternatively from 1 to 9; alternatively, from 1 to 8; alternatively, from 1 to 7; or alternatively, from 1 to 6. In yet other embodiments, the number of moles of $H_2O$, n, per mole of chromium in the chromium(III) halide hydrate having the formula $CrX_3(L^1)_q \cdot nH_2O$ or $CrX_3 \cdot H_2O$ can be 1; alternatively, 2; alternatively, 3; alternatively, 4; alternatively, 5; alternatively, 6; alternatively, 7; alternatively, 8; alternatively, 9; or alternatively, 10.

In an embodiment, $L^1$ can be a coordinating ligand. In some embodiments, $L^1$ can be a neutral coordinating ligand It should be understood that the terms "coordinating ligand"

and "coordinating compound" (and by analogy "neutral coordinating ligand" and "neutral coordinating compound") refer to the same material. When the material is coordinated to chromium, it can be referred to as a ligand while when the material is utilized in the process to prepare the chromium (III) halide complex it can be referred to as a compound. The same situation applies to the L in relation to any chromium halide complex satisfying the formula $CrX_3.mL$ (or alternatively $CrX_3L_m$) and the coordinating compound, L. In some embodiments, the coordinating ligand, $L_1$, can be the same as the coordinating compound, L (or the coordinating ligand, L, of the chromium(III) halide complex having the formula $CrX_3.mL$); or alternatively, the coordinating ligand, $L^1$, and the coordinating compound, L (or the coordinating ligand, L, of the chromium(III) halide complex having the formula $CrX_3.mL$) can be different. The coordinating compound, and consequently the coordinating ligand, is independently described herein and its aspects and embodiments can be utilized without limitation to further describe the chromium (III) halide hydrate having the formula $CrX_3(L^1)_q.nH_2O$. If the coordinating compound (neutral or otherwise) is utilized as a solvent, it can further be referred to as a coordinating solvent (neutral or otherwise).

In an embodiment, the number of coordinating ligands of the chromium(III) halide hydrate having the formula $CrX_3(L^1)_q.nH_2O$ can be a positive number; or alternatively, a positive integer. By describing the chromium(III) halide hydrate with the formula $CrX_3(L^1)_q.nH_2O$, it is intended to reflect a general formula that includes all polymorphs of chromium (III) halide hydrates having the formula $CrX_3(L^1)_q.nH_2O$, including those in which the $L^1$ is coordinated, those in which $L^1$ is interstitial or situated in the crystalline lattice, and/or those in which a combination of coordinated $L^1$ and lattice $L^1$ are present. In this aspect, the use of any particular chromium (III) halide hydrate with the formula $CrX_3(L^1)_q.nH_2O$ in the disclosed methods is not limited to the number of associated $L^1$ ligands in the formula with the formula $CrX_3(L^1)_q.nH_2O$, and includes the use of chromium(III) halide hydrate with the formula $CrX_3(L^1)_q.nH_2O$ that cannot have been reported as of the filing date of this disclosure.

In an embodiment, the number of moles of $H_2O$ per mole of chromium, q, in the chromium(III) halide hydrate having the formula $CrX_3(L^1)_q.nH_2O$ can be from 0.25 to 10; alternatively, from 0.3 to 9.5; alternatively, from 0.4 to 9.0; alternatively, from 0.5 to 8.5; alternatively, from 0.6 to 8.0; alternatively, from 0.7 to 7.5; alternatively, from 0.8 to 7.0; alternatively, from 0.9 to 6.5; alternatively, from 1.0 to 6.0; alternatively, from 1.25 to 5.5; alternatively, from 1.50 to 5.0; alternatively, from 1.75 to 4.5; or alternatively, from 2.0 to 4.0. In some embodiments, the number of moles of $H_2O$ per mole of chromium, q, in the chromium(III) halide hydrate having the formula $CrX_3(L^1)_q.nH_2O$ can be about 0.25; alternatively, about 0.5; alternatively, about 0.75; alternatively, about 1; alternatively, about 1.5; alternatively, about 2; alternatively, about 2.5; alternatively, about 3; alternatively, about 3.5; alternatively, about 4; alternatively, about 4.5; alternatively, about 5; alternatively, about 5.5; alternatively, about 6; alternatively, about 7; alternatively, about 8; alternatively about 9; or alternatively, about 10. In other embodiments, the number of moles of $H_2O$ per mole of chromium, q, in the chromium(III) halide hydrate having the formula $CrX_3(L^1)_q.nH_2O$ can be an integer from 1 to 10; alternatively from 1 to 9; alternatively, from 1 to 8; alternatively, from 1 to 7; or alternatively, from 1 to 6. In yet other embodiments, the number of moles of $H_2O$ per mole of chromium, q, in the chromium(III) halide hydrate having the formula $CrX_3(L^1)_q.nH_2O$ can be 1; alternatively, 2; alternatively, 3; alternatively, 4; alternatively, 5; alternatively, 6; alternatively, 7; alternatively, 8; alternatively, 9; or alternatively, 10.

In any aspect or embodiment disclosed herein, the chromium(III) halide hydrate can be a chromium(III) chloride hydrate or a chromium(III) bromide hydrate; alternatively, a chromium(III) chloride hydrate or a chromium(III) bromide hydrate. The chromium(III) chloride hydrate can have the formula $CrCl_3(L^1)_q.nH_2O$ or $CrCl_3.nH_2O$; alternatively, $CrCl_3(L^1)_q.nH_2O$; or alternatively, $CrCl_3.nH_2O$. The chromium(III) chloride hydrate can have the formula $CrCl_3(L^1)_q.nH_2O$ or $CrCl_3.H_2O$; alternatively, $CrCl_3(L^1)_q.nH_2O$; or alternatively, $CrCl_3.nH_2O$. The chromium(III) bromide hydrate can have the formula $CrBr_3(L^1)_q.nH_2O$ or $CrBr_3.nH_2O$; alternatively, $CrBr_3(L^1)_q.nH_2O$; or alternatively, $CrBr_3.nH_2O$. $L^1$, q, and n are independently described in this disclosure and can be utilized without limitation to describe the chromium(III) chloride hydrates or the chromium(III) bromide hydrates having the formula $CrCl_3(L^1)_q.nH_2O$, $CrCl_3.nH_2O$, $CrBr_3(L^1)_q.nH_2O$, or $CrBr_3.nH_2O$ which can be utilized with the methods described herein.

In a non-limiting embodiment, the chromium(III) halide hydrate can be, comprise, or consist essentially of, $CrF_3.nH_2O$, $CrCl_3.H_2O$, $CrBr_3.nH_2O$, $CrI_3.nH_2O$, or any combination thereof; alternatively, $CrF_3.nH_2O$; alternatively, $CrCl_3.nH_2O$; alternatively, $CrBr_3.nH_2O$; or alternatively, $CrI_3.nH_2O$. In some non-limiting embodiments, where the chromium(III) halide hydrate can be, comprise, or consist essentially of, $CrF_3.nH_2O$, $CrCl_3.nH_2O$, $CrBr_3.H_2O$, $CrI_3.nH_2O$ (either individually or in any combination), n can be any positive integer or non-integer provided herein, for example, ranging from about 0.25 to about 10 or an integer from 1 to 9. In a non-limiting embodiment, the chromium(III) halide hydrate can be, comprise, or consist essentially of, $CrF_3.4H_2O$, $CrCl_3.6H_2O$ (sometimes written as $[Cr(H_2O)_4Cl_2]Cl.2H_2O$), $CrBr_3.6H_2O$, $CrI_3.9H_2O$, or any combination thereof; alternatively, $CrF_3.4H_2O$; alternatively, $CrCl_3.6H_2O$; alternatively, $CrBr_3.6H_2O$; or alternatively, $CrI_3.9H_2O$. In other embodiments, chromium(III) halide hydrate can be, comprise, or consist essentially of, $CrCl_3(THF)_2(H_2O)$.

In an aspect and in any embodiment of this disclosure, a broad range of water absorption agents can be employed in the disclosed processes. In an embodiment, the water absorption agent can be, comprise, or consist essentially of, calcium sulfate, calcium chloride, calcium oxide, magnesium sulfate, sodium sulfate, potassium sulfate, magnesium perchlorate, barium oxide, an alumina, a silica, a silica gel, gypsum, montmorillonite, a molecular sieve, a zeolite, or any combination thereof. In an embodiment, the water absorption agent can be, comprise, or consist essentially of, calcium sulfate, magnesium sulfate, sodium sulfate, potassium sulfate, or any combination thereof; alternatively, calcium oxide, barium oxide, or a combination thereof; alternatively, an alumina, a silica, a silica gel, gypsum, montmorillonite, a molecular sieve, a zeolite, or any combination thereof. In an embodiment, the water absorption agent can be, comprise, or consist essentially of, calcium sulfate, calcium chloride, calcium oxide, magnesium sulfate, sodium sulfate, potassium sulfate, magnesium perchlorate, barium oxide, or any combination thereof; alternatively, calcium sulfate; alternatively, calcium chloride; alternatively, calcium oxide; alternatively, magnesium sulfate; alternatively, sodium sulfate; alternatively, potassium sulfate; alternatively, magnesium perchlorate; alternatively, barium oxide; or alternatively, any combination thereof. In an aspect, the water absorption agent can be, comprise, or consist essentially of, an alumina, a silica, a silica gel, or any combination thereof; alternatively, gypsum, montmorillonite, or any combination thereof; alternatively, a molecular sieve, a zeolite, or any combination thereof; alternatively, an alumina; alternatively, a silica; alternatively, a silica gel; alternatively gypsum; alternatively, montmorillonite; alternatively a molecular sieve; or alternatively, a zeolite. In another aspect, the water absorption agent can comprise at least one molecular sieve. In an embodiment, the water absorption agent can comprise, or consist essentially of, be a 3 Å molecular sieve, a 4 Å molecular sieve, a 5 Å molecular sieve, a 10× molecular sieve, a 13× molecular sieve, or any combination thereof; alternatively, a 3 Å molecular sieve, a 4 Å molecular sieve, a 5 Å molecular sieve, or any combination thereof; alternatively, a 3 Å molecular sieve; alternatively, a 4 Å molecular sieve; alternatively, a 5 Å molecular sieve; alternatively a 10× molecular sieve; or alternatively, a 13× molecular sieve.

While not intending to be bound by theory, the selection of the molecular sieves utilized as the water absorption agent can be influenced by the coordinating compound, L, utilized to prepare the chromium(III) halide complex. Molecular sieves have pores of specific sizes and can absorb water (and other compounds) depending upon the size of the pore and the size of the particular compound. The pore sizes of a molecular sieves give rise to the selectivity of the molecular sieves for including water molecules (or other compounds) within the cavity of the molecular sieve, while excluding other compounds (e.g., the coordinating compound, L). Molecular sieves can potentially absorb the coordinating compound, L, and water, however, when proper selection of molecular sieve is made, water can be selectively absorbed in preference to the larger coordinating compound, L. In an aspect, a smaller pore molecular sieve, such as a 3 Å molecular sieve or a 4 Å molecular sieve, can be employed to provide a more selective absorption of water when small and large coordinating compounds are utilized. As the molecular sieve pore size increases, the chance that a smaller coordinating compound can also be absorbed by the molecular sieve increases. For example, larger-pore molecular sieves, such as a 10× or 13× molecular sieves can absorb smaller amines and ethers. However, it should be noted that while the smaller pore molecular sieves such as a 3 Å or 4 Å molecular sieve can be more efficient for water absorption agent when using small coordinating solvents, larger pore sized molecular sieves can still perform adequately in the process of forming a desired chromium(III) halide complex, $CrX_3.mL$, albeit the larger pore sized molecular sieves can require a longer time to produce the desired chromium(III) halide complex, $CrX_3.mL$.

In an aspect, the coordinating compound, L, utilized in the preparation of the chromium(III) halide complex, $CrX_3.mL$, can be, comprise, or consist essentially of, any coordinating compound that forms a stable or isolatable complex with a chromium(III) halide. Suitable coordinating compounds include sigma-donor compounds that contain at least one coordinating atom that can coordinate to the chromium(III) atom. In an embodiment, the coordinating atom of the coordinating compound can include, but is not limited to, oxygen, nitrogen, sulfur, phosphorus, or any combination thereof; alternatively, oxygen, nitrogen, sulfur, or any combination thereof; alternatively, oxygen, nitrogen, or any combination thereof; alternatively, oxygen, sulfur, or any combination thereof; alternatively, oxygen; alternatively, nitrogen; alternatively, sulfur; or alternatively, phosphorus. Unless otherwise specified, the coordinating compound can be unsubstituted or can be substituted. Substituents for a substituted coordinating compound are disclosed herein and can be utilized without limitation to describe a substituted coordinated compound.

In an aspect, the coordinating compound can be, comprise, or consist essentially of, a neutral coordinating compound. In another aspect, each coordinating compound (neutral or otherwise) independently can be, comprise, or consist essentially of, be an acyclic heteroatomic compound, or heterocyclic compound; alternatively, an acyclic heteroatomic compound; or alternatively, a heterocyclic compound. In an embodiment, each coordinating compound (neutral or otherwise, cyclic or acyclic) independently can be, comprise, or consist essentially of, an aliphatic heteroatomic compound or a heteroarene; alternatively, an aliphatic heteroatomic compound; or alternatively, a heteroarene. Suitable heteroatoms for the coordinating compound (neutral or otherwise, cyclic or acyclic, and/or aliphatic or aromatic) are described herein and can be utilized without limitation to further describe heteroatomic compound which can be utilized as the coordinating compound.

In an embodiment, each coordinating compound (neutral or otherwise) independently can be, comprise, or consist essentially of, an aliphatic acyclic heterocyclic compound, a substituted aliphatic acyclic heterocyclic compound, an aliphatic heterocyclic compound, a subtituted aliphatic heterocyclic compound, a heteroarene, or a substituted heteroarene. In some embodiments, each coordinating compound independently can be, comprise, or consist essentially of, an aliphatic acyclic heterocyclic compound or a substituted aliphatic acyclic heterocyclic compound; alternatively, an aliphatic heterocyclic compound or a substituted aliphatic heterocyclic compound; or alternatively, a heteroarene or a substituted heteroarene. In other embodiments, each coordinating compound independently can be, comprise, or consist essentially of, an aliphatic acyclic heterocyclic compound, an aliphatic heterocyclic compound, or a heteroarene; alternatively, an aliphatic acyclic heterocyclic compound; alternatively, an aliphatic heterocyclic compound; or alternatively, a heteroarene. In an embodiment, any aliphatic acyclic heterocyclic compound (neutral or otherwise, or substituted or unsubstituted) which can be, comprise, or consist essentially of, utilized as the coordinating compound can be, comprise, or consist essentially of, a $C_2$-$C_{60}$ aliphatic acyclic heterocyclic compound; alternatively, a $C_2$-$C_{45}$ aliphatic acyclic heterocyclic compound; alternatively, a $C_2$-$C_{30}$ aliphatic acyclic heterocyclic compound; or alternatively, a $C_2$-$C_{20}$ aliphatic acyclic heterocyclic compound; alternatively, a $C_2$-$C_{10}$ aliphatic acyclic heterocyclic compound; or alternatively, a $C_2$-$C_5$ aliphatic acyclic heterocyclic compound. In an embodiment, any aliphatic heterocyclic compound (neutral or otherwise, or substituted or unsubstituted) which can be utilized as the coordinating compound can be, comprise, or consist essentially of, a $C_3$-$C_{60}$ aliphatic heterocyclic compound; alternatively, a $C_3$-$C_{45}$ aliphatic heterocyclic compound; alternatively, a $C_3$-$C_{30}$ aliphatic heterocyclic compound; alternatively, a $C_3$-$C_{20}$ aliphatic heterocyclic compound; alternatively, a $C_3$-$C_{15}$ aliphatic heterocyclic compound; or alternatively, a $C_3$-$C_{10}$ aliphatic heterocyclic compound. In an embodiment, any heteroarene compound (neutral or otherwise, or substituted or unsubstituted) which can be utilized as the coordinating compound can be, comprise, or consist essentially of, a $C_4$-$C_{60}$ heteroarene; alternatively, a $C_4$-$C_{45}$ heteroarene; alternatively, a $C_4$-$C_{30}$ heteroarene; alternatively, a $C_4$-$C_{20}$ heteroarene; alternatively, a $C_4$-$C_{15}$ heteroarene; or alternatively, a $C_4$-$C_{10}$ heteroarene. Substituents for a substituted coordinating compound are disclosed herein and can be utilized without limitation to describe a substituted aliphatic acyclic heterocyclic compound, a substituted aliphatic heterocyclic compound, and/or a substituted heteroarene which can be utilized as a coordinating compound.

In an embodiment, each coordinating compound (neutral or otherwise) independently can be, comprise, or consist essentially of, an ether, a thioether, a nitrile, an amine, a phosphine, a phosphite or any combination thereof; an ether, a thioether, a nitrile, an amine, a phosphine, or any combination thereof alternatively, an ether; alternatively, a thioether; alternatively, a nitrile; alternatively, an amine; alternatively, a phosphine; or alternatively, a phosphite. In some embodiments, each coordinating compound (neutral or otherwise) independently can be, comprise, or consist essentially of, an acyclic ether, a substituted acyclic ether, a cyclic ether, a substituted cyclic ether, an acyclic thioether, a substituted acyclic thioether, a cyclic thioether, a substituted cyclic thioether, an aliphatic nitrile, a substituted aliphatic nitrile, an aromatic nitrile, a substituted aromatic nitrile, an acyclic amine, a substituted acyclic amine, a cyclic amine, a substituted cyclic amine, an acyclic phosphine, a substituted acyclic phosphine, a cyclic phosphine, a substituted cyclic phosphine, an acyclic phosphite, a substituted acyclic phosphite, a cyclic phosphite, a substituted cyclic phosphite, or any combination thereof; alternatively, an acyclic ether, a substituted acyclic ether, an acyclic thioether, a substituted acyclic thioether, an aliphatic nitrile, a substituted aliphatic nitrile, an acyclic amine, a substituted acyclic amine, an acyclic phosphine, a substituted acyclic phosphine, an acyclic phosphite, a substituted acyclic phosphite, or any combination thereof; alternatively, a cyclic ether, a substituted cyclic ether, a cyclic thioether, a substituted cyclic thioether, a cyclic amine, a substituted cyclic amine, a cyclic phosphine, a substituted cyclic phosphine, a cyclic phosphite, a substituted cyclic phosphite, or any combination thereof; alternatively, an acyclic ether, a substituted acyclic ether, a cyclic ether, or a substituted cyclic ether; alternatively, an acyclic thioether, a substituted acyclic thioether, a cyclic thioether, or a substituted cyclic thioether; alternatively, an aliphatic nitrile, a substituted aliphatic nitrile, an aromatic nitrile, or a substituted aromatic nitrile; alternatively, an acyclic amine, a substituted acyclic amine, a cyclic amine, or a substituted cyclic amine; alternatively, an acyclic phosphine, a substituted acyclic phosphine, a cyclic phosphine, or a substituted cyclic phosphine; or alternatively, an acyclic phosphite, a substituted acyclic phosphite, a cyclic phosphite, or a substituted cyclic phosphite. In other embodiments, each coordinating compound (neutral or otherwise) independently can be, comprise, or consist essentially of, an acyclic ether, a cyclic ether, an acyclic thioether, a cyclic thioether, an aliphatic nitrile, an aromatic nitrile, an acyclic amine, a cyclic amine, or any combination thereof; alternatively, an acyclic ether or a substituted acyclic ether; alternatively, a cyclic ether or a substituted cyclic ether; alternatively, an acyclic thioether or a substituted acyclic thioether; alternatively, a cyclic thioether or a substituted cyclic thioether; alternatively, an aliphatic nitrile or a substituted aliphatic nitrile; alternatively, an aromatic nitrile or a substituted aromatic nitrile; alternatively, an acyclic amine or a substituted acyclic amine; alternatively, a cyclic amine or a substituted cyclic amine; alternatively, an acyclic phosphine or a substituted acyclic phosphine; alternatively, a cyclic phosphine or a substituted cyclic phosphine; alternatively, an acyclic phosphite or a substituted acyclic phosphite; alternatively, a cyclic phosphite or a substituted cyclic phosphite; alternatively, an acyclic ether; alternatively, a cyclic ether; alternatively, an acyclic thioether; alternatively, a cyclic thioether; alternatively, an aliphatic nitrile; alternatively, an aromatic nitrile; alternatively, an acyclic amine; alternatively, a cyclic amine; alternatively, an acyclic phosphine; alternatively, a cyclic phosphine; alternatively, an acyclic phosphite; or alternatively, a cyclic phosphite. In an embodiment, the cyclic ether (substituted or unsubstituted), cyclic thioether (substituted or unsubstituted), cyclic amine (substituted or unsubstituted), cyclic phosphine (substituted or unsubstituted), and/or cyclic phosphite (substituted or unsubstituted) can be aliphatic or aromatic; alternatively, aliphatic; or alternatively, aromatic. Substituents (also referred to as non-hydrogen substituents or non-hydrogen substituent groups) are independently disclosed herein and can be utilized without limitation to further describe a substituted ether (acyclic, cyclic, aliphatic or aromatic), a substituted thioether (acyclic, cyclic, aliphatic or aromatic), a substituted nitrile (aliphatic or aromatic), a substituted amine (acyclic, cyclic, aliphatic or aromatic), a substituted phosphine (acyclic, cyclic, aliphatic or aromatic), and/or a substituted phosphite (acyclic, cyclic, aliphatic or aromatic) which can be utilized as a coordinating compound.

In an embodiment, a nitrile utilized as the coordinating compound can have the formula $R^1C\equiv N$. In an embodiment, an ether utilized as the coordinating compound can have the formula $R^2-O-R^3$. In an embodiment, a thioether utilized as the coordinating compound can have the formula $R^4-S-R^5$. In an embodiment, an amine utilized as the coordinating compound can have the formula $NR^6R^7R^8$, $NHR^6R^7$, or $NH_2R^6$; alternatively, $NR^6R^7R^8$; alternatively, $NHR^6R^7$; or alternatively, $NH_2R^6$. In an embodiment, a phosphine utilized as the coordinating compound can have the formula $PR^9R^{10}R^{11}$, $PHR^9R^{10}$, or $PH_2R^9$; alternatively, $PR^9R^{10}R^{11}$; alternatively, $PHR^9R^{10}$; or alternatively, $PH_2R^9$. In an embodiment, an phosphite utilized as the coordinating compound can have the formula $P(OR^{12})(OR^{13})(OR^{14})$ or $PH(O)(OR^{12})(OR^{13})$; alternatively, $P(OR^{12})(OR^{13})(OR^{14})$; or alternatively, $PH(O)(OR^{12})(OR^{13})$. In an embodiment, each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ independently can be a $C_1$-$C_{20}$ organyl group; alternatively, a $C_1$-$C_{10}$ organyl group; or alternatively, a $C_1$-$C_{20}$ organyl group. In some embodiments, each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ independently can be an $C_1$-$C_{20}$ hydrocarbyl group or a $C_1$-$C_{20}$ substituted hydrocarbyl group; alternatively, $C_1$-$C_{20}$ hydrocarbyl group; or alternatively, a $C_1$-$C_{20}$ substituted hydrocarbyl group. In other embodiments, each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ independently can be an $C_1$-$C_{10}$ hydrocarbyl group or a $C_1$-$C_{10}$ substituted hydrocarbyl group; alternatively, $C_1$-$C_{10}$ hydrocarbyl group; or alternatively, a $C_1$-$C_{10}$ substituted hydrocarbyl group. In yet other embodiments, each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ independently can be an $C_1$-$C_5$ hydrocarbyl group or a $C_1$-$C_5$ substituted hydrocarbyl group; alternatively, $C_1$-$C_5$ hydrocarbyl group; or alternatively, a $C_1$-$C_5$ substituted hydrocarbyl group.

In an embodiment, each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group, or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. Generally, the alkyl groups, substituted alkyl groups, cycloalkyl groups, substituted cycloalkyl groups, aryl groups, a substituted aryl groups, aralkyl groups, and substituted aralkyl groups which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ can have the same number of carbon atoms as organyl group or hydrocarbyl group of which they are a member.

In an embodiment, the alkyl group (substituted or unsubstituted) which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ can be a $C_1$-$C_{20}$ alkyl group (substituted or unsubstituted); alternatively, a $C_1$-$C_{10}$ alkyl group (substituted or unsubstituted); or alternatively, a $C_1$-$C_5$ alkyl group (substituted or unsubstituted). In some embodiments, each alkyl group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In other embodiments, each alkyl group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a methyl group, an ethyl group, a n-propyl group, an iso-propyl group, a n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group. In an embodiment, each substituent of a substituted alkyl group independently can be a halide or hydrocarboxy group; alternatively, a halide; or alternatively a hydrocarboxy group.

In an embodiment, the cycloalkyl group (substituted or unsubstituted) which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ can be a $C_4$-$C_{20}$ cycloalkyl group (substituted or unsubstituted); alternatively, a $C_4$-$C_{15}$ cycloalkyl group (substituted or unsubstituted); or alternatively, a $C_4$-$C_{10}$ cycloalkyl group (substituted or unsubstituted). In some embodiments, each group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group; alternatively, a cyclopentyl group, a substituted cyclopentyl group, a cyclohexyl group, or a substituted cyclohexyl group. In other embodiments, each group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group, or a substituted cyclooctyl group; alternatively, a cyclopentyl group; alternatively, a substituted cyclopentyl group; a cyclohexyl group; or alternatively, a substituted cyclohexyl group. In an embodiment, each substituent of a substituted cycloalkyl group independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

In an embodiment, the aryl group (substituted or unsubstituted) which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ can be a $C_6$-$C_{20}$ aryl group (substituted or unsubstituted); alternatively, a $C_6$-$C_{15}$ aryl group (substituted or unsubstituted); or alternatively, a $C_6$-$C_{10}$ aryl group (substituted or unsubstituted). In some embodiments, each group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a phenyl group, a substituted phenyl group, a naphthyl group, or a substituted naphthyl group; alternatively, a phenyl group or a substituted phenyl group; alternatively, a naphthyl group or a substituted naphthyl group; alternatively, a phenyl group or a naphthyl group; or alternatively, a substituted phenyl group or a substituted naphthyl group. In an embodiment, each substituted phenyl group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a 2-substituted phenyl group, a 3-substituted phenyl group, a 4-substituted phenyl group, a 2,4-disubstituted phenyl group, a 2,6-disubstituted phenyl group, 3,5-disubstituted phenyl group, or a 2,4,6-trisubstituted phenyl group. In other embodiments, each substituted phenyl group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, 3,5-disubstituted phenyl group; or alternatively, a 2,4,6-trisubstituted phenyl group. In an embodiment, each substituent of a substituted aryl group independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

In some embodiments, the aralkyl group (substituted or unsubstituted) which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ can be a $C_7$-$C_{20}$ aralkyl group (substituted or unsubstituted); alternatively, a $C_7$-$C_{15}$ aralkyl group (substituted or unsubstituted); or alternatively, a $C_7$-$C_{10}$ aralkyl group (substituted or unsubstituted). In some embodiments, each group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a benzyl group or a substituted benzyl group; alternatively, a benzyl group, or alternatively, a substituted benzyl group. In an embodiment, each substituent of a substituted aralkyl group independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

Halide, hydrocarbyl group, and hydrocarboxy group substituents (also referred to as non-hydrogen substituents or non-hydrogen substituent groups) are independently disclosed herein. These substituent groups can be utilized without limitation to further describe any substituted $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ group described herein.

In an embodiment, any ether and/or acyclic ether (substituted or unsubstituted), which can be utilized as the coordinating compound, can be, comprise, or consist essentially of, a $C_2$-$C_{40}$ ether and/or acyclic ether; alternatively, a $C_2$-$C_{30}$ ether and/or acyclic ether; alternatively, a $C_2$-$C_{20}$ ether and/or acyclic ether; alternatively, a $C_2$-$C_{15}$ ether and/or acyclic ether; or alternatively, a $C_2$-$C_{10}$ ether and/or acyclic ether. In an embodiment, any cyclic ether (substituted or unsubstituted, and/or aliphatic or aromatic), which can be utilized as the coordinating compound, can be, comprise, or consist essentially of, a $C_3$-$C_{40}$ cyclic ether; alternatively, a $C_4$-$C_{30}$ cyclic ether; alternatively, a $C_4$-$C_{20}$ cyclic ether; alternatively, a $C_4$-$C_{15}$ cyclic ether; or alternatively, a $C_4$-$C_{10}$ cyclic ether.

In an aspect of this disclosure, each coordinating compound can independently be dihydrocarbyl ether or a substituted dihydrocarbyl ether; or alternatively, a dihydrocarbyl ether. Hydrocarbyl groups (substituted or substituted) are generally defined within the present disclosure as non-hydrogen substituent(s) for the substituted cycloalkyl group, substituted aromatic group, substituted aryl group, or substituted aralkyl group which can be utilized as $R^1$ of the nitrile having the formula $R^1C\equiv N$, $R^2$ and $R^3$ of the ether having formula $R^2$—O—$R^3$, $R^4$ and $R^5$ having the formula $R^4$—S—$R^5$, $R^6$, $R^7$, and $R^8$ of the amine having the formula $NR^6R^7R^8$, $NHR^6R^7$, or $NH_2R^6$, $R^9$, $R^{10}$, and $R^{11}$ of the phosphine having the formula $PR^9R^{10}R^{11}$, $PHR^9R^{10}$, or $PH_2R^9$, and $R^{12}$, $R^{13}$, and $R^{14}$ of the phosphite having the formula $P(OR^{12})(OR^{13})(OR^{14})$ or $PH(O)(OR^{12})(OR^{13})$. These hydrocarbyl substituent groups (substituted or substituted) can be utilized without limitation as hydrocarbyl groups of the dihydrocarbyl ethers (substituted or unsubstituted) which can be utilized as the coordinating compound.

In a non-limiting embodiment, each coordinating compound independently can be dimethyl ether, diethyl ether, dipropyl ether, dibutyl ether, methyl ethyl ether, methyl propyl ether, methyl butyl ether, or any combination thereof; alternatively, dimethyl ether; alternatively, diethyl ether; alternatively, dipropyl ether; alternatively, dibutyl ether; alternatively, methyl ethyl ether; alternatively, methyl propyl ether; or alternatively, methyl butyl ether. In another non-limiting embodiment, each coordinating compound independently can be, comprise, or consist essentially of, diphenyl ether, a substituted diphenyl ether, ditolyl ether, a substituted ditolyl ether, or any combination thereof; alternatively, diphenyl ether, ditolyl ether, or any combination thereof. In an embodiment, each coordinating compound independently can be, comprise, or consist essentially of, diphenyl ether; alternatively, a substituted diphenyl ether; alternatively, ditolyl ether; or alternatively, a substituted ditolyl ether.

In a non-limiting embodiment, each coordinating compound independently can be, comprise, or consist essentially of, tetrahydrofuran, a substituted tetrahydrofuran, 2,3-dihydrofuran, a substituted 2,3-dihydrofuran, 2,5-dihydrofuran, a substituted 2,5-dihydrofuran, or a combination thereof; alternatively, tetrahydrofuran, 2,3-dihydrofuran, 2,5-dihydrofuran, or a combination thereof; alternatively tetrahydrofuran; alternatively, a substituted tetrahydrofuran; 2,3-dihydrofuran; alternatively, a substituted 2,3-dihydrofuran; alternatively, 2,5-dihydrofuran; or alternatively, a substituted 2,5-dihydrofuran. In another non-limiting embodiment, each coordinating compound independently can be, comprise, or consist essentially of, tetrahydrofuran, a 2-substituted tetrahydrofuran, a 3-substituted tetrahydrofuran, or any combination thereof; alternatively, tetrahydrofuran; alternatively, a 2-substituted tetrahydrofuran; or alternatively, a 3-substituted tetrahydrofuran. In further non-limiting embodiments, each coordinating compound independently can be, comprise, or consist essentially of, tetrahydrofuran, a 2-alkyl substituted tetrahydrofuran, a 3-alkyl substituted tetrahydrofuran, or any combination thereof; alternatively, tetrahydrofuran; alternatively, a 2-alkyl substituted tetrahydrofuran; or alternatively, a 3-alkyl substituted tetrahydrofuran.

In a non-limiting embodiment, each coordinating compound independently can be, comprise, or consist essentially of, furan, a substituted furan, benzofuran, a substituted benzofuran, isobenzofuran, a substituted isobenzofuran, dibenzofuran, a substituted dibenzofuran, or any combination thereof. In another non-limiting embodiment, each coordinating compound independently can be, comprise, or consist essentially of, furan, benzofuran, isobenzofuran, dibenzofuran, or any combination thereof; alternatively, furan; alternatively, a substituted furan; alternatively, benzofuran; alternatively, a substituted benzofuran; alternatively, isobenzofuran; alternatively, a substituted isobenzofuran; alternatively, dibenzofuran; alternatively, a substituted dibenzofuran.

In a non-limiting embodiment, each coordinating compound independently can be, comprise, or consist essentially of, tetrahydrofuran, a substituted tetrahydrofuran, oxane, a substituted oxane, 3,4-dihydro-2H-pyran, a substituted 3,4-dihydro-2H-pyran, 3,6-dihydro-2H-pyran, a substituted 3,6-dihydro-2H-pyran, 2H-pyran, a substituted 2H-pyran, 4H-pyran, a substituted 4H-pyran, 1,3-dioxane, a substituted 1,3-dioxane, 1,4-dioxane, a substituted 1,4-dioxane, morpholine, a substituted morpholine, an N-substituted morpholine, a substituted N-substituted morpholine, or any combination thereof; alternatively, tetrahydrofuran, oxane, 3,4-dihydro-2H-pyran, 3,6-dihydro-2H-pyran, 2H-pyran, 4H-pyran, 1,3-dioxane, 1,4-dioxane, morpholine, an N-substituted morpholine, or any combination thereof. In another non-limiting embodiment, each coordinating compound independently can be, comprise, or consist essentially of, tetrahydrofuran, oxane, 1,3-dioxane, 1,4-dioxane, or any combination thereof. In further non-limiting embodiment, each coordinating compound independently can be, comprise, or consist essentially of, oxane; alternatively, a substituted oxane; alternatively, 3,4-dihydro-2H-pyran; alternatively, a substituted 3,4-dihydro-2H-pyran; alternatively, 3,6-dihydro-2H-pyran; alternatively, a substituted 3,6-dihydro-2H-pyran; alternatively, 2H-pyran; alternatively, a substituted 2H-pyran; alternatively, 4H-pyran; alternatively, a substituted 4H-pyran; alternatively, 1,3-dioxane; alternatively, a substituted 1,3-dioxane; alternatively, 1,4-dioxane; alternatively, a substituted 1,4-dioxane; alternatively, morpholine; alternatively, a substituted morpholine; alternatively, an N-substituted morpholine; or alternatively, a substituted N-substituted morpholine.

General substituents (also referred to as non-hydrogen substituents or non-hydrogen substituent groups) are independently disclosed herein. These substituent groups can be utilized without limitation to further describe any substituted ether, substituted acyclic ether, substituted cyclic ether (aliphatic or aromatic), substituted diphenyl ethers, substituted ditolyl ethers, substituted tetrahydrofurans, alkyl substituted tetrahydrofurans, substituted furans, benzofurans, isobenzofurans, dibenzofurans, substituted oxanes, substituted 3,4-dihydro-2H-pyrans, substituted 3,6-dihydro-2H-pyrans, substituted 4H-pyrans, substituted 1,3-dioxanes, substituted 1,4-dioxanes, substituted morpholines, N-hydrocarbyl morpholines, and/or substituted N-hydrocarbyl morpholines which can be utilized as the coordinating compound.

In an embodiment, any thioether and/or acyclic thioether (substituted or unsubstituted), which can be utilized as the coordinating compound, can be, comprise, or consist essentially of, a $C_2$-$C_{40}$ thioether and/or acyclic thioether; alternatively, a $C_2$-$C_{30}$ thioether and/or acyclic thioether; alternatively, a $C_2$-$C_{20}$ thioether and/or acyclic thioether; alternatively, a $C_2$-$C_{15}$ thioether and/or acyclic thioether; or alternatively, a $C_2$-$C_{10}$ thioether and/or acyclic thioether. In an embodiment, any cyclic thioether (substituted or unsubstituted, and/or aliphatic or aromatic), which can be utilized as the coordinating compound, can be, comprise, or consist essentially of, a $C_3$-$C_{40}$ cyclic thioether; alternatively, a $C_4$-$C_{30}$ cyclic thioether; alternatively, a $C_4$-$C_{20}$ cyclic thioether; alternatively, a $C_4$-$C_{15}$ cyclic thioether; or alternatively, a $C_4$-$C_{10}$ cyclic thioether.

In an aspect of this disclosure, each coordinating compound can independently be dihydrocarbyl thioether or a substituted dihydrocarbyl thioether; or alternatively, a dihydrocarbyl thioether. Hydrocarbyl groups (substituted or substituted) are generally defined within the present disclosure as non-hydrogen substituent(s) for the substituted cycloalkyl group, substituted aromatic group, substituted aryl group, or substituted aralkyl group which can be utilized as $R^1$ of the nitrile having the formula $R^1C\equiv N$, $R^2$ and $R^3$ of the ether having formula $R^2$—O—$R^3$, $R^4$ and $R^5$ having the formula $R^4$—S—$R^5$, $R^6$, $R^7$, and $R^8$ of the amine having the formula $NR^6R^7R^8$, $NHR^6R^7$, or $NH_2R^6$, $R^9$, $R^{10}$, and $R^{11}$ of the phosphine having the formula $PR^9R_{10}$, $PHR^9R^{10}$ and $R^{14}$ of the phosphite having the formula $P(OR^{12})(OR^{13})(OR^{14})$ or $PH(O)(OR^{12})(OR^{13})$. These hydrocarbyl substituent groups (substituted or substituted) can be utilized without limitation as hydrocarbyl groups of the dihydrocarbyl thioethers (substituted or unsubstituted) which can be utilized as the coordinating compound.

In a non-limiting embodiment, each coordinating compound independently can be, comprise, or consist essentially of, dimethyl thioether, diethyl thioether, dipropyl thioether, dibutyl thioether, methyl ethyl thioether, methyl propyl thioether, methyl butyl thioether, or any combination thereof. In another non-limiting embodiment, the neutral ligand(s) can be, comprise, or consist essentially of, dimethyl thioether; alternatively, diethyl thioether; alternatively, dipropyl thioether; alternatively, dibutyl thioether; alternatively, methyl ethyl thioether; alternatively, methyl propyl thioether; alternatively, or methyl butyl thioether. In a non-limiting embodiment, each coordinating compound independently can be, comprise, or consist essentially of, diphenyl thioether, a substituted diphenyl thioether, ditolyl thioether, a substituted ditolyl thioether, or any combination thereof; alternatively, diphenyl thioether, ditolyl thioether, or any combination thereof. In an embodiment, each coordinating compound independently can be, comprise, or consist essentially of, diphenyl thioether; alternatively, a substituted diphenyl thioether; alternatively, ditolyl thioether; or alternatively, a substituted ditolyl thioether.

In a non-limiting embodiment, each coordinating compound independently can be, comprise, or consist essentially of, thiophene, a substituted thiophene, benzothiophene, a substituted benzothiophene, or any combination thereof. In another non-limiting embodiment, each coordinating compound independently can be, comprise, or consist essentially of, thiophene, benzothiophene, or any combination thereof; alternatively, thiophene; alternatively, a substituted thiophene; alternatively, benzothiophene; or alternatively, a substituted benzothiophene.

In a non-limiting embodiment, each coordinating compound independently can be, comprise, or consist essentially of, tetrahydrothiophene, a substituted tetrahydrothiophene, thiane, a substituted thiane, or any combination thereof. In another non-limiting embodiment, each coordinating compound independently can be, comprise, or consist essentially of, tetrahydrothiophene, thiane, or a combination thereof; alternatively, tetrahydrothiophene; alternatively, a substituted tetrahydrothiophene; alternatively, thiane; or alternatively, a substituted thiane.

General substituents (also referred to as non-hydrogen substituents or non-hydrogen substituent groups) are independently disclosed herein. These substituent groups can be utilized without limitation to further describe any substituted thioether, substituted acyclic thioether, substituted cyclic thioether, substituted diphenyl thiol ethers, substituted ditolyl thioethers, substituted thiophenes, and/or substituted benzothiophenes which can be utilized as the coordinating compound.

In an embodiment, any nitrile (substituted or unsubstituted), which can be utilized as the coordinating compound, can be, comprise, or consist essentially of, a $C_2$-$C_{20}$ aliphatic nitrile; alternatively, a $C_2$-$C_{15}$ aliphatic nitrile; alternatively, a $C_2$-$C_{10}$ aliphatic nitrile; or alternatively, a $C_2$-$C_5$ aliphatic nitrile. In an embodiment, any nitrile (substituted or unsubstituted), which can be, comprise, or consist essentially of, utilized as the coordinating compound, can be, comprise, or consist essentially of, a $C_6$-$C_{20}$ aromatic nitrile; alternatively, a $C_6$-$C_{15}$ aromatic nitrile; or alternatively, a $C_6$-$C_{10}$ aromatic nitrile.

In an aspect of this disclosure, each coordinating compound can independently be hydrocarbyl nitrile or a substituted hydrocarbyl nitrile; or alternatively, a hydrocarbyl nitrile. Hydrocarbyl groups (substituted or substituted) are generally defined within the present disclosure as non-hydrogen substituent(s) for the substituted cycloalkyl group, substituted aromatic group, substituted aryl group, or substituted aralkyl group which can be utilized as $R^1$ of the nitrile having the formula $R^1C\equiv N$, $R^2$ and $R^3$ of the ether having formula $R^2$—O—$R^3$, $R^4$ and $R^5$ having the formula $R^4$—S—$R^5$, $R^6$, $R^7$, and $R^8$ of the amine having the formula $NR^6R^7R^8$, $NHR^6R^7$, or $NH_2R^6$, $R^9$, $R^{19}$, and $R^{11}$ of the phosphine having the formula $PR^9R^{10}R^{11}$, $PHR^9R^{10}$, or $PH_2R^9$, and $R^{12}$, $R^{13}$, and $R^{14}$ of the phosphite having the formula $P(OR^{12})(OR^{13})(OR^{14})$ or $PH(O)(OR^{12})(OR^{13})$. These hydrocarbyl substituent groups (substituted or substituted) can be utilized without limitation as hydrocarbyl groups of the hydrocarbyl nitrile (substituted or unsubstituted) which can be utilized as the coordinating compound.

In a non-limiting embodiment, each coordinating compound independently can be, comprise, or consist essentially of, acetonitrile, propionitrile, butyronitrile, or any combination thereof. In another non-limiting embodiment, each coordinating compound independently can be, comprise, or consist essentially of, acetonitrile; alternatively, propionitrile; or alternatively, butyronitrile.

In a non-limiting embodiment, each coordinating compound independently can be, comprise, or consist essentially of, benzonitrile, a substituted benzonitrile, or any combination thereof; alternatively, benzonitrile; or alternatively, a substituted benzonitrile. In another non-limiting embodiment, each coordinating compound independently can be, comprise, or consist essentially of, benzonitrile, a 2-substituted benzonitrile, a 3-substituted benzonitrile, a 4-substituted benzonitrile, a 2,4-substituted benzonitrile, a 3,5-disubstituted, a 2,4,6-trisubstituted benzonitrile, or any combination thereof; alternatively, a 2-substituted benzonitrile, a 4-substituted benzonitrile, a 2,4-substituted benzonitrile, a 2,4,6-trisubstituted benzonitrile, or any combination thereof alternatively, a 2-substituted benzonitrile; alternatively, a 3-substituted benzonitrile; alternatively, a 4-substituted benzonitrile; alternatively, a 2,4-substituted benzonitrile; alternatively, a 3,5-disubstituted; or alternatively, a 2,4,6-trisubstituted benzonitrile. In yet other embodiments, each coordinating compound independently can be, comprise, or consist essentially of, benzonitrile, a 2-alkyl benzonitrile, a 3-alkyl benzonitrile, a 4-methylbenzonitrile, a 2,4-alkyl benzonitrile, a 3,5-dialkyl, a 2,4,6-trialkyl benzonitrile, or any combination thereof; alternatively, a 2-alkyl benzonitrile, a 4-alkyl benzonitrile, a 2,4-alkyl benzonitrile, a 2,4,6-trialkyl benzonitrile, or any combination thereof alternatively, a 2-alkyl benzonitrile; alternatively, a 3-alkyl benzonitrile; alternatively, a 4-alkyl benzonitrile; alternatively, a 2,4-alkyl benzonitrile; alternatively, a 3,5-dialkyl; or alternatively, a 2,4,6-trialkyl benzonitrile.

General substituents (also referred to as non-hydrogen substituents or non-hydrogen substituent groups) are independently disclosed herein. These substituent groups can be utilized without limitation to further describe any substituted aliphatic nitrile, substituted aromatic nitrile, substituted benzonitriles, and/or alkyl substituted benzonitriles which can be utilized as the coordinating compound.

In an embodiment, any amine and/or acyclic amine (substituted or unsubstituted), which can be utilized as the coordinating compound, can be, comprise, or consist essentially of, a $C_1$-$C_{60}$ amine and/or acyclic amine; alternatively, a $C_1$-$C_{45}$ amine and/or acyclic amine; alternatively, a $C_1$-$C_{30}$ amine and/or acyclic amine; alternatively, a $C_1$-$C_{20}$ amine and/or acyclic amine; alternatively, a $C_1$-$C_{15}$ amine and/or acyclic amine; or alternatively, a $C_1$-$C_{10}$ amine and/or acyclic amine. In an embodiment, any cyclic amine (substituted or unsubstituted, and/or aliphatic or aromatic), which can be utilized as the coordinating compound, can be, comprise, or consist essentially of, a $C_3$-$C_{60}$ cyclic amine; alternatively, a $C_3$-$C_{45}$ cyclic amine; alternatively, a $C_3$-$C_{30}$ cyclic amine; alternatively, a $C_4$-$C_{20}$ cyclic amine; or alternatively, a $C_4$-$C_{15}$ cyclic amine.

In an aspect of this disclosure, each coordinating compound can independently be a hydro-carbylamine, a substituted hydrocarbyl amine, a dihydrocarbylamine, a substituted dihydrocarbylamine, a trihydrocarbylamine, a substituted trihydrocarbylamine, any combination thereof; a hydrocarbylamine, a dihydrocarbylamine, a trihydrocarbylamine, or any combination thereof; alternatively, a hydrocarbyl-amine or a substituted hydrocarbylamine; alternatively, a dihydrocarbylamine or a substituted dihydro-carbylamine; alternatively, a trihydrocarbylamine or a substituted trihydrocarbylamine; alternatively, a hydrocarbylamine; alternatively, a substituted hydrocarbylamine; alternatively, a dihydrocarbylamine; alternatively, a substituted dihydrocarbylamine; alternatively, a trihydrocarbylamine; or alternatively, a substituted trihydrocarbylamine. Hydrocarbyl groups (substituted or substituted) are generally defined within the present disclosure as non-hydrogen substituent(s) for the substituted cycloalkyl group, substituted aromatic group, substituted aryl group, or substituted aralkyl group which can be utilized as $R^1$ of the nitrile having the formula $R^1C\equiv N$, $R^2$ and $R^3$ of the ether having formula $R^2$—O—$R^3$, $R^4$ and $R^5$ having the formula $R^4$—S—$R^5$, $R^6$, $R^7$, and $R^8$ of the amine having the formula $NR^6R^7R^8$, $NHR^6R^7$, or $NH_2R^6$, $R^9$, $R^{10}$, and $R^{11}$ of the phosphine having the formula $PR^9R^{10}R^{11}$, $PHR^9R^{10}$, or $PH_2R^9$, and $R^{12}$, $R^{13}$, and $R^{14}$ of the phosphite having the formula $P(OR^{12})(OR^{13})(OR^{14})$ or $PH(O)(OR^{12})(OR^{13})$. These hydrocarbyl substituent groups (substituted or substituted) can be utilized without limitation as the hydrocarbyl groups of the hydrocarbylamine (substituted or unsubstituted), a dihydrocarbylamine (substituted or unsubstituted), a trihydrocarbylamine (substituted or unsubstituted) which can be utilized as the coordinating compound.

In a non-limiting embodiment, each coordinating compound independently can be, comprise, or consist essentially of, methyl amine, ethyl amine, propyl amine, butyl amine, dimethyl amine, diethyl amine, dipropyl amine, dibutylamine, trimethyl amine, triethyl amine, tripropyl amine, tributyl amine, or any combination thereof. In another non-limiting embodiment, each coordinating compound independently can be, comprise, or consist essentially of, methyl amine, ethyl amine, propyl amine, butyl amine, or any combination thereof; alternatively, dimethyl amine, diethyl amine, dipropyl amine, dibutylamine, or any combination thereof; or alternatively, trimethyl amine, triethyl amine, tripropyl amine, tributyl amine, or any combination thereof. In yet another non-limiting embodiment, each coordinating compound can be, comprise, or consist essentially of, methyl amine; alternatively, ethyl amine; alternatively, propyl amine; alternatively, butyl amine; alternatively, dimethyl amine; alternatively, diethyl amine; alternatively, dipropyl amine; alternatively, dibutylamine; alternatively, trimethyl amine; alternatively, triethyl amine; alternatively, tripropyl amine; or alternatively, tributyl amine.

In a non-limiting embodiment, each coordinating compound independently can be, comprise, or consist essentially of, aniline, a substituted aniline, a N-hydrocarbyl aniline, a substituted N-hydrocarbyl aniline, a N,N-dihydrocarbyl aniline, a substituted N,N-dihydrocarbylaniline, diphenylamine, a di(substituted phenyl)amine, a N-hydrocarbyl diphenylamine, a N-hydrocarbyl di(substituted phenyl) amine, triphenylamine, a substituted triphenylamine, or any combination thereof. In another non-limiting embodiment, each coordinating compound independently can be, comprise, or consist essentially of, aniline, a substituted aniline, a N-hydrocarbyl aniline, a substituted N-hydrocarbyl aniline, a N,N-dihydrocarbyl aniline, a substituted N,N-dihydrocarbyl aniline, or any combination thereof; alternatively, diphenylamine, a di(substituted phenyl)amine, a N-hydrocarbyl diphenylamine, a N-hydrocarbyl di(substitute phenyl)amine, or any combination thereof; or alternatively, triphenylamine, a substituted triphenylamine, or any combination thereof. In yet another non-limiting embodiment, each coordinating compound can be, comprise, or consist essentially of, aniline; alternatively, a substituted aniline; alternatively, a N-hydrocarbyl aniline; alternatively, a substituted N-hydrocarbyl aniline; alternatively, a N,N-dihydrocarbyl aniline; alternatively, a substituted N,N-dihydrocarbyl aniline; alternatively, diphenylamine; alternatively, a di(substituted phenyl)amine; alternatively, a N-hydrocarbyl diphenylamine; alternatively, a N-hydrocarbyl di(substitute phenyl)amine; alternatively, triphenylamine; or alternatively, a substituted triphenylamine. In some non-limiting embodiments, each coordinating compound independently can be, comprise, or consist essentially of, aniline, tolylamine, xylylamine, diphenylamine, ditolylamine, triphenylamine, or any combination thereof. In other non-limiting embodiments, each coordinating compound can aniline; alternatively, tolylamine; alternatively, xylylamine; alternatively, diphenylamine; alternatively, ditolylamine; or alternatively, triphenylamine.

In a non-limiting embodiment, each coordinating compound independently can be, comprise, or consist essentially of, pyrrole, a substituted pyrrole, indole, a substituted indole, pyridine, a substituted pyridine, quinoline, a substituted quinoline, or any combination thereof. In another non-limiting embodiment, each coordinating compound independently can be, comprise, or consist essentially of, pyrrole, a substituted pyrrole, or any combination thereof; alternatively, indole, a substituted indole, or any combination thereof; alternatively, pyridine, a substituted pyridine, or any combination thereof; or alternatively, quinoline, a substituted quinoline, or any combination thereof; alternatively, pyrrole, indole, pyridine, quinoline, or any combination thereof. In yet another non-limiting embodiment, each coordinating compound independently can be, comprise, or consist essentially of, pyrrole; alternatively, a substituted pyrrole; alternatively, indole; alternatively, a substituted indole; alternatively, pyridine; alternatively, a substituted pyridine; alternatively, quinoline; or alternatively, an substituted quinoline.

Substituent groups and hydrocarbyl groups are generally defined within the present disclosure as non-hydrogen substituent(s) for the substituted cycloalkyl group, substituted aromatic group, substituted aryl group, or substituted aralkyl group which can be utilized as $R^1$ of the nitrile having the formula $R^1C \equiv N$, $R^2$ and $R^3$ of the ether having formula $R^2-O-R^3$, $R^4$ and $R^5$ having the formula $R^4-S-R^5$, $R^6$, $R^7$, and $R^8$ of the amine having the formula $NR^6R^7R^8$, $NHR^6R^7$, or $NH_2R^6$, $R^9$, $R^{10}$, and $R^{11}$ of the phosphine having the formula $PR^9R^{10}R^{11}$, $PHR^9R^{10}$ or $PH_2R^9$, and $R^{12}$, $R^{13}$, and $R^{14}$ of the phosphite having the formula $P(OR^{12})(OR^{13})(OR^{14})$ or $PH(O)(OR^{12})(OR^{13})$. These substituent groups can be utilized without limitation to further describe any substituted amine, substituted acyclic amine, substituted cyclic amine, N-hydrocarbyl aniline (substituted or unsubstituted), N,N-dihydrocarbyl aniline (substituted or unsubstituted), substituted diphenylamines, substituted triphenylamines, substituted pyrroles, substituted indoles, substituted pyridines, and/or substituted quinolines which can be utilized as the coordinating compound.

In an aspect, the neutral ligand(s) of any transition metal complex (general or specific) or transition metal precursor (general or specific) described herein, independently can be, comprise, or consist essentially of, a pyrrole compound. In an embodiment, the pyrrole compound which can be utilized as a coordinating compound can have Formula P1.

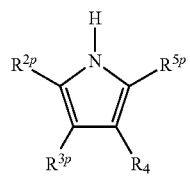

P1

In Formula P1, $R^{2p}$, $R^{3p}$, $R^{4p}$, and $R^{5p}$ independently can be hydrogen atom or a substituent group. In an embodiment where the pyrrole has Formula P1, $R^{3p}$, $R^{4p}$, and $R^{5p}$ can be hydrogen and $R^{2p}$ can be any non-hydrogen pyrrole substituent described herein; or alternatively, $R^{2p}$, $R^{4p}$, and $R^{5p}$ can be hydrogen and $R^{3p}$ can be any non-hydrogen pyrrole substituent described herein. In an embodiment where the pyrrole has Formula P1, $R^{3p}$ and $R^{4p}$ can be hydrogen and $R^{2p}$ and $R^{5p}$ independently can be any non-hydrogen pyrrole substituent described herein; alternatively, $R^{2p}$ and $R^{5p}$ can be hydrogen and $R^{3p}$ and $R^{4p}$ independently can be any non-hydrogen pyrrole substituent described herein; or alternatively, $R^{2p}$ and $R^{4p}$ can be hydrogen and $R^{3p}$ and $R^{5p}$ independently can be any non-hydrogen pyrrole substituent described herein. In an embodiment where the pyrrole has Formula P1, $R^{5p}$ can be hydrogen and $R^{2p}$, $R^{3p}$, and $R^{4p}$ independently can be any non-hydrogen pyrrole substituent described herein; or alternatively, $R^{4p}$ can be hydrogen and $R^{2p}$, $R^{3p}$, and $R^{5p}$ can be any non-hydrogen pyrrole substituent described herein. In other embodiments, $R^{2p}$, $R^{3p}$, $R^{4p}$, and $R^{5p}$ independently can be any non-hydrogen pyrrole substituent described herein.

In an embodiment, the pyrrole compound which can be utilized as a coordinating compound can have Formula P2, Formula P3, Formula P4, Formula P5, or a combination thereof; alternatively, Formula P2, Formula P3, Formula P4, or any combination thereof; alternatively, Formula P2; alternatively, Formula P3; alternatively, Formula P4; or alternatively, Formula P5.

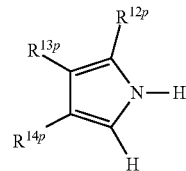

P2

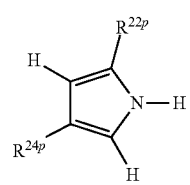

P3

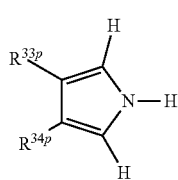

P4

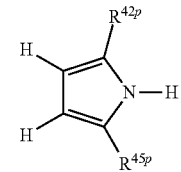

P5

In pyrrole Formulas P2, P3, P4, and P5, $R^{12p}$, $R^{13p}$, $R^{14p}$, $R^{22p}$, $R^{24p}$, $R^{33p}$, $R^{34p}$, $R^{42p}$, and $R^{45p}$ independently can be any non-hydrogen pyrrole substituent described herein.

In an embodiment, each non-hydrogen substituent group which can be utilized as $R^{2p}$, $R^{3p}$, $R^{4p}$, and $R^{5p}$ of the pyrrole compound having Formula P1 or utilized as $R^{12p}$, $R^{13p}$, $R^{14p}$, $R^{22p}$, $R^{24p}$, $R^{33p}$, $R^{34p}$, $R^{42p}$, and $R^{45p}$ of the pyrrole compounds having Formulas P2, P3, P4, and/or P5 independently can be a halide, a hydrocarboxy group, or an organyl group; alternatively, a halide or an organyl group; or alternatively, a hydrocarboxy group or an organyl group. In an embodiment, each non-hydrogen substituent group which can be utilized as $R^{2p}$, $R^{3p}$, $R^{4p}$, and $R^{5p}$ of the pyrrole compound having Formula P1 or utilized as $R^{12p}$, $R^{13p}$, $R^{14p}$, $R^{22p}$, $R^{24p}$, $R^{33p}$, $R^{34p}$, $R^{42p}$, and $R^{45p}$ of the pyrrole compounds having Formulas P2, P3, P4, and/or P5 independently can be a halide, a hydrocarbyl group, or an hydrocarboxy group; alternatively, a halide or a hydrocarbyl group; alternatively, a halide or hydrocarboxy group; alternatively, a hydrocarbyl group or a hydrocarbyl group; alternatively, a halide; alternatively, a hydrocarboxy group; or alternatively, an hydrocarbyl group.

In an aspect or any embodiment described herein, each organyl group which can be utilized as a non-hydrogen substituent group of the pyrrole compound having Formula P1, P2, P3, P4, and/or P5 independently can be a $C_1$ to $C_{30}$ organyl group; alternatively, a $C_1$ to $C_{18}$ organyl group; alternatively, a $C_1$ to $C_{10}$ organyl group; or alternatively, a $C_1$ to $C_5$ organyl group. In an aspect or any embodiment described herein, each hydrocarbyl group which can be utilized as a non-hydrogen substituent group of the pyrrole compound having Formula P1, P2, P3, P4, and/or P5 independently can be a $C_1$ to $C_{30}$ hydrocarbyl group; alternatively, a $C_1$ to $C_{18}$ hydrocarbyl group; alternatively, a $C_1$ to $C_{10}$ hydrocarbyl group; or alternatively, a $C_1$ to $C_5$ hydrocarbyl group. In an aspect or any embodiment described herein, each hydrocarboxy group which can be utilized as a non-hydrogen substituent group of the pyrrole compound having Formula P1, P2, P3, P4, and/or P5 independently can be a $C_1$ to $C_{30}$ hydrocarboxy group; alternatively, a $C_1$ to $C_{18}$ hydrocarboxy group; alternatively, a $C_1$ to $C_{10}$ hydrocarboxy group; or alternatively, a $C_1$ to $C_5$ hydrocarboxy group.

In an aspect or any embodiment described herein, each halide which can be utilized as a non-hydrogen substituent group of the pyrrole compound having Formula P1, P2, P3, P4, and/or P5 independently can be fluoride, chloride, bromide, or iodide. In an aspect or any embodiment described herein, each halide which can be utilized as a non-hydrogen substituent group of the pyrrole compound having Formula P1, P2, P3, P4, and/or P5 independently can be fluoride; alternatively, chloride; alternatively, bromide; or alternatively, iodide.

In an embodiment, each non-hydrogen substituent group which can be utilized as a non-hydrogen substituent group of the pyrrole compound having Formula P1, P2, P3, P4, and/or P5 independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group, a cycloalkyl group, an aryl group, or an aralkyl group; alternatively, an alkyl group or a substituted alkyl group; alternatively, a cycloalkyl group or a substituted cycloalkyl group; alternatively, an aryl group or a substituted aryl group; or alternatively, an aralkyl group or a substituted aralkyl group. In other embodiments, each non-hydrogen substituent group which can be utilized as a non-hydrogen substituent group of the pyrrole compound having Formula P1, P2, P3, P4, and/or P5 independently can be alkyl group; alternatively, a substituted alkyl group; alternatively, a cycloalkyl group; alternatively, a substituted cycloalkyl group; alternatively, an aryl group; alternatively, a substituted aryl group; alternatively, an aralkyl group; or alternatively, a substituted aralkyl group. Generally, the alkyl group, substituted alkyl group, cycloalkyl group, substituted cycloalkyl group, aromatic group, substituted aromatic group, aryl group, substituted aryl group, aralkyl group, substituted aralkyl group, and/or silyl group which can be utilized as a non-hydrogen substituent group of the pyrrole compound having Formula P1, P2, P3, P4, and/or P5 can have the same number of carbons as its respective organyl group or hydrocarbyl group which can be utilized as a non-hydrogen substituent group of the pyrrole compound having Formula P1, P2, P3, P4, and/or P5 disclosed herein.

In an embodiment, each alkyl group which can be utilized as a non-hydrogen substituent group of the pyrrole compound having Formula P1, P2, P3, P4, and/or P5 independently can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In some embodiments, each alkyl group which can be utilized as a non-hydrogen substituent group of the pyrrole compound having Formula P1, P2, P3, P4, and/or P5 independently can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group. In an embodiment, any of these alkyl groups can be substituted to form a substituted alkyl group. In an embodiment, each substituent of a substituted alkyl group independently can be a halide or hydrocarboxy group; alternatively, a halide; or alternatively a hydrocarboxy group. Substituent halides and hydrocarboxy groups are independently disclosed herein and can be utilized without limitation to further describe the substituted alkyl group which can be utilized as a non-hydrogen substituent group of the pyrrole compound having Formula P1, P2, P3, P4, and/or P5.

In an embodiment, each non-hydrogen substituent group which can be utilized as a non-hydrogen substituent group of the pyrrole compound having Formula P1, P2, P3, P4, and/or P5 independently can be an cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, each non-hydrogen substituent group which can be utilized as a non-hydrogen substituent group of the pyrrole compound having Formula P1, P2, P3, P4, and/or P5 independently can be a cyclopentyl group, a substituted cyclopentyl group, a cyclohexyl group, or a substituted cyclohexyl group. In other embodiments, each non-hydrogen substituent group which can be utilized as a non-hydrogen substituent group of the pyrrole compound having Formula P1, P2, P3, P4, and/or P5 independently can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group or a substituted cyclooctyl group. In further embodiments, each non-hydrogen substituent group which can be utilized as a non-hydrogen substituent group of the pyrrole compound having Formula P1, P2, P3, P4, and/or P5 independently can be a cyclopentyl group; alternatively, a substituted cyclopentyl group; alternatively, a cyclohexyl group; or alternatively, a substituted cyclohexyl group. Substituents which can be utilized for the substituted cycloalkyl groups are independently disclosed herein and can be utilized without limitation to further describe the substituted cycloalkyl group which can be utilized as a non-hydrogen substituent group of the pyrrole compound having Formula P1, P2, P3, P4, and/or P5.

In some embodiments, each non-hydrogen substituent group which can be utilized as a non-hydrogen substituent group of the pyrrole compound having Formula P1, P2, P3, P4, and/or P5 independently can be a phenyl group, a substituted phenyl group, a naphthyl group, or a substituted naphthyl group. In an embodiment, each non-hydrogen substituent group which can be utilized as a non-hydrogen substituent group of the pyrrole compound having Formula P1, P2, P3, P4, and/or P5 independently can be a phenyl group or a substituted phenyl group; alternatively, a naphthyl group or a substituted naphthyl group; alternatively, a phenyl group or a naphthyl group; or alternatively, a substituted phenyl group or a substituted naphthyl group. Substituents which can be utilized for the substituted phenyl groups or substituted naphthyl groups are independently disclosed herein and can be utilized without limitation to further describe the substituted phenyl groups or substituted naphthyl groups which can be utilized as a non-hydrogen substituent group of the pyrrole compound having Formula P1, P2, P3, P4, and/or P5.

In an embodiment, each substituted phenyl group which can be utilized as a non-hydrogen substituent group of the pyrrole compound having Formula P1, P2, P3, P4, and/or P5 independently can be a 2-substituted phenyl group, a 3-substituted phenyl group, a 4-substituted phenyl group, a 2,4-disubstituted phenyl group, a 2,6-disubstituted phenyl group, 3,5-disubstituted phenyl group, or a 2,4,6-trisubstituted phenyl group. In other embodiments, each substituted phenyl group which can be utilized as a non-hydrogen substituent group of the pyrrole compound having Formula P1, P2, P3, P4, and/or P5 independently can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, 3,5-disubstituted phenyl group; or alternatively, a 2,4,6-trisubstituted phenyl group. Substituents which can be utilized for these specific substituted phenyl groups are independently disclosed herein and can be utilized without limitation to further describe these substituted phenyl groups which can be utilized as a non-hydrogen substituent group of the pyrrole compound having Formula P1, P2, P3, P4, and/or P5.

In an embodiment, each non-hydrogen substituent group which can be utilized as a non-hydrogen substituent group of the pyrrole compound having Formula P1, P2, P3, P4, and/or P5 independently can be a benzyl group or a substituted benzyl group. In an embodiment, each non-hydrogen substituent group which can be utilized as a non-hydrogen substituent group of the pyrrole compound having Formula P1, P2, P3, P4, and/or P5 independently can be a benzyl group, or alternatively, a substituted benzyl group. Substituents which can be utilized for the substituted aralkyl groups are independently disclosed herein and can be utilized without limitation to further describe the substituted aralkyl groups which can be utilized as a non-hydrogen substituent group of the pyrrole compound having Formula P1, P2, P3, P4, and/or P5.

In an embodiment, each non-hydrogen substituent group which can be utilized as a non-hydrogen substituent group of the pyrrole compound having Formula P1, P2, P3, P4, and/or P5 independently can be an alkoxy group, a substituted alkoxy group, a cycloalkoxy group, a substituted cycloalkoxy group, an aroxy group, a substituted aroxy group, an aralkoxy group, or a substituted aralkoxy group; alternatively, an alkoxy group, a cycloalkoxy group, an aroxy group, or an aralkoxy group; alternatively, an alkoxy group or a substituted alkoxy group; alternatively, a cycloalkoxy group or a substituted cycloalkoxy group; alternatively, an aroxy group or a substituted aroxy group; or alternatively, an aralkoxy group or a substituted aralkoxy group. In other embodiments, each non-hydrogen substituent group which can be utilized as a non-hydrogen substituent group of the pyrrole compound having Formula P1, P2, P3, P4, and/or P5 independently can be alkoxy group; alternatively, a substituted alkoxy group; alternatively, a cycloalkoxy group; alternatively, a substituted cycloalkoxy group; alternatively, an aroxy group; alternatively, a substituted aroxy group; alternatively, an aralkoxy group; or alternatively, a substituted aralkoxy group. Generally, the alkoxy group, substituted alkoxy group, cycloalkoxy group, substituted cycloalkoxy group, aromatic group, substituted aromatic group, aroxy group, substituted aroxy group, aralkoxy group, and/or substituted aralkoxy group which can be utilized as a non-hydrogen substituent group of the pyrrole compound having Formula P1, P2, P3, P4, and/or P5 can have the same number of carbons as the hydrocarboxy group which can be utilized as a non-hydrogen substituent group of the pyrrole compound having Formula P1, P2, P3, P4, and/or P5 disclosed herein.

In a non-limiting embodiment, each coordinating compound independently can be, comprise, or consist essentially of, pyrrole, 2,5-dimethylpyrrole, 2-methyl-5-ethylpyrrole, 2,5-diethylpyrrole, 2-ethyl-5-n-propylpyrrole, 2,5-di-n-propylpyrrole, 2,5-diisopropylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2-methyl-4-isopropylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neo-pentylpyrrole, 2-ethyl-4-neopentylpyrrole, 3,4-diisopropylpyrrole, 3,4-di-sec-butylpyrrole, 3,4-diisobutylpyrrole, 3,4-di-t-butylpyrrole, 3,4-di-neo-pentylpropylpyrrole, 2,3,5-triethylpyrrrole, 2,3,5-tri-n-butylpyrrole, 2,3,5-tri-n-pentylpyrrole, 2,3,5-tri-n-hexylpyrrole, 2,3,5-tri-n-heptylpyrrole, 2,3,5-tri-n-octylpyrrole, 2,3,4,5-tetraethylpyrrole, 2,3,4,5-tetra-n-butylpyrrole, 2,3,4,5-tetra-n-hexylpyrrole, 2,5-dibenzylpyrrole, 2,4-dimethylpyrrole, 2-methyl-4-isopropylpyrrole, 2,4-dimethyl-3-ethylpyrrole, 2,4-diethylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neopentylpyrrole, 2-ethyl-4-neopentylpyrrole, 3,4-dimethylpyrrole, 3,4-diethylpyrrole, 3,4-diisopropylpyrrole, 3,4-di-sec-butylpyrrole, 3,4-diisobutylpyrrole, 3,4-di-t-butylpyrrole, 3,4-di-neopentylpyrrole, or any combination thereof. In other non-limiting embodiments, each coordinating compound independently can be, comprise, or consist essentially of, pyrrole, 2,5-dimethylpyrrole, 2-methyl-5-ethylpyrrole, 2,5-diethylpyrrole, 2,5-di-n-propylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, or any combination thereof; alternatively, pyrrole; alternatively, 2,5-dimethylpyrrole, alternatively, 2-methyl-5-ethylpyrrole; alternatively, 2,5-diethylpyrrole; alternatively, 2,5-di-n-propylpyrrole; alternatively, 2,5-di-n-butylpyrrole; alternatively, 2,5-di-n-pentylpyrrole; alternatively, 2,5-n- hexylpyrrole; alternatively, 2,5-di-n-heptylpyrrole; or alternatively, 2,5-di-n-octylpyrrole.

In a non-limiting embodiment, each coordinating compound independently can be, comprise, or consist essentially of, pyrrole, 2,5-bis(2',2',2'-trifluoroethyl)pyrrole, 2,5-bis(2'-methoxymethyl)pyrrole, pyrrole-2-carboxylic acid, 2-acetylpyrrole, pyrrole-2-carboxaldehyde, 3-acetyl-2,4-dimethylpyrrole, ethyl-2,4-dimethyl-5-(ethoxycarbonyl)-3-pyrrole-proprionate, ethyl-3,5-dimethyl-2-pyrrolecarboxylate, 3,4-dichloropyrrole, 2,3,4,5-tetrachloropyrrole, or any combination thereof. In other non-limiting embodiments, each coordinating compound independently can be, comprise, or consist essentially of, pyrrole, pyrrole-2-carboxylic acid, 2-acetylpyrrole, pyrrole-2-carboxaldehyde, 3-acetyl-2, 4-dimethylpyrrole, ethyl-2,4-dimethyl-5-(ethoxycarbonyl)-3-pyrrole-proprionate, or ethyl-3,5-dimethyl-2-pyrrolecarboxylate, or any combination thereof; alternatively, 3,4-dichloropyrrole, 2,3,4,5-tetrachloropyrrole, or any combination thereof. In yet other non-limiting embodiments, each coordinating compound independently can be, comprise, or consist essentially of, 2,5-bis(2',2',2'-trifluoroethyl) pyrrole; alternatively, 2,5-bis(2'-methoxymethyl)pyrrole; alternatively, pyrrole-2-carboxylic acid; alternatively, 2-acetylpyrrole; alternatively, pyrrole-2-carboxaldehyde; alternatively, 3-acetyl-2,4-dimethylpyrrole; alternatively, ethyl-2,4-dimethyl-5-(ethoxycarbonyl)-3-pyrrole-proprionate; alternatively, ethyl-3,5-dimethyl-2-pyrrolecarboxylate; alternatively, 3,4-dichloropyrrole; or alternatively, 2,3,4,5-tetrachloropyrrole.

In an embodiment, any phosphine and/or acyclic phosphine (substituted or unsubstituted), which can be utilized as the coordinating compound, can be, comprise, or consist essentially of, a $C_3$-$C_{60}$ phosphine and/or acyclic phosphine; alternatively, a $C_3$-$C_{45}$ phosphine and/or acyclic phosphine; alternatively, a $C_3$-$C_{30}$ phosphine and/or acyclic phosphine; alternatively, a $C_3$-$C_{20}$ phosphine and/or acyclic phosphine; or alternatively, a $C_3$-$C_{10}$ phosphine and/or acyclic phosphine. In an embodiment, any cyclic phosphine (substituted or unsubstituted, and/or aliphatic or aromatic), which can be utilized as the coordinating compound, can be, comprise, or consist essentially of, a $C_4$-$C_{60}$ cyclic phosphine; alternatively, a $C_4$-$C_{45}$ cyclic phosphine; alternatively, a $C_4$-$C_{30}$ cyclic phosphine; alternatively, a $C_4$-$C_{20}$ cyclic phosphine; or alternatively, a $C_4$-$C_{15}$ cyclic phosphine.

In an aspect of this disclosure, each coordinating compound can independently be a hydro-carbylphosphine, a substituted hydrocarbyl phosphine, a dihydrocarbylphosphine, a substituted dihydrocarbylphosphine, a trihydrocarbylphosphine, a substituted trihydrocarbylphosphine, any combination thereof; a hydrocarbylphosphine, a dihydrocarbylphosphine, a trihydrocarbylphosphine, or any combination thereof; alternatively, a hydrocarbylphosphine or a substituted hydrocarbylphosphine; alternatively, a dihydrocarbylphosphine or a substituted dihydrocarbylphosphine; alternatively, a trihydrocarbylphosphine or a substituted trihydrocarbylphosphine; alternatively, a hydrocarbylphosphine; alternatively, a substituted hydrocarbylphosphine; alternatively, a dihydrocarbylphosphine; alternatively, a substituted dihydrocarbylphosphine; alternatively, a trihydrocarbylphosphine; or alternatively, a substituted trihydrocarbylphosphine. Hydrocarbyl groups (substituted or substituted) are generally defined within the present disclosure as non-hydrogen substituent(s) for the substituted cycloalkyl group, substituted aromatic group, substituted aryl group, or substituted aralkyl group which can be utilized as $R^1$ of the nitrile having the formula $R^1C\equiv N$, $R^2$ and $R^3$ of the ether having formula $R^2-O-R^3$, $R^4$ and $R^5$ having the formula $R^4-S-R^5$, $R^6$, $R^7$, and $R^8$ of the amine having the formula $NR^6R^7R^8$, $NHR^6R^7$, or $NH_2R^6$, $R^9$, $R^{10}$, and $R^{11}$ of the phosphine having the formula $PR^9R^{10}R^{11}$, $PHR^9R^{10}$, or $PH_2R^9$, and $R^{12}$, $R^{13}$, and $R^{14}$ of the phosphite having the formula $P(OR^{12})(OR^{13})(OR^{14})$ or $PH(O)(OR^{12})(OR^{13})$. These hydrocarbyl substituent groups (substituted or substituted) can be utilized without limitation as the hydrocarbyl groups of the hydrocarbylphosphines (substituted or unsubstituted), dihydrocarbylphosphines (substituted or unsubstituted), and/or trihydrocarbylphosphines (substituted or unsubstituted) which can be utilized as the coordinating compound.

In a non-limiting embodiment, each coordinating compound independently can be, comprise, or consist essentially of, trimethylphosphine, triethylphosphine, tripropylphosphine, tributylphosphine, or any combination thereof. In another non-limiting embodiment, each coordinating compound independently can be, comprise, or consist essentially of, trimethylphosphine, triethylphosphine, tripropylphosphine, tributylphosphine, or any combination thereof; alternatively, trimethylphosphine; alternatively, triethylphosphine; alternatively, tripropylphosphine; or alternatively, tributylphosphine.

In a non-limiting embodiment, each coordinating compound independently can be, comprise, or consist essentially of, phenylphosphine, a substituted phenylphosphine, diphenylphosphine, a di(substituted phenyl)phosphine, triphenylphosphine, a tri(trisubstituted phenyl)phosphine, or any combination thereof; alternatively, phenylphosphine, a substituted phenylphosphine, or any combination thereof; alternatively, diphenylphosphine, a di(substituted phenyl)phosphine, or any combination thereof, or alternatively, triphenylphosphine, a tri(trisubstituted phenyl)phosphine, or any combination thereof. In a non-limiting embodiment, each coordinating compound independently can be, comprise, or consist essentially of, phenylphosphine; alternatively, a substituted phenylphosphine; alternatively, diphenylphosphine; alternatively, a di(substituted phenyl)phosphine; alternatively, triphenylphosphine; or alternatively, a tri(substituted phenyl)phosphine.

General substituents (also referred to as non-hydrogen substituents or non-hydrogen substituent groups) are independently disclosed herein. These substituent groups can be utilized without limitation to further describe any substituted phosphine, substituted acyclic phosphine, substituted cyclic phosphine (acyclic or cyclic), substituted phenylphosphine, di(substituted phenyl)phosphine, and/or tri(substituted phenyl)phosphine which can be utilized as the coordinating compound.

In some non-limiting embodiments, each coordinating compound independently can be, comprise, or consist essentially of, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenyl phosphine, or any combination thereof. In other non-limiting embodiments, each coordinating compound independently can be, comprise, or consist essentially of, phenylphosphine; alternatively, diphenylphosphine; alternatively, triphenyl-phosphine; alternatively, tolylphosphine; alternatively, ditolylphosphine; alternatively, tritolylphosphine; alternatively, methyldiphenylphosphine; alternatively, dimethylphenylphosphine; alternatively, ethyl-diphenylphosphine; or alternatively, diethylphenylphosphine.

In an embodiment, any phosphite and/or acyclic phosphite (substituted or unsubstituted), which can be utilized as the coordinating compound, can be, comprise, or consist essentially of, a $C_3$-$C_{60}$ phosphite and/or acyclic phosphite; alternatively, a $C_3$-$C_{45}$ phosphite and/or acyclic phosphite; alternatively, a $C_3$-$C_{30}$ phosphite and/or acyclic phosphite; alternatively, a $C_3$-$C_{20}$ phosphite and/or acyclic phosphite; or alternatively, a $C_3$-$C_{10}$ phosphite and/or acyclic phosphite. In an embodiment, any cyclic phosphite (substituted or unsubstituted, and/or aliphatic or aromatic), which can be utilized as the coordinating compound, can be, comprise, or consist essentially of, a $C_3$-$C_{60}$ cyclic phosphite; alternatively, a $C_4$-$C_{45}$ cyclic phosphite; alternatively, a $C_4$-$C_{30}$ cyclic phosphite; alternatively, a $C_4$-$C_{20}$ cyclic phosphite; or alternatively, a $C_4$-$C_{15}$ cyclic phosphite.

According to an aspect of this disclosure, each coordinating compound can independently be a dihydrocarbylphosphite, a substituted dihydrocarbylphosphite, a trihydrocarbylphosphite, a substituted trihydrocarbylphosphite, or any combination thereof; alternatively, a dihydrocarbylphosphite, a trihydro-carbylphosphite, or any combination thereof; a dihydrocarbylphosphite or a substituted dihydrocarbyl-phosphite; alternatively, a trihydrocarbylphosphite or a substituted trihydrocarbylphosphite; alternatively, a dihydrocarbylphosphite; alternatively, a substituted dihydrocarbylphosphite; alternatively, a trihydro-carbylphosphite; or alternatively, a substituted trihydrocarbylphosphite. Hydrocarbyl groups (substituted or substituted) are generally defined within the present disclosure as non-hydrogen substituent(s) for the substituted cycloalkyl group, substituted aromatic group, substituted aryl group, or substituted aralkyl group which can be utilized as $R^1$ of the nitrile having the formula $R^1C\equiv N$, $R^2$ and $R^3$ of the ether having formula $R^2$—O—$R^3$, $R^4$ and $R^5$ having the formula $R^4$—S—$R^5$, $R^6$, $R^7$, and $R^8$ of the amine having the formula $NR^6R^7R^8$, $NHR^6R^7$, or $NH_2R^6$, $R^9$, $R^{10}$, and $R^{11}$ of the phosphine having the formula $PR^9R^{10}R^{11}$, $PHR^9R^{10}$, or $PH_2R^9$, and $R^{12}$, $R^{13}$, and $R^{14}$ of the phosphite having the formula $P(OR^{12})(OR^{13})(OR^{14})$ or $PH(O)(OR^{12})(OR^{13})$. These hydrocarbyl substituent groups (substituted or substituted) can be utilized without limitation as the hydrocarbyl groups of the dihydrocarbylphosphite (substituted or unsubstituted) and/or trihydrocarbylphosphites (substituted or unsubstituted) which can be utilized as the coordinating compound.

In a non-limiting embodiment, each coordinating compound independently can be, comprise, or consist essentially of, trimethylphosphite, triethylphosphite, tripropylphosphite, tributylphosphite, methyldiphenylphosphite, dimethylphenylphosphite, ethyldiphenylphosphite, diethylphenylphosphite, diphenylphosphite, triphenylphosphite, ditolylphosphite, tritolylphosphite, or any combination thereof. In another non-limiting embodiment, each coordinating compound independently can be, comprise, or consist essentially of, trimethylphosphite, triethylphosphite, tripropylphosphite, tributylphosphite, or any combination thereof.

In a non-limiting embodiment, each coordinating compound independently can be, comprise, or consist essentially of, diphenylphosphite, a di(substituted phenyl)phosphite, triphenylphosphite, tri(substitute phenyl)phosphite, or any combination thereof; alternatively, diphenylphosphite, triphenylphosphite, or any combination thereof. In other non-limiting embodiments, each coordinating compound independently can be, comprise, or consist essentially of, diphenylphosphite; alternatively, a di(substituted phenyl) phosphite; alternatively, a triphenylphosphite; or alternatively, a tri(substituted phenyl)phosphite.

General substituents (also referred to as non-hydrogen substituents or non-hydrogen substituent groups) are independently disclosed herein. These substituent groups can be utilized without limitation to further describe any substituted phosphite, substituted acyclic phosphite, and/or substituted cyclic phosphite, di(substituted phenyl) phosphites, and/or tri(substituted phenyl) phosphites which can be utilized as the coordinating ligand.

In another non-limiting embodiment, each coordinating compound independently can be, comprise, or consist essentially of, methyldiphenylphosphite, dimethylphenylphosphite, ethyldiphenylphosphite, diethylphenylphosphite, or any combination thereof; alternatively, diphenylphosphite, triphenylphosphite, ditolylphosphite, tritolylphosphite, or any combination thereof; alternatively, triphenylphosphite, tritolylphosphite, or any combination thereof. In yet another non-limiting embodiment, each coordinating compound independently can be, comprise, or consist essentially of, dimethylphenylphosphite; alternatively, ethyldiphenylphosphite; alternatively, diethylphenylphosphite; alternatively, diphenylphosphite; alternatively, triphenylphosphite; alternatively, ditolylphosphite; or alternatively, tritolylphosphite.

According to an aspect of this disclosure, each coordinating compound independently can be, comprise, or consist essentially of, a substituted or unsubstituted azetidine, oxetane, thietane, dioxetane, dithietane, tetrahydropyrrole, dihydropyrrole, pyrrole, indole, isoindole, tetrahydrofuran, dihydrofuran, furan, benzofuran, isobenzofuran, tetrahydrothiophene, dihydrothiophene, thiophene, benzothiophene, isobenzothiophene, imidazolidine, pyrazole, imidazole, oxazolidine, oxazole, isoxazole, thiazolidine, thiazole, isothiazole, benzothiazole, dioxolane, dithiolane, triazole, dithiazole, piperidine, pyridine, oxane, dihydropyran, pyran, thiane, piperazine, diazine, oxazine, thiazine, dithiane, dioxane, dioxin, triazine, triazinane, trioxane, oxepin, azepine, thiepin, diazepine, morpholine, quinoline, tetrahydroquinone, bicyclo[3.3.1]tetrasiloxane, or any combination thereof; alternatively, a substituted or unsubstituted azetidine, oxetane, thietane, dioxetane, dithietane, tetrahydropyrrole, tetrahydrofuran, tetrahydrothiophene, imidazolidine, oxazolidine, oxazole, thiazolidine, thiazole, dioxolane, dithiolane, piperidine, oxane, pyran, thiane, piperazine, oxazine, thiazine, dithiane, dioxane, dioxin, triazinane, trioxane, azepine, thiepin, diazepine, morpholine, 1,2-thiazole, bicyclo[3.3.1]tetrasiloxane, or any combination thereof; alternatively, a substituted or unsubstituted tetrahydropyrrole, tetrahydrofuran, tetrahydrothiophene, oxazolidine, thiazolidine, dioxolane, dithiolane, dithiazole, piperidine, oxane, pyran, thiane, piperazine, dithiane, dioxane, dioxin, trioxane, morpholine, or any combination thereof; alternatively, a substituted or unsubstituted tetrahydrofuran, tetrahydrothiophene, dioxolane, dithiolane, oxane, pyran, thiane, dithiane, dioxane, dioxin, trioxane, or any combination thereof; alternatively, tetrahydrofuran, dioxolane, oxane, dioxane, trioxane; or any combination thereof; alternatively, a substituted or unsubstituted pyrrole, furan, pyrazole, imidazole, oxazole, isoxazole, thiazole, isothiazole, triazole, pyridine, diazine, triazine, quinoline, or combinations thereof; alternatively, a substituted or unsubstituted pyrrole, furan, imidazole, oxazole, thiazole, triazole, pyridine, diazine, triazine, or combinations thereof; alternatively, furan, oxazole, thiazole, triazole, pyridine, diazine, triazine, or combinations thereof.

According to an aspect of this disclosure, each coordinating compound independently can be, comprise, or consist essentially of, azetidine, oxetane, thietane, dioxetane, dithietane, tetrahydropyrrole, dihydropyrrole, pyrrole, indole, isoindole, tetrahydrofuran, dihydropyran, furan, benzofuran, isobenzofuran, tetrahydrothiophene, dihydrothiophene, thiophene, benzothiophene, isobenzothiophene, imidazolidine, pyrazole, imidazole, oxazolidine, oxazole, isoxazole, thiazolidine, thiazole, isothiazole, benzothiazole, dioxolane, dithiolane, triazole, dithiazole, piperidine, pyridine, oxane, dihydropyran, pyran, thiane, piperazine, diazine, oxazine, thiazine, dithiane, dioxane, dioxin, triazine, triazinane, trioxane, oxepin, azepine, thiepin, diazepine, morpholine, quinoline, tetrahydroquinone, bicyclo[3.3.1]tetrasiloxane, or any combination thereof; alternatively, azetidine, oxetane, thietane, dioxetane, dithietane, tetrahydropyrrole, tetrahydrofuran, tetrahydrothiophene, imidazolidine, oxazolidine, oxazole, thiazolidine, thiazole, dioxolane, dithiolane, piperidine, oxane, pyran, thiane, piperazine, oxazine, thiazine, dithiane, dioxane, dioxin, triazinane, trioxane, azepine, thiepin, diazepine, morpholine, 1,2-thiazole, bicyclo[3.3.1]tetrasiloxane, or any combination thereof; alternatively, tetrahydropyrrole, tetrahydrofuran, tetrahydrothiophene, oxazolidine, thiazolidine, dioxolane, dithiolane, dithiazole, piperidine, oxane, pyran, thiane, piperazine, dithiane, dioxane, dioxin, trioxane, morpholine, or any combination thereof; alternatively, tetrahydrothiophene, dioxolane, dithiolane, oxane, pyran, thiane, dithiane, dioxane, dioxin, trioxane, or any combination thereof; alternatively, tetrahydrofuran, dioxolane, oxane, dioxane, trioxane; or any combination thereof; alternatively, pyrrole, furan, pyrazole, imidazole, oxazole, isoxazole, thiazole, isothiazole, triazole, pyridine, diazine, triazine, quinoline, or combinations thereof; alternatively, pyrrole, furan, imidazole, oxazole, thiazole, triazole, pyridine, diazine, triazine, or combinations thereof; alternatively, furan, oxazole, thiazole, triazole, pyridine, diazine, triazine, or combinations thereof.

According to an aspect of this disclosure, each coordinating compound independently can be, comprise, or consist essentially of, a substituted or unsubstituted azetidine, tetrahydropyrrole, dihydropyrrole, pyrrole, indole, isoindole, imidazolidine, pyrazole, imidazole, oxazolidine, oxazole, isoxazole, thiazolidine, thiazole, isothiazole, triazole, benzotriazole, dithiazole, piperidine, pyridine, piperazine, diazine, oxazine, thiazine, triazine, azepine, diazepine, morpholine, quinoline, tetrahydroisoquinoline, or any combination thereof; alternatively, a substituted or unsubstituted tetrahydropyrrole, pyrrole, indole, isoindole, imidazolidine, imidazole, oxazolidine, oxazole, thiazolidine, thiazole, piperidine, pyridine, piperazine, diazine, triazine, morpholine, quinoline, tetrahydroisoquinoline, or any combination thereof; alternatively, a substituted or unsubstituted tetrahydropyrrole, pyrrole, isoindole, imidazole, oxazolidine, oxazole, thiazolidine, thiazole, piperidine, pyridine, piperazine, diazine, triazine, morpholine, quinoline, or any combination thereof; alternatively, a substituted or unsubstituted tetrahydropyrrole, pyrrole, imidazole, oxazole, thiazole, piperidine, pyridine, piperazine, diazine, triazine, morpholine, quinoline, or any combination thereof; alternatively, a substituted or unsubstituted tetrahydropyrrole, pyrrole, piperidine, piperazine, morpholine, quinoline, or any combination thereof; or alternatively, a substituted or unsubstituted imidazole, oxazole, thiazole, pyridine, diazine, triazine, or any combination thereof. In some embodiments, each coordinating compound independently can be, comprise, or consist essentially of, azetidine, tetrahydropyrrole, dihydropyrrole, pyrrole, indole, isoindole, imidazolidine, pyrazole, imidazole, oxazolidine, oxazole, isoxazole, thiazolidine, thiazole, isothiazole, triazole, benzotriazole, dithiazole, piperidine, pyridine, piperazine, diazine, oxazine, thiazine, triazine, azepine, diazepine, morpholine, quinoline, tetrahydroisoquinoline, or any combination thereof; alternatively, tetrahydropyrrole, pyrrole, indole, isoindole, imidazolidine, imidazole, oxazolidine, oxazole, thiazolidine, thiazole, piperidine, pyridine, piperazine, diazine, triazine, morpholine, quinoline, tetrahydroisoquinoline, or any combination thereof; alternatively, tetrahydropyrrole, pyrrole, isoindole, imidazole, oxazolidine, oxazole, thiazolidine, thiazole, piperidine, pyridine, piperazine, diazine, triazine, morpholine, quinoline, or any combination thereof; alternatively, tetrahydropyrrole, pyrrole, imidazole, oxazole, thiazole, piperidine, pyridine, piperazine, diazine, triazine, morpholine, quinoline, or any combination thereof; alternatively, tetrahydropyrrole, pyrrole, piperidine, piperazine, morpholine, quinoline, or any combination thereof; or alternatively, imidazole, oxazole, thiazole, pyridine, diazine, triazine, or any combination thereof.

According to an aspect of this disclosure, each coordinating compound independently can be, comprise, or consist essentially of, a substituted or unsubstituted oxetane, dioxetane, tetrahydrofuran, dihydrofuran, furan, benzofuran, isobenzofuran, oxazolidine, oxazole, isoxazole, dioxolane, oxane, dihydropyran, pyran, oxazine, dioxane, dioxin, trioxane, oxepin, morpholine, or bicyclo[3.3.1]tetrasiloxane, or any combination thereof; alternatively, a substituted or unsubstituted oxetane, dioxetane, tetrahydrofuran, furan, isobenzofuran, oxazolidine, oxazole, dioxolane, oxane, pyran, dioxane, dioxin, trioxane, morpholine, or any combination thereof; alternatively, a substituted or unsubstituted tetrahydrofuran, oxazole, dioxolane, oxane, dioxane, dioxin, trioxane, or any combination thereof; or alternatively, a substituted or unsubstituted tetrahydrofuran, dioxolane, oxane, dioxane, trioxane, or any combination thereof. In some embodiments, each coordinating compound independently can be, comprise, or consist essentially of, oxetane, dioxetane, tetrahydrofuran, dihydrofuran, furan, benzofuran, isobenzofuran, oxazolidine, oxazole, isoxazole, dioxolane, oxane, dihydropyran, pyran, oxazine, dioxane, dioxin, trioxane, oxepin, morpholine, or bicyclo[3.3.1]tetrasiloxane, or any combination thereof; alternatively, oxetane, dioxetane, tetrahydrofuran, furan, isobenzofuran, oxazolidine, oxazole, dioxolane, oxane, pyran, dioxane, dioxin, trioxane, morpholine, or any combination thereof; alternatively, tetrahydrofuran, oxazole, dioxolane, oxane, dioxane, dioxin, trioxane, or any combination thereof; or alternatively, tetrahydrofuran, dioxolane, oxane, dioxane, trioxane, or any combination thereof.

According to an aspect of this disclosure, each coordinating compound independently can be, comprise, or consist essentially of, a substituted or unsubstituted thietane, dithietane, tetrahydrothiophene, dihydrothiophene, thiophene, benzothiophene, isobenzothiophene, thiazolidine, thiazole, isothiazole, dithiolane, dithiazole, thiane, thiazine, dithiane, thiepin, or any combination thereof; alternatively, a substituted or unsubstituted thietane, dithietane, tetrahydrothiophene, thiophene, isobenzothiophene, thiazolidine, thiazole, dithiolane, thiane, dithiane, or any combination thereof; or alternatively, a substituted or unsubstituted tetrahydrothiophene, dithiolane, thiane, dithiane, or any combination thereof. In some embodiments, each coordinating compound independently can be, comprise, or consist essentially of, a substituted or unsubstituted substituted or unsubstituted, thietane, dithietane, tetrahydrothiophene, dihydrothiophene, thiophene, benzothiophene, isobenzothiophene, thiazolidine, thiazole, isothiazole, dithiolane, dithiazole, thiane, thiazine, dithiane, thiepin, or any combination thereof; alternatively, thietane, dithietane, tetrahydrothiophene, thiophene, isobenzothiophene, thiazolidine, thiazole, dithiolane, thiane, dithiane, or any combination thereof; or alternatively, tetrahydrothiophene, dithiolane, thiane, dithiane, or any combination thereof.

In some embodiments, each coordinating compound independently can be, comprise, or consist essentially of, azetidine; alternatively, oxetane; alternatively, thietane; alternatively, dioxetane; alternatively, dithietane; alternatively, tetrahydropyrrole; alternatively, dihydropyrrole, alternatively, pyrrole; alternatively, indole; alternatively, isoindole; alternatively, tetrahydrofuran; alternatively, dihydropyrrole; alternatively, furan; alternatively, benzofuran; alternatively, isobenzofuran; alternatively, tetrahydrothiophene; alternatively, dihydrothiophene; alternatively, thiophene; alternatively, benzothiophene; alternatively, isobenzothiophene; alternatively, imidazolidine; alternatively, pyrazole; alternatively, imidazole; alternatively, oxazolidine; alternatively, oxazole; alternatively, isoxazole; alternatively, thiazolidine; alternatively, thiazole; alternatively, benzothiazole; alternatively, isothiazole; alternatively, dioxolane; alternatively, dithiolane; alternatively, triazole; alternatively, dithiazole; alternatively, piperidine; alternatively, pyridine; alternatively, oxane; alternatively, dihydropyran; alternatively, pyran; alternatively, thiane; alternatively, piperazine; alternatively, diazine; alternatively, oxazine; alternatively, thiazine; alternatively, dithiane; alternatively, dioxane; alternatively, dioxin; alternatively, triazine; alternatively, triazinane; alternatively, trioxane; alternatively, oxepin; alternatively, azepine; alternatively, thiepin; alternatively, diazepine; alternatively, morpholine; alternatively, quinoline; alternatively, tetrahydroquinone; or alternatively, bicyclo[3.3.1]tetrasiloxane.

According to an aspect of this disclosure, each coordinating compound independently can be, comprise, or consist essentially of, tetrahydrofuran (THF), furan, methyltetrahydrofuran, dihydrofuran, oxane, 2,3-dihydropyran, 1,3-dioxane, 1,4-dioxane, morpholine, N-methylmorpholine, acetonitrile, propionitrile, butyronitrile, benzonitrile, pyridine, ammonia ($NH_3$), methyl amine ($NH_2Me$), ethylamine ($NH_2Et$), dimethylamine ($NHMe_2$), diethylamine ($NHEt_2$), trimethylamine ($NMe_3$), triethylamine ($NEt_3$), trimethylphosphine ($PMe_3$), triethylphosphine ($PEt_3$), triphenylphosphine ($PPh_3$), tri-n-butylphosphine ($P(n-Bu)_3$), trimethylphosphite ($P(OMe)_3$), triethylphosphite ($P(OEt)_3$), tri-n-butylphosphite ($P(O-n-Bu)_3$), methyl isocyanide, n-butyl isocyanide, phenyl isocyanide, $SMe_2$, thiophene, or tetrahydrothiophene (THT). In some embodiments, each coordinating compound independently can be, comprise, or consist essentially of, tetrahydrofuran (THF), methyltetrahydrofuran, oxane, 1,4-dioxane, acetonitrile, pyridine, ammonia ($NH_3$), trimethylamine ($NMe_3$), triethylamine ($NEt_3$), trimethylphosphine ($PMe_3$), triethylphosphine ($PEt_3$), triphenylphosphine ($PPh_3$), $SMe_2$, or tetrahydrothiophene (THT); alternatively, tetrahydrofuran (THF), methyltetrahydrofuran, oxane, or 1,4-dioxane; alternatively, ammonia ($NH_3$), trimethylamine ($NMe_3$), or triethylamine ($NEt_3$); or alternatively, trimethylphosphine ($PMe_3$), triethylphosphine ($PEt_3$), triphenylphosphine ($PPh_3$). In other embodiments, each coordinating compound independently can be, comprise, or consist essentially of, tetrahydrofuran, acetonitrile, pyridine, ammonia, trimethylamine, trimethylphosphine, or triphenylphosphine; alternatively, tetrahydrofuran, acetonitrile, pyridine, trimethylamine, trimethylphosphine, or triphenylphosphine; or alternatively, tetrahydrofuran or acetonitrile. In still other embodiments, each coordinating compound independently can be, comprise, or consist essentially of, tetrahydrofuran (THF); alternatively, oxane; alternatively, 1,4-dioxane; alternatively, acetonitrile; alternatively, pyridine; alternatively, ammonia ($NH_3$); alternatively, trimethylamine ($NMe_3$); alternatively, triethylamine ($NEt_3$); alternatively, trimethylphosphine ($PMe_3$); alternatively, triethylphosphine ($PEt_3$); alternatively, triphenylphosphine ($PPh_3$); alternatively, $SMe_2$; or alternatively, tetrahydrothiophene (THT). In yet another embodiment, each coordinating compound independently can be, comprise, or consist essentially of, tetrahydrofuran, acetonitrile, pyridine, ammonia, trimethylamine, trimethylphosphine, or triphenylphosphine; alternatively, tetrahydrofuran, acetonitrile, pyridine, trimethylamine, trimethylphosphine, or triphenylphosphine; or alternatively, tetrahydrofuran or acetonitrile.

General substituents (also referred to as non-hydrogen substituents or non-hydrogen substituent groups) are independently disclosed herein. These substituent groups can be utilized without limitation to further describe any azetidine, oxetane, thietane, dioxetane, dithietane, tetrahydropyrrole, dihydropyrrole, pyrrole, indole, isoindole, tetrahydrofuran, dihydrofuran, furan, benzofuran, isobenzofuran, tetrahydrothiophene, dihydrothiophene, thiophene, benzothiophene, isobenzothiophene, imidazolidine, pyrazole, imidazole, oxazolidine, oxazole, isoxazole, thiazolidine, thiazole, isothiazole, benzothiazole, dioxolane, dithiolane, triazole, dithiazole, piperidine, pyridine, oxane, dihydropyran, pyran, thiane, piperazine, diazine, oxazine, thiazine, dithiane, dioxane, dioxin, triazine, triazinane, trioxane, oxepin, azepine, thiepin, diazepine, morpholine, quinoline, tetrahydroquinone, bicyclo[3.3.1]tetrasiloxane, oxetane, and/or dioxetane which can be utilized as the coordinating ligand.

This disclosure provides, among other things, a process for preparing a chromium(III) halide complex, having the formula $CrX_3.mL$ (or alternatively, $CrX_3L_m$). Generally, X represents a halide, L represents a coordinating compound, and m represents the number of moles of coordinating compound, L, per mole of chromium. X, L, and m are independent elements of the chromium(III) halide complex having formula $CrX_3L_m$. Each of these chromium(III) halide complex elements, and other elements, are independently described in this disclosure and can be utilized, without limitation, to describe the chromium(III) halide complex having formula $CrX_3L_m$.

As disclosed herein, the process for preparing the chromium(III) halide complex comprises contacting 1) a chromium(III) halide hydrate, 2) a water absorption agent, and 3) a coordinating compound, L, to form the chromium(III) halide complex having the formula $CrX_3.mL$. Generally, the halide, X, can have the same embodiments, as the halide for the chromium(III) halide hydrate from which the chromium (III) is prepared. In an embodiment, the halide, X, chromium (III) halide complex can be F, Cl, Br, or I; alternatively, F; alternatively, Cl; alternatively, Br; or alternatively, I.

In an embodiment, the number of moles, m, of the coordinating compound, L, per mole of chromium, can be any positive number; or alternatively, and positive integer. By describing the chromium(III) halide complex by using the terminology "$CrX_3.mL$," or as "$CrX_3L_m$" it is intended to reflect a general formula that includes all polymorphs of the chromium(III) halide complex, including those in which ligand L is coordinated, those in which L is interstitial or situated in the crystalline lattice, and those in which a combination of coordinated L and lattice L are present.

In an embodiment, the number of moles of coordinating ligand (or coordinating compound), m, per mole of chromium in the chromium(III) halide complex having the formula $CrX_3.mL$ ($CrX_3L_m$) can be from 0.25 to 10; alternatively, from 0.3 to 9.5; alternatively, from 0.4 to 9.0; alternatively, from 0.5 to 8.5; alternatively, from 0.6 to 8.0; alternatively, from 0.7 to 7.5; alternatively, from 0.8 to 7.0; alternatively, from 0.9 to 6.5; alternatively, from 1.0 to 6.0; alternatively, from 1.25 to 5.5; alternatively, from 1.50 to 5.0; alternatively, from 1.75 to 4.5; or alternatively, from 2.0 to 4.0. In some embodiments, the number of moles of coordinating ligand (or coordinating compound), m, per mole of chromium in the chromium(III) halide complex having the formula $CrX_3.mL$ ($CrX_3L_m$) can be about 0.25; alternatively, about 0.5; alternatively, about 0.75; alternatively, about 1; alternatively, about 1.5; alternatively, about 2; alternatively, about 2.5; alternatively, about 3; alternatively, about 3.5; alternatively, about 4; alternatively, about 4.5; alternatively, about 5; alternatively, about 5.5; alternatively, about 6; alternatively, about 7; alternatively, about 8; alternatively about 9; or alternatively, about 10. In other embodiments, the number of moles of coordinating ligand (or coordinating compound), m, per mole of chromium in the chromium(III) halide complex having the formula $CrX_3.mL$ (or $CrX_3L_m$) can be an integer ranging from 1 to 10; alternatively, ranging from 1 to 9; alternatively, from 1 to 8; alternatively, from 1 to 7; or alternatively, from 1 to 6. In some embodiments, the number of moles of coordinating ligand (or coordinating compound), m, per mole of chromium in the chromium(III) halide complex having the formula $CrX_3.mL$ ($CrX_3L_m$) can be 1; alternatively, 2; alternatively, 3; alternatively, 4; alternatively, 5; alternatively, 6; alternatively, 7; alternatively, 8; alternatively, 9; or alternatively, 10.

The ligands, L, of the anhydrous chromium(III) halide complex, having the formula $CrX_3.mL$, have been described herein as the coordinating compound. These coordinating compounds can be utilized without limitation to further describe the anhydrous chromium(III) halide complex, having the formula $CrX_3.mL$ (or $CrX_3L_m$). In some non-limiting embodiments, the chromium(III) halide complex having the formula $CrX_3.mL$ (or $CrX_3L_m$) can be, comprise, or consist essentially of, $CrCl_3(THF)_3$, $CrCl_3(NCCH_3)_3$, or $CrCl_3(C_5H_5N)_3$ ($C_5H_5N$ is pyridine). In some embodiments the anhydrous chromium(III) halide complex is $CrCl_3(THF)_3$; alternatively, $CrCl_3(NCCH_3)$; or alternatively, $CrCl_3(C_5H_5N)_3$.

In an aspect, the chromium(III) halide complex can be substantially anhydrous; or alternatively, anhydrous. In some embodiments the chromium(III) halide complex can have a water content of less than or equal to 100 ppm; alternatively, less than or equal to 75 ppm; alternatively, less than or equal to 50 ppm; or alternatively, less than or equal to 20 ppm. Generally, the water contents of the chromium(III) halide complex are based on the weight percent of water in the chromium(III) halide complex.

In an aspect, a process for preparing a chromium(III) halide complex can comprise: contacting 1) a chromium(III) halide hydrate, 2) a water absorption agent, and 3) a coordinating compound, L, to form a chromium(III) halide complex having the formula $CrX_3.mL$. In an embodiment, the process for preparing a chromium(III) halide complex can comprise: contacting 1) a chromium(III) halide hydrate, 2) a water absorption agent, and 3) a coordinating compound, L, to form solution comprising a chromium(III) halide complex having the formula $CrX_3.mL$. In a non-limiting aspect, a process for preparing a chromium(III) chloride complex can comprise: contacting 1) a chromium(III) chloride hydrate, 2) a water absorption agent, and 3) a coordinating compound, L, to form a chromium(III) chloride complex having the formula $CrCl_3.mL$. In an embodiment, the process for preparing a chromium(III) chloride complex can comprise: contacting 1) a chromium(III) chloride hydrate, 2) a water absorption agent, and 3) a coordinating compound, L, to form solution comprising a chromium(III) chloride complex having the formula $CrCl_3.mL$. In another non-limiting aspect, a process for preparing a $CrCl_3(THF)_3$ can comprise: contacting 1) a chromium(III) chloride hydrate, 2) 3 Å, 4 Å, 5 Å, 10×, or 13× molecular sieve, and 3) tetrahydrofuran to form $CrCl_3(THF)_3$. In an embodiment, the process for preparing a $CrCl_3(THF)_3$ can comprise: contacting 1) a chromium(III) chloride hydrate, 2) a 3 Å, 4 Å, 5 Å, 10×, or 13× molecular sieve, and 3) tetrahydrofuran to form solution comprising $CrCl_3(THF)_3$.

In an embodiment, a solution comprising the chromium(III) halide complex can comprise, or consist essentially of the chromium(III) halide complex and the coordinating compound; alternatively, can comprise, or consist essentially of the chromium(III) halide complex, the coordinating compound, and the water absorption agent; can comprise, or consist essentially of the chromium(III) halide complex, the coordinating compound, and a solvent; or alternatively, can comprise, or consist essentially of the chromium(III) halide complex, the coordinating compound, the water absorption agent and a solvent. In a non-limiting embodiment, the process for preparing a chromium(III) halide complex can comprise: contacting 1) a chromium(III) halide hydrate, 2) a water absorption agent, and 3) a coordinating compound, L, to form solution comprising a chromium(III) halide complex having the formula $CrX_3.mL$ and the coordinating compound. In some non-limiting embodiments, the solution can comprise, or consist essentially of, the chromium(III) halide complex having the formula $CrX_3.mL$, the coordinating compound, and the water absorption agent. Other aspects and embodiments of the process are independently described herein. These independently described aspects and embodiments can be combined in any conceivable fashion to further describe a process for preparing a chromium(III) halide complex. Additionally, aspects and embodiments of the chromium(III) halide hydrate, the water absorption agent, the coordinating compound, and the chromium(III) halide complex are independently described herein and these aspect and embodiments can be utilized without limitation to further describe a process for preparing a chromium(III) halide complex.

In an aspect, the chromium(III) halide hydrate, the water absorption agent, and the coordinating compound can be contacted in any combination or order. In an embodiment, the chromium(III) halide hydrate, the water absorption agent, and the coordinating compound can be contacted simultaneously. In an embodiment, the chromium(III) halide hydrate and the water absorption agent can be contacted to form a mixture, and the mixture subsequently contacted with the coordinating compound; alternatively, the chromium(III) halide hydrate and the coordinating compound can be contacted to form a mixture and the mixture subsequently contacted with the water absorption agent; or alternatively, the water absorption agent, and the coordinating compound can be contacted to form a mixture and the mixture subsequently contacted with the chromium(III) halide hydrate.

In an aspect, the step of contacting the chromium(III) halide hydrate, the water absorption agent, and the coordinating compound is not limited to a specific type of contacting or formation process, a specific reactor, or any particular engineering requirement. In an embodiment, the formation of the chromium(III) halide complex can occur via a batch process or a continuous process; alternatively, a batch process; or alternatively, a continuous process. In some embodiments, the formation of the chromium(III) halide complex can occur via a batch process in a slurry or mixture comprising the water absorption agent, chromium(III) halide hydrate, and coordinating compound. In some embodiments, the formation of the chromium(III) halide complex can be practiced as a continuous fixed bed process where a mixture of the chromium(III) halide hydrate and coordinating compound are flowed through a bed of water absorption agent.

In an aspect, the chromium(III) halide hydrate, the water absorption agent, and the coordinating compound can be contacted for at least 0.1 hours; alternatively, at least 0.15 hours; alternatively, at least 0.2 hours; alternatively, at least 0.25 hours; alternatively, at least 0.3 hours; alternatively, at least 0.35 hours; alternatively, at least 0.45, hours; or alternatively, at least 0.5 hours. In an embodiment, the maximum chromium(III) halide hydrate, the water absorption agent, and the coordinating compound contact time can be 72 hours; alternatively, 48 hours; alternatively, 36 hours; alternatively, 24 hours; alternatively, 18 hours; alternatively, 15 hours; alternatively, 12 hours; alternatively, 9 hours; alternatively, 8 hours; or alternatively, 7 hours. In some embodiments, a condition capable of forming the chromium(III) halide complex can include a chromium(III) halide hydrate, the water absorption agent, and the coordinating compound contact time that can range from any minimum chromium(III) halide hydrate, the water absorption agent, and the coordinating compound contact time disclosed herein to any maximum chromium(III) halide hydrate, the water absorption agent, and the coordinating compound contact time described herein. In some non-limiting embodiments, the chromium (III) halide hydrate, the water absorption agent, and the coordinating compound contact time can be from 0.1 hours to 72 hours; alternatively, from 0.1 hours to 48 hours; alternatively, from 0.25 hours to 36 hours; alternatively, from 0.4 hours to 36 hours; alternatively, from 0.5 hours to 24 hours; or alternatively, from 0.5 hours to 24 hours. Other chromium(III) halide hydrate, the water absorption agent, and the coordinating compound contact time ranges are readily apparent from the present disclosure.

In an aspect, a continuous process for preparing a chromium(III) halide complex can comprise flowing a mixture comprising 1) a chromium(III) halide hydrate and 2) a coordinating compound, L, through a bed comprising a solid water absorption agent to form a chromium(III) halide complex having the formula $CrX_3 \cdot mL$. In an embodiment, the continuous process for preparing a chromium(III) halide complex can comprise: flowing a mixture comprising 1) a chromium(III) halide hydrate and 2) a coordinating compound, L, through a bed comprising a solid water absorption agent to form a solution comprising, or consisting essentially of, a chromium(III) halide complex having the formula $CrX_3 \cdot mL$ and the coordinating compound. In a non-limiting aspect, a continuous process for preparing a chromium(III) chloride complex can comprise flowing a mixture comprising 1) a chromium(III) chloride hydrate and 2) a coordinating compound, L, through a bed comprising a solid water absorption agent to form a chromium(III) chloride complex having the formula $CrCl_3 \cdot mL$. In an embodiment, the continuous process for preparing a chromium(III) halide complex can comprise: flowing a mixture comprising 1) a chromium(III) chloride hydrate and 2) a coordinating compound, L, through a bed comprising a solid water absorption agent to form a solution comprising, or consisting essentially of, a chromium (III) chloride complex having the formula $CrX_3 \cdot mL$ and the coordinating compound. In another non-limiting aspect, a continuous process for preparing $CrCl_3(THF)_3$ can comprise flowing a mixture comprising 1) a chromium(III) chloride hydrate and 2) tetrahydrofuran through a bed comprising a 3 Å, 4 Å, 5 Å, 10×, or 13× molecular sieve to form $CrCl_3$ $(THF)_3$. In an embodiment, the continuous process for preparing a chromium(III) halide complex can comprise: flowing a mixture comprising 1) a chromium(III) chloride hydrate and 2) tetrahydrofuran through a bed comprising a 3 Å, 4 Å, 5 Å, 10×, or 13× molecular sieve to form a solution comprising, or consisting essentially of, $CrCl_3(THF)_3$. In an embodiment, the solution can comprise or consist essentially of a chromium chromium(III) halide complex having the formula $CrX_3 \cdot mL$, the coordinating compound, and the solid water absorption agent. Aspects and embodiments of the continuous fixed bed process are independently described herein.

These independently described aspects and embodiments can be combined in any conceivable fashion to further describe a continuous fixed bed process for preparing a chromium(III) halide complex. Additionally, aspects and embodiments of the chromium(III) halide hydrate, the water absorption agent, the coordinating compound, and the chromium(III) halide complex are independently described herein and these aspects and embodiments can be utilized without limitation to further describe a continuous fixed bed process for preparing a chromium(III) halide complex.

In an embodiment, the minimum quantity of coordinating compound, L, utilized in the contacting to form step of any process describe herein can be at least 1%, 5%, 25%, 50%, 75%, or 100% in excess of the molar quantity necessary to produce the chromium(III) halide complex, $CrX_3 \cdot mL$, from the utilized chromium(III) halide hydrate. In an embodiment, the maximum quantity of coordinating compound, L, utilized in the contacting to form step of any process described herein can be 5,000%, 2,500%, 1,000%, 750%, 500%, 250%, 100%, 75%, 50%, or 25% in excess of the molar quantity necessary to produce the chromium(III) halide complex, $CrX_3 \cdot mL$, from the utilized chromium(III) halide hydrate. In some embodiments, the quantity of coordinating compound, L, utilized in the contacting to form step of any process describe herein can range from a minimum molar quantity disclosed herein to any maximum molar quantity described herein. In some non-limiting embodiments, the quantity of coordinating compound, L, utilized in the contacting to form step of any process describe herein can be from 1% in excess of the molar quantity necessary to produce the chromium(III) halide complex to 5000% in excess of the molar quantity necessary to produce the chromium(III) halide complex; alternatively, from 25% in excess of the molar quantity necessary to produce the chromium(III) halide complex to 5000% in excess of the molar quantity necessary to produce the chromium(III) halide complex; or alternatively, from 1% in excess of the molar quantity necessary to produce the chromium(III) halide complex to 500% in excess of the molar quantity necessary to produce the chromium(III) halide complex. Other ranges of coordinating compound, L, are readily apparent from the present disclosure.

In some embodiments, the minimum quantity of the coordinating compound, L, utilized in the contacting to form step of any process described herein can be at least 1%, 5%, 25%, 50%, 70%, 90% 100%, or 125%, by volume, in excess of the volumetric quantity necessary to dissolve the utilized chromium(III) halide hydrate. In an embodiment, the maximum quantity of coordinating compound, L, utilized in the contacting to form step of any process described herein can be 5,000%, 2,500%, 1,000%, 750%, 500%, 250%, 100%, 75%, 50%, or 25%, by volume, in excess of the volumetric quantity necessary to produce the chromium(III) halide complex, $CrX_3 \cdot mL$, from the utilized chromium(III) halide hydrate. In some embodiments, the quantity of coordinating compound, L, utilized in the contacting to form step of any process describe herein can range from a minimum volumetric quantity disclosed herein to any maximum volumetric quantity described herein. In some non-limiting embodiments, the quantity of coordinating compound, L, utilized in the contacting to form step of any process describe herein can be from 1%, by volume, in excess of the volumetric quantity necessary to dissolve the utilized chromium(III) halide hydrate 5000%, by volume, in excess of the volumetric quantity necessary to dissolve the utilized chromium(III) halide hydrate; alternatively, from 25%, by volume, in excess of the volumetric quantity necessary to dissolve the utilized chromium(III)

halide hydrate 5000%, by volume, in excess of the volumetric quantity necessary to dissolve the utilized chromium(III) halide hydrate; or alternatively, from 25%, by volume, in excess of the volumetric quantity necessary to dissolve the utilized chromium(III) halide hydrate 500%, by volume, in excess of the volumetric quantity necessary to dissolve the utilized chromium(III) halide hydrate. Other ranges of coordinating compound, L, are readily apparent from the present disclosure.

In an aspect, the formation of the chromium(III) halide hydrate can be performed in a solvent comprising, or consisting essentially of, the coordinating compound.

In an embodiment, the chromium(III) halide hydrate can be at least partially soluble in a solvent comprising, or consisting essentially of, the coordinating compound. Thus, it is not necessary that the chromium(III) halide hydrate starting compound be highly soluble in the solvent comprising, or consisting essentially of, the coordinating compound, although high solubility of the chromium(III) halide hydrate can be possible. In an embodiment, the quantity solvent comprising, or consisting essentially of, the coordinating compound can be made such that the chromium(III) halide hydrate can be completely dissolved; or alternatively, the quantity solvent comprising, or consisting essentially of, the coordinating compound can be made such that the chromium(III) halide hydrate may not be completely dissolved. Consequently, in some embodiments, all or part of the formation of the $CrX_3.nH_2O$ can occur in a slurry of the chromium(III) halide hydrate.

In an embodiment, the quantity of solvent comprising, or consisting essentially of, the coordinating compound can be such that the formed chromium(III) halide complex can be completely dissolved; or alternatively, the quantity of solvent comprising, or consisting essentially of, the coordinating compound can be such that the formed chromium(III) halide may not be completely dissolved. Consequently, in some embodiments, the formed chromium(III) halide complex, $CrX_3.mL$, can precipitate during formation of the chromium (III) halide complex. Therefore, the contacting to form step can provide a solution which can be a slurry of the chromium (III) halide complex, $CrX_3.mL$, in a solvent comprising, or consisting essentially of, the coordinating compound; or alternatively, provide a solution in which the chromium(III) halide complex, $CrX_3.mL$, is dissolved in the a solvent comprising, or consisting essentially of, the coordinating compound.

In an aspect, the chromium(III) halide complex can be formed under conditions capable of forming the chromium (III) halide complex, $CrX3.mL$. Conditions capable of forming the chromium(III) halide complex can include, temperature, pressure, contact mixture agitation (or lack thereof), chromium(III) halide hydrate to water absorption agent, WHSV (weight hourly space velocity), among other conditions. These chromium(III) halide complex formation conditions are independently described herein and can be utilized in any combination to further describe a process for producing a chromium(III) halide complex.

In an aspect, a contact mixture comprising the chromium (III) halide hydrate, the water absorption agent, and the coordinating compound, L, can be agitated; alternatively, a contact mixture comprising the chromium(III) halide hydrate, the water absorption agent, and the coordinating compound, L, may not be agitated. In an embodiment, a contact mixture comprising the chromium(III) halide hydrate, the water absorption agent, and the coordinating solvent, L, can be agitated for all or any portion of the time for which the chromium(III) halide hydrate, the water absorption agent, and the coordinating compound, L, are contacted. Contact times for the chromium(III) halide hydrate, the water absorption agent, and the coordinating compound are provided herein. Any contact time which represents all or a portion of a utilized contact time can be utilized as the time period under which a contact mixture comprising the chromium(III) halide hydrate, the water absorption agent, and the coordinating compound can be agitated.

In an aspect, the quantity of water absorption agent utilized can have a water absorption capacity greater than the quantity of water in the amount of chromium(III) halide hydrate that is used as the starting material. For example, when the process of this disclosure is performed in a batch process, a quantity of water absorption agent having a greater water absorption capacity than the quantity of water in the amount of chromium(III) halide hydrate is contacted with the chromium(III) halide hydrate so that the desired chromium(III) halide complex $CrX_3.mL$ having any desired water content (e.g., a substantially anhydrous chromium(III) halide complex among other possibilities) can be produced in good yield from a single batch treatment. When the process of this disclosure is effected in a flow or continuous process, by using a quantity of water absorption agent having a greater water absorption capacity than the quantity of water in the sample of chromium (III) halide hydrate, the flow process can effectively be used to prepare the desired chromium(III) halide complex $CrX_3.mL$ having any desired water content (e.g., a substantially anhydrous chromium(III) halide complex among other possibilities) can be produced from the effluent of the flow process, without additional drying steps. In the flow process, a quantity of water absorption agent can be chosen to provide a desired time of operation before it is no longer effective at producing the chromium(III) halide complex $CrX_3.mL$ having any desired water content (e.g., a substantially anhydrous chromium(III) halide complex among other possibilities). In such a scenario, the water content of the effluent of the flow reactor can be monitored to determine when the water absorption agent can be replaced or regenerated.

In an aspect, a condition capable of forming the chromium (III) halide complex can include a chromium(III) halide complex formation time. In an aspect, the chromium(III) halide complex formation time can include all or a portion of the time for which the chromium(III) halide hydrate, the water absorption agent, and the coordinating compound, L, are contacted as described herein. In an embodiment, a condition capable of forming the chromium(III) halide complex can include a chromium(III) halide complex formation time of at least 0.1 hours; alternatively, at least 0.15 hours; alternatively, at least 0.2 hours; alternatively, at least 0.25 hours; alternatively, at least 0.3 hours; alternatively, at least 0.35 hours; alternatively, at least 0.45, hours; or alternatively, at least 0.5 hours. In an embodiment, the maximum chromium(III) halide complex formation time can be 72 hours; alternatively, 48 hours; alternatively, 36 hours; alternatively, 24 hours; alternatively, 18 hours; alternatively, 15 hours; alternatively, 12 hours; alternatively, 9 hours; alternatively, 8 hours; or alternatively, 7 hours. In some embodiments, a condition capable of forming the chromium(III) halide complex can include a chromium(III) halide complex formation time that can range from any minimum chromium(III) halide complex formation time disclosed herein to any maximum chromium (III) halide complex formation time described herein. In some non-limiting embodiments, a condition capable of forming the chromium(III) halide complex can include a chromium (III) halide complex formation time from 0.1 hours to 72 hours; alternatively, from 0.1 hours to 48 hours; alternatively, from 0.25 hours to 36 hours; alternatively, from 0.4 hours to 36 hours; alternatively, from 0.5 hours to 24 hours; or alternatively, from 0.5 hours to 24 hours. Other chromium(III) halide complex formation time ranges are readily apparent from the present disclosure.

In an aspect, the chromium(III) halide complex can be formed at any temperature capable of forming the chromium (III) halide complex. In an embodiment, a condition capable of forming the chromium(III) halide complex can include ambient temperature (i.e., 15° C. to 35° C. wherein no external heat or cooling source is directly applied as defined herein). In some embodiments, a condition capable of forming the chromium(III) halide complex can include cooling the contact mixture comprising the comprising the chromium (III) halide hydrate, the water absorption agent, and the coordinating compound; or alternatively, can include heating the contact mixture comprising the comprising the chromium (III) halide hydrate, the water absorption agent, and the coordinating compound. In other embodiments, a condition capable of forming the chromium(III) halide complex can include a temperature from −10° C. to 200° C.; alternatively, from −5° C. to 175° C.; alternatively, from 0° C. to 150° C.; alternatively, from 5° C. to 125° C.; alternatively, from 10° C. to 100° C.; alternatively, from 15° C. to 75° C.; or alternatively 15° C. to 60° C. It should be noted that the temperature at which the chromium(III) halide hydrate, the water absorption agent, and the coordinating compound are contacted and the temperature capable of forming the chromium(III) halide complex, can be the same; or alternatively, can be different. It should be also noted that the chromium(III) halide hydrate, the water absorption agent, and the coordinating compound can be contacted at one temperature (one at which the formation of the chromium(III) halide complex can slowly form) and then the mixture subjected to a second temperature formation of the chromium(III) halide complex. Temperatures above the atmospheric boiling point of the coordinating compound can be utilized by forming the chromium(III) halide complex at a pressure that maintains the coordinating solvent in a liquid state.

In an aspect, the chromium(III) halide complex can be formed at any pressure capable of forming the chromium(III) halide complex. In an embodiment, the conditions capable of forming the chromium(III) halide complex can include atmospheric pressure (i.e., about 14.7 psi or about 101 kPa). In an embodiment, a condition capable of forming the chromium (III) halide complex can include subjecting the contact mixture comprising the comprising the chromium(III) halide hydrate, the water absorption agent, and the coordinating compound to a pressure greater than ambient pressure. In some embodiments, a condition capable of forming the chromium(III) halide complex can include a pressure of at least atmospheric pressure; alternatively, at least 2 psi (14 kPa) greater than atmospheric pressure; alternatively, least 5 psi (34 kPa) greater than atmospheric pressure; alternatively, least 10 psi (69 kPa) greater than atmospheric pressure; or alternatively, least 15 psi (103 kPa) greater than atmospheric pressure. In some embodiments, a condition capable of forming the chromium(III) halide complex can include a pressure capable of maintaining the coordinating compound (and/or the solvent) in the liquid state; alternatively, at least 2 psi (14 kPa) greater than the pressure capable of maintaining the coordinating compound (and/or the solvent) in the liquid state; alternatively, at least 5 psi (34 kPa) greater than the pressure capable of maintaining the coordinating compound (and/or the solvent) in the liquid state; alternatively, at least 10 psi (69 kPa) greater than the pressure capable of maintaining the coordinating compound (and/or the solvent) in the liquid state; or alternatively, least at 15 psi (103 kPa) greater than the pressure capable of maintaining the coordinating compound (and/or the solvent) in the liquid state. In other embodiments, a condition capable of forming the chromium(III) halide complex can include a maximum pressure of 500 psi (3.4 mPa); alternatively, of 400 psi (2.8 mPa); alternatively, of 250 psi (1.7 mPa); alternatively, of 200 psi (1.4 mPa); alternatively, of 150 psi (1.0 mPa); alternatively, of 100 psi (689 kPa); or alternatively, of 50 psi (345 kPa). In yet other embodiments, a condition capable of forming the chromium (III) halide complex can include a pressure that can range from any minimum chromium(III) halide complex formation pressure disclosed herein to any maximum chromium(III) halide complex formation pressure described herein. In some non-limiting embodiments, a condition capable of forming the chromium(III) halide complex can include a pressure from atmospheric pressure to 500 psi (3.4 mPa); alternatively, at least 2 psi (14 kPa) greater than atmospheric pressure to 500 psi (3.4 mPa); alternatively, at least 5 psi (34 kPa) greater than the pressure capable of maintaining the coordinating compound (and/or the solvent) in the liquid state to 500 psi (3.4 mPa). Other pressure ranges which can be a condition capable of forming the chromium(III) halide complex are readily apparent from the present disclosure.

According to another aspect of this disclosure, the chromium(III) halide complex can be formed by flowing a mixture comprising, or consisting essentially of, 1) a chromium (III) halide hydrate and 2) a coordinating compound through a bed of the water absorption agent. In some embodiments, the both materials can be introduced at the base of the bed of water absorption agent. Generally, the base of the bed of water absorption agent can be the first point in the based at which at least one of either the chromium(III) halide hydrate or the coordinating compound contact the bed of water absorption agent regardless of the direction of flow (up, down, horizontal, or other) through the bed of water absorption agent. In some embodiments, one reagent can be contacted at the base of the bed of water absorption agent and the other agent at a point beyond the base of the water absorption agent. In an non-limiting embodiment, the coordinating compound can be introduced at the base of the bed of water absorption agent while a solution (or slurry) comprising, or consisting of, the chromium(III) halide hydrate and a solvent can be introduced at a point beyond the base of the bed of water absorption agent; or alternatively, a solution (or slurry) comprising, or consisting of, the chromium(III) halide hydrate and a solvent can be introduced at the base of the bed of water absorption agent while the coordinating compound can be introduced at a point beyond the base of the bed of water absorption agent. In another embodiments, the coordinating compound can be introduced at the base of the bed of water absorption agent while a solution (or slurry) comprising, or consisting of, the chromium(III) halide hydrate the coordinating compound can be introduced at a point beyond the base of the bed of water absorption agent; or alternatively, a solution (or slurry) comprising, or consisting of, the chromium (III) halide hydrate and the coordinating solvent can be introduced at the base of the bed of water absorption agent while the coordinating compound can be introduced at a point beyond the base of the bed of water absorption agent.

According to another aspect of this disclosure, the chromium(III) halide complex can be formed by flowing a mixture comprising, or consisting essentially of, 1) a chromium (III) halide hydrate and 2) a coordinating compound through a bed of the water absorption agent. Generally, the mixture can be a slurry or a homogenous mixture; alternatively a slurry; or alternatively a homogenous mixture. It should be noted that, it is not necessary that the bed of the water absorption agent encompass or cover the entire cross-sectional area perpendicular to the flow vector of the mixture comprising, or consisting essentially of, the chromium(III) halide hydrate and the coordinating compound, such as passing the mixture comprising, or consisting essentially of, the chromium(III) halide hydrate and the coordinating compound down or up a column of the water absorption agent. In an embodiment, the mixture comprising, or consisting essentially of, the chromium(III) halide hydrate and the coordinating compound can flow up a column of the water absorption agent; alternatively, the mixture comprising, or consisting essentially of, the chromium(III) halide hydrate and the coordinating compound can flow down an column of the water absorption agent; or alternatively, the mixture comprising, or consisting essentially of, the chromium(III) halide hydrate and the coordinating compound can flow horizontally across a bed of water absorption agent. In other embodiment, the mixture comprising, or consisting essentially of, the chromium(III) halide hydrate and the coordinating compound can flow through a column of water absorption agent at any angle between horizontal and vertical (either in a upward or downward direction). In an embodiment, a minimum chromium(III) halide hydrate to water adsorption agent WHSV at which the chromium(III) halide hydrate may flow through the water adsorption agent can be 0.01; alternatively, 0.05; alternatively, 0.1; alternatively, 0.15; alternatively, 0.2; alternatively, 0.25; alternatively, 0.3; alternatively, 0.4; or alternatively, 0.5. In an embodiment, a maximum chromium(III) halide hydrate to water adsorption agent WHSV at which the chromium(III) halide hydrate may flow through the water adsorption agent can be 10; alternatively, 9; alternatively, 8; alternatively, 7; alternatively, 6; alternatively, 5; alternatively, 4; alternatively, 3; alternatively, 2; or alternatively, 1. In some embodiments, chromium(III) halide hydrate to water adsorption agent WHSV at which the chromium(III) halide hydrate may flow through the water adsorption agent can range from any minimum chromium(III) halide hydrate to water adsorption agent WHSV disclosed herein to any maximum minimum chromium(III) halide hydrate to water adsorption agent WHSV described herein. In a non-limiting embodiment, the chromium(III) halide hydrate to water adsorption agent WHSV can be from 0.01 to 9.0; alternatively, from 0.05 to 2; alternatively, from 0.01 to 5; alternatively, from 0.05 to 2; or alternatively, from 0.1 to 2. Other chromium(III) halide hydrate to water adsorption agent WHSV ranges are readily apparent from the present disclosure.

In an aspect, the process for producing the chromium(III) halide complex can produce a solution or a slurry of the chromium(III) halide complex having the formula $CrX_3.mL$, which can be used (or stored and then used) without a separate or discrete isolation step. In an aspect and any disclosed embodiment, the chromium(III) halide complex, $CrX_3.mL$, can be isolated; alternatively, the chromium(III) halide complex, $CrX_3.mL$, can be purified; or alternatively, the chromium(III) halide complex, $CrX_3.mL$ can be isolated and purified. In another, aspect and in any disclosed embodiment, the chromium(III) halide complex, $CrX_3.mL$, prepared as disclosed can be used without further purification and/or without isolating the chromium(III) halide complex.

In a non-limiting aspect and any embodiment disclosed herein, a process for preparing a chromium(III) halide complex can comprise: a) contacting 1) a chromium(III) halide hydrate, 2) a water absorption agent, and 3) a coordinating compound, L, to forming a chromium (III) halide complex having the formula $CrX_3.mL$; and b) isolating the chromium (III) halide complex. In another non-limiting aspect and any embodiment disclosed herein, a process for preparing a chromium(III) halide complex can comprise: a) contacting 1) a chromium(III) halide hydrate, 2) a water absorption agent, and 3) a coordinating compound, L, to forming a chromium (III) halide complex having the formula $CrX_3.mL$; b) isolating the chromium(III) halide complex; and c) purifying the isolated chromium(III) halide complex. In some embodiments, the isolated chromium(III) halide complex can be substantially anhydrous; alternatively, can be anhydrous; or alternatively, can have any water content disclosed herein.

In an embodiment, a solution comprising the formed chromium(III) halide complex, $CrX_3.mL$, can be filtered. The filtering can be performed to remove particles of the water absorption agent, insoluble chromium compounds, and/or other particulate matter. In other embodiments, a discrete filtering step may be unnecessary. For example, when the process of this disclosure is practiced in a flow process, the effluent from the flow process can constitute a solution that may not require a filtering step. Whether or not the chromium (III) halide complex solution requires filtering can be dependent upon whether the chromium(III) halide complex solution contains water absorption agent particles, insoluble chromium compounds, and/or other particulate matter.

In an aspect and any disclosed embodiment, the chromium halide complex, $CrX_3.mL$, can be isolated from a solution comprising the chromium halide complex by any one of: a) concentrating the chromium(III) halide complex solution, b) cooling the chromium(III) halide complex solution, c) contacting the chromium(III) halide complex solution with a non-coordinating solvent, or d) any combination thereof. Therefore, in this aspect, the chromium(III) halide complex $CrX_3.mL$ can be isolated by filtering the solution of the chromium(III) halide complex in the coordinating solvent and carrying out any of the steps of: 1) concentrating the chromium(III) halide complex solution; 2) cooling the chromium (III) halide complex solution; 3) contacting the chromium (III) halide complex solution with a non-coordinating solvent; 4) a combination of concentrating the chromium(III) halide complex solution and cooling the solution; 5) a combination of concentrating the chromium(III) halide complex solution and contacting the solution with a non-coordinating solvent; 6) a combination of cooling the chromium(III) halide complex solution and contacting the solution with a non-coordinating solvent; and 7) a combination of concentrating the chromium(III) halide complex solution, cooling the solution, and contacting the solution with a non-coordinating solvent. In each of these instances, the step, or combination of steps, can produce a precipitate (or can cause the chromium (III) halide complex to crystallize). The chromium(III) halide complex can then be separated from the liquid by filtration.

In some embodiments, the solution comprising the chromium halide complex, $CrX_3.mL$, can be filtered prior to isolating the chromium halide complex, $CrX_3.mL$, from the solution. In other embodiments, the chromium halide complex can be isolated from an unfiltered solution comprising the chromium halide complex. Whether or not the chromium (III) halide complex solution requires filtering can be dependent upon whether the chromium(III) halide complex solution contains water absorption agent particles, insoluble chromium compounds, and/or other particulate matter.

In an aspect, a process for preparing a chromium(III) halide complex can further comprise any one of i) concentrating the chromium(III) halide complex solution, ii) cooling the chromium(III) halide complex solution, iii) contacting the chromium(III) halide complex solution with a non-coordinating solvent, or any combination of i), ii), and/or iii). In another aspect, a process for preparing a chromium(III) halide complex can further comprise filtering a solution comprising the chromium(III) halide complex and any one of i) concentrating the chromium(III) halide complex solution, ii) cooling the chromium(III) halide complex solution, iii) contacting the chromium(III) halide complex solution with a non-coordinating solvent, or any combination of i), ii), and/or iii).

In an aspect and any embodiment disclosed herein, the chromium(III) halide complex, $CrX_3.mL$, can be purified. In an embodiment, the chromium(III) halide complex can be dissolved in a solvent to form a solution, the solution filtered to remove insoluble materials and the chromium(III) halide complex isolated by any one of i) concentrating the chromium(III) halide complex solution, ii) cooling the chromium(III) halide complex solution, iii) contacting the chromium(III) halide complex solution with a non-coordinating solvent, or any combination of i), ii), and/or iii). Generally, the solvent in which the chromium(III) halide complex is dissolved can be, comprise, or consist essentially of, the coordinating ligand (also referred to as the coordinating compound) of the chromium(III) halide complex, a non-coordinating solvent, or any combination thereof; alternatively, the coordinating ligand of the chromium(III) halide complex; or alternatively, a non-coordinating solvent.

In an embodiment, the chromium(III) halide complex can be purified by recrystallization. In some embodiments, the chromium(III) halide complex recrystallization solvent can be, comprise, or consist essentially of, the coordinating ligand (also referred to as the coordinating compound) of the chromium(III) halide complex, a non-coordinating solvent, or any combination thereof; alternatively, the coordinating ligand of the chromium(III) halide complex; or alternatively, a non-coordinating solvent. The process of recrystallization In an embodiment, methods for purifying the chromium(III) halide complex, $CrX_3.mL$, can use the coordinating ligand, L, of the chromium(III) halide complex as the solvent for dissolving the chromium(III) halide complex. Generally, the coordinating ligand solvent, L, can be the same as the coordinating ligand of the chromium(III) halide complex, $CrX_3.mL$, being purified. Coordinating compounds (also referred to as coordinating ligands) are described herein and can be utilized without limitation in the methods for purifying the chromium(III) halide complex.

In an embodiment, methods for purifying the chromium(III) halide complex, $CrX_3.mL$, can use a non-coordinating solvent for dissolving the chromium(III) halide complex. Generally, the non-coordinating solvent can be, comprise, or consist essentially of, any non-coordinating solvent which can dissolve the chromium(III) halide complex under the conditions utilized for the purification. In some embodiments, the non-coordinating solvent can be, comprise, or consist essentially of, a halogenated hydrocarbon. Halogenated hydrocarbon solvents are independently described herein and can be utilized without limitation to describe a method of purifying the chromium(III) halide complex.

In an embodiment, method for isolating and/or purifying the chromium(III) halide complex, $CrX_3.mL$, can contact the chromium(III) halide complex solution with a non-coordinating solvent.

Generally, the non-coordinating solvent can be, comprise, or consist essentially of, any non-coordinating solvent which can cause the chromium(III) halide complex to precipitate under conditions utilized for the isolation or purification. In some embodiments, the non-coordinating solvent can be, comprise, or consist essentially of, a hydrocarbon, a halogenated hydrocarbon, or any combination thereof; alternatively, a hydrocarbon; or alternatively, a halogenated hydrocarbon. Hydrocarbon solvents and halogenated hydrocarbon solvents are independently described herein and can be utilized without limitation to describe a method of purifying the chromium(III) halide complex.

In an embodiment, a solution consisting essentially of the chromium(III) halide complex and the coordinating compound can be substantially anhydrous; or alternatively, anhydrous. In an embodiment, a solution consisting essentially of the chromium(III) halide complex, the coordinating compound, and a solvent can be substantially anhydrous; or alternatively, anhydrous. In other embodiments, a solution consisting essentially of the chromium(III) halide complex, the coordinating compound, and optionally a solvent can have a water content less than or equal to 100 ppm, such as for example, less than or equal to 90 ppm; alternatively, less than or equal to 80 ppm; alternatively, less than or equal to 70 ppm; alternatively, less than or equal to 60 ppm; alternatively, less than or equal to 50 ppm; alternatively, less than or equal to 40 ppm; alternatively, less than or equal to 30 ppm; alternatively, less than or equal to 20 ppm; alternatively, less than or equal to 10 ppm; alternatively, less than or equal to 9 ppm; alternatively, less than or equal to 8 ppm; alternatively, less than or equal to 7 ppm; alternatively, less than or equal to 6 ppm; alternatively, less than or equal to 5 ppm; alternatively, less than or equal to 4 ppm; alternatively, less than or equal to 3 ppm; alternatively, less than or equal to 2 ppm; alternatively, less than or equal to 1 ppm; or alternatively, less than or equal to 0.5 ppm. Generally, the water content of a solution consisting essentially of the chromium(III) halide complex, the coordinating compound, and optionally a solvent is based upon the weight percentage of water in the solution. It should be noted that the water present in the solution can be in the form of a chromium(III) halide hydrate impurity and/or free water.

In an embodiment, an isolated (and/or purified) chromium(III) halide complex can be substantially anhydrous; or alternatively, anhydrous. In an embodiment, an isolated (and/or purified) chromium(III) halide complex can have a water content less than or equal to 100 ppm, such as for example, less than or equal to 90 ppm; alternatively, less than or equal to 80 ppm; alternatively, less than or equal to 70 ppm; alternatively, less than or equal to 60 ppm; alternatively, less than or equal to 50 ppm; alternatively, less than or equal to 40 ppm; alternatively, less than or equal to 30 ppm; alternatively, less than or equal to 20 ppm; alternatively, less than or equal to 10 ppm; alternatively, less than or equal to 9 ppm; alternatively, less than or equal to 8 ppm; alternatively, less than or equal to 7 ppm; alternatively, less than or equal to 6 ppm; alternatively, less than or equal to 5 ppm; alternatively, less than or equal to 4 ppm; alternatively, less than or equal to 3 ppm; alternatively, less than or equal to 2 ppm; alternatively, less than or equal to 1 ppm; or alternatively, less than or equal to 0.5 ppm. Generally, the water content of an isolated (and/or purified) chromium(III) halide complex can be based upon the weight percentage of water in the isolated (and/or purified) chromium(III) halide complex. It should be noted that the water present in the isolated (and/or purified) chromium(III) halide complex can be in the form of a chromium(III) halide hydrate impurity and/or interstitial water.

According to a further aspect, the water absorption agent used in the disclosed process can be activated prior to use. For example, some water absorption agents can have a certain amount of absorbed water already present when they are obtained, such as from a commercial source. Therefore, it can be helpful to activate the water absorption agent or agents before they are utilized. In another aspect of this disclosure, the water absorption agent can be regenerated after it has been utilized in the processes described herein.

One aspect of the present disclosure encompasses the use of molecular sieves as the water absorption agent. In this aspect and in any embodiment, the water absorption agent can be activated prior to use; alternatively, regenerated between uses. The water absorption agent can be activated by heating, by heating with gas purging, by heating under vacuum, by exposing the water absorption agent to microwave radiation, by exposing the water absorption agent to microwave radiation with gas purging, or by exposing the water absorption agent to microwave radiation under vacuum prior to the contacting step; alternatively, by heating, by heating with gas purging, or by heating under vacuum; alternatively, by exposing the water absorption agent to microwave radiation, by exposing the water absorption agent to microwave radiation with gas purging, or by exposing the water absorption agent to microwave radiation under vacuum prior to the contacting step; alternatively, by heating; alternatively, by heating with gas purging; alternatively, by heating under vacuum; alternatively, by exposing the water absorption agent to microwave radiation; alternatively, by exposing the water absorption agent to microwave radiation with gas purging; or alternatively, by exposing the water absorption agent to microwave radiation under vacuum prior to the contacting step. These same activating methods can be useful in regenerating the water absorption agent so that it can be reused numerous times. For example, in any embodiment disclosed herein, the water absorption agent can be a 3 Å molecular sieve, a 4 Å molecular sieve, a 5 Å molecular sieve, a 10× molecular sieve, or a 13× molecular sieve, and these molecular sieves can be activated initially by any of these methods, and these molecular sieves can be reactivated and reused/recycled following their initial use by any of these methods.

Typical gases that can be used in any water absorption agent activation or regeneration utilizing gas purging include inert gases such as nitrogen, helium, argon, neon, or any combination thereof. Alternatively, nitrogen can be utilized as the gas for activating or regenerating the water absorption agent utilizing gas purging. In some embodiments, dry air can be utilized as the gas for activating or regenerating the water absorption agent utilizing gas purging.

Generally, the water absorption agent can be regenerated utilizing any temperature capable of regenerating the water absorption agent. In any embodiment utilizing heating of the water absorption agents, the minimum heating temperature utilized to activate or regenerate the water absorption agent can be 40° C.; alternatively, 50° C.; alternatively, 60° C.; alternatively, 70° C.; alternatively, 80° C.; alternatively, 90° C.; alternatively, 100° C.; alternatively, 125° C.; alternatively, 150° C.; alternatively, 175° C.; alternatively, 200° C.; alternatively, 225° C.; or alternatively, 250° C. In any embodiment utilizing heating of the water absorption agents, the maximum heating temperature utilized to activate or regenerate the water absorption agent can be 600° C.; alternatively, 575° C.; alternatively, 550° C.; alternatively, 525° C.; alternatively, 500° C.; alternatively, 475° C.; alternatively, 450° C.; alternatively, 425° C.; alternatively, 400° C.; alternatively, 375° C.; alternatively, 350° C.; alternatively, 325° C.; or alternatively, 300° C. In some embodiments, the heating temperature utilized to activate or regenerate the water absorption agent can range from any minimum heating temperature disclosed herein to any maximum heating temperature described herein. In some non-limiting embodiments, the heating temperature utilized to activate or regenerate the water absorption agent can be from 40° C. to 600° C.; alternatively, from 50° C. to 575° C.; alternatively, from 60° C. to 550° C.; alternatively, from 70° C. to 525° C.; alternatively, from 80° C. to 500° C.; alternatively, from 90° C. to 475° C.; alternatively, from 100° C. to 450° C.; alternatively, from 125° C. to 425° C.; alternatively, from 150° C. to 400° C.; alternatively, from 175° C. to 375° C.; alternatively, from 200° C. to 350° C.; alternatively, from 225° C. to 325° C.; or alternatively, from 250° C. to 300° C. Other heating temperature ranges utilized to activate or regenerate the water absorption agent are readily apparent from the present disclosure. Moreover, in some embodiments, multiple heating steps can be utilized and each heating step can be performed at a different temperature and/or other condition (e.g., gas purging or exposure to vacuum).

Generally, when a vacuum is utilized, the water absorption agent can be regenerated utilizing any vacuum capable of regenerating the water absorption agent. In any embodiment utilizing exposing the water absorption agent to vacuum, the minimum vacuum utilized to activate or regenerate the water absorption agent can be 100 Torr; alternatively, 75 Torr; alternatively, 50 Torr; alternatively, 25 Torr; alternatively, 10 Torr; alternatively, 5 Torr; alternatively, 1 Torr; alternatively, $5 \times 10^{-1}$ Torr; alternatively, $1 \times 10^{-1}$ Torr; alternatively, $5 \times 10^{-2}$ Torr; or alternatively, $1 \times 10^{-2}$ Torr. In any embodiment utilizing exposing the water absorption agent to vacuum, the maximum vacuum utilized to activate or regenerate the water absorption agent can be $1 \times 10^{-5}$ Torr; alternatively $1 \times 10^{-3}$ Torr; alternatively, $5 \times 10^{-3}$ Torr; alternatively, $1 \times 10^{-3}$ Torr; alternatively $5 \times 10^{-2}$ Torr; or alternatively, $1 \times 10^{-2}$ Torr. In some non-limiting embodiments, the vacuum utilized to activate or regenerate the water absorption agent can be from 100 Torr to $1 \times 10^{-5}$ Torr; alternatively, from 10 Torr to $5 \times 10^{-4}$ Torr; alternatively, from 1 Torr to $10^{-4}$ Torr; alternatively, from $10^{-1}$ Torr to $5 \times 10^{-3}$ Torr; or alternatively, from $10^{-2}$ Torr to $10^{-3}$ Torr. Other vacuum ranges utilized to activate or regenerate the water absorption agent are readily apparent from the present disclosure. Moreover, in some embodiments, multiple vacuum steps can be utilized and each vacuum step can be performed at a different temperature and/or other condition described herein.

In any embodiment utilizing exposing the water absorption agent to microwave radiation, the conditions generally can use an effective combination of time of exposure to the microwave and microwave power. In this aspect and generally, the useful of microwave radiation power and the time of exposure to the microwave radiation can be easily determined, typically with less time being needed when using higher microwave power, and more time being needed with using lower microwave power. The most useful microwave power and time of exposure parameters also are correlated to the amount of sample being activated, with higher power, more exposure time, or a combination of these typically be used for larger samples of the water absorption agent being activated. Using molecular sieves as an example, one method of checking the progress of the molecular sieve activation by microwave radiation is to expose the sample to microwave radiation at a specified power and for a specific period of time, and then insert a temperature measuring device (e.g., thermocouple or thermometer) into the sample and allow it to come to temperature. Molecular sieves that are activated by microwave radiation also can be observed to glow red when they have reached a certain temperature, indicating a certain temperature and level of activation associated with that temperature.

An additional aspect of this disclosure provides that the same methods used to activate the water absorption agents such as molecular sieves, before their initial use, also can be used to re-activate or re-generate the water absorption agents after their first use or any subsequent use. Accordingly, these same methods can be employed to activate and/or regenerate the water absorption agents. This aspect of the present disclosure provides a convenient, cost-effective, and recyclable method for carrying out the synthesis described herein. Moreover, the recyclable aspect provides an advantage over the single-use and/or stoichiometric drying reagents.

Various aspect and embodiments described herein refer to non-hydrogen substituents such as halogen (or halo, halide), hydrocarbyl, hydrocarboxy, alkyl, and/or alkoxy substituents, among others. The non-hydrogen substituents of any aspect or embodiment calling for a substituent can be a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group. In other embodiments, the non-hydrogen substituents of any aspect or embodiment calling for a substituent can be a halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group; alternatively, a halide; alternatively, a $C_1$ to $C_5$ hydrocarbyl group; or alternatively, a $C_1$ to $C_5$ hydrocarboxy group.

In an embodiment, any halide substituent of any aspect or embodiment calling for a substituent can be a fluoride, chloride, bromide, or iodide; alternatively, a fluoride or chloride. In some embodiments, any halide substituent of any aspect or embodiment calling for a substituent can be a fluoride; alternatively, a chloride; alternatively, a bromide; or alternatively, an iodide.

In an embodiment, any hydrocarbyl substituent can be an alkyl group, an aryl group, or an aralkyl group; alternatively, an alkyl group; alternatively, an aryl group; or alternatively, an aralkyl group. Generally, the alkyl substituent group(s), the aryl substituent group(s), and/or an aralkyl substituent group(s) can have the same number of carbon atoms of the hydrocarbyl substituent group disclosed herein. In an embodiment, any alkyl substituent of any aspect or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or embodiment calling for a substituent can be phenyl group, a tolyl group, a xylyl group, or a 2,4,6-trimethylphenyl group; alternatively, a phenyl group; alternatively, a tolyl group; alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an embodiment, any hydrocarboxy substituent of any aspect or embodiment calling for a substituent can be an alkoxy group, an aryloxy group, or an aralkoxy group; alternatively, an alkoxy group; alternatively, an aryloxy group, or an aralkoxy group. Generally, the alkoxy substituent group(s), the aroxy substituent group(s), and/or an aralkoxy substituent group(s) can have the same number of carbon atoms of the hydrocarboxy substituent group disclosed herein. In an embodiment, any alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or embodiment calling for a substituent can be phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an embodiment, any aralkoxy substituent of any aspect or embodiment calling for a substituent can be benzoxy group.

The methods described herein can utilize one or more solvents. Non-limiting examples of solvents which can be utilized in aspects and/or embodiments of the present disclosure include without limitation hydrocarbons, halogenated hydrocarbons, ethers, nitriles, amines, phosphines, and phosphites. In some aspects and/or embodiments, a method can call for a polar solvent; or alternatively, a non-polar solvent. Polar solvents which can be utilized include without limitation ethers, nitriles, amines, phosphines, and phosphites, and mixtures thereof; alternatively, ethers; alternatively, nitriles; alternatively, amines; alternatively, phosphines; or alternatively, and phosphites. In some aspects and embodiments, a method can call for a non-polar solvent. Non-polar solvents include without limitation hydrocarbons, halogenated hydrocarbons, or mixtures thereof; alternatively, a hydrocarbon; or alternatively, a halogenated hydrocarbon. In some aspects and embodiments, a method can call for a non-coordinating solvent. Non-coordinating solvents, include without limitation hydrocarbons, halogenated hydrocarbons, or mixtures thereof; alternatively, a hydrocarbon; or alternatively, a halogenated hydrocarbon.

Ethers, nitriles, amines, phosphines, and phosphites are described herein. These ethers, nitriles, amines, phosphines, and phosphites can be utilized without limitation as a solvent or a polar solvent in the various aspects and embodiments described herein.

Hydrocarbons and halogenated hydrocarbons which can be utilized as a general solvent, a non-coordinating solvent, and/or a non-coordinating solvent can include aliphatic hydrocarbons, aromatic hydrocarbons, petroleum distillates, halogenated aliphatic hydrocarbons, halogenated aromatic hydrocarbons, or combinations thereof; or alternatively aliphatic hydrocarbons, aromatic hydrocarbons, halogenated aliphatic hydrocarbons, halogenated aromatic hydrocarbons, and combinations thereof. In some embodiments, hydrocarbons and halogenated hydrocarbons which can be utilized as a general solvent, a non-coordinating solvent, and/or a non-coordinating solvent can include aliphatic hydrocarbons; alternatively, aromatic hydrocarbons; alternatively, halogenated aliphatic hydrocarbons; or alternatively, halogenated aromatic hydrocarbons.

Aliphatic hydrocarbons which can be useful as a general solvent, a non-coordinating solvent, and/or a non-coordinating solvent include $C_4$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. Aliphatic hydrocarbons can be cyclic or acyclic and/or can be linear or branched, unless otherwise specified. Non-limiting examples of suitable acyclic aliphatic hydrocarbon solvents which can be utilized as a general solvent, a non-coordinating solvent, and/or a non-coordinating solvent include iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and any combination thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and any combination thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and any combination thereof; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons). Non-limiting examples, of suitable cyclic aliphatic hydrocarbon solvents which can be utilized as the non-coordinating solvent, include cyclohexane, methyl cyclohexane, and any combination thereof; alternatively cyclohexane; or alternatively, methylcyclohexane.

Aromatic hydrocarbons which can be useful as a general solvent, a non-coordinating solvent, and/or a non-coordinating solvent include $C_6$ to $C_{20}$ aromatic hydrocarbons; or alternatively, $C_6$ to $C_{10}$ aromatic hydrocarbons. Non-limiting examples of suitable aromatic hydrocarbons which can be utilized as a general solvent, a non-coordinating solvent, and/ or a non-coordinating solvent include benzene, toluene, xylene (including ortho-xylene, meta-xylene, para-xylene, or mixtures thereof), and ethylbenzene, or any combination thereof; alternatively, benzene; alternatively, toluene; alternatively, xylene (including ortho-xylene, meta-xylene, para-xylene or mixtures thereof); or alternatively, ethylbenzene.

Halogenated aliphatic hydrocarbons which can be utilized as a general solvent, a non-coordinating solvent, and/or a non-coordinating solvent can include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. The halogenated aliphatic hydrocarbons can be cyclic or acyclic and/or can be linear or branched, unless otherwise specified. Non-limiting examples of suitable halogenated aliphatic hydrocarbons which can be utilized as a general solvent, a non-coordinating solvent, and/or a non-coordinating solvent can include methylene chloride, chloroform, carbon tetrachloride, dichloroethane, trichloroethane, or any combination thereof; alternatively, methylene chloride, chloroform, dichloroethane, trichloroethane, or any combinations thereof; alternatively, methylene chloride; alternatively, chloroform; alternatively, carbon tetrachloride; alternatively, dichloroethane; or alternatively, trichloroethane. Halogenated aromatic hydrocarbons which can be utilized as a general solvent, a non-coordinating solvent, and/or a non-coordinating solvent can include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons which can be utilized as a general solvent, a non-coordinating solvent, and/or a non-coordinating solvent can include chlorobenzene, dichlorobenzene, or any combination thereof; alternatively chlorobenzene; or alternatively, dichlorobenzene.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

Unless indicated otherwise, when a range of any type is disclosed or claimed, for example a range of the number of carbon atoms, molar ratios, temperatures, and the like, it is intended to disclose or claim individually each possible number that such a range could reasonably encompass, including any sub-ranges encompassed therein. For example, when describing a range of the number of carbon atoms, each possible individual integral number and ranges between integral numbers of atoms that the range includes are encompassed therein. Thus, by disclosing a $C_1$ to $C_{10}$ alkyl group or an alkyl group having from 1 to 10 carbon atoms or "up to" 10 carbon atoms, Applicants' intent is to recite that the alkyl group can have 1, 2, 3, 4, 5, 6, 7, 8, 9, or 10 carbon atoms, and these methods of describing such a group are interchangeable. When describing a range of measurements such as molar ratios, every possible number that such a range could reasonably encompass can, for example, refer to values within the range with one significant digit more than is present in the end points of a range. In this example, a molar ratio between 1.03:1 and 1.12:1 includes individually molar ratios of 1.03:1, 1.04:1, 1.05:1, 1.06:1, 1.07:1, 1.08:1, 1.09:1, 1.10:1, 1.11:1, and 1.12:1. Applicants' intent is that these two methods of describing the range are interchangeable. Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. In this aspect, Applicants' disclosure of a $C_1$ to $C_{10}$ alkyl group is intended to literally encompass a $C_1$ to $C_6$ alkyl, a $C_4$ to $C_8$ alkyl, a $C_2$ to $C_7$ alkyl, a combination of a $C_1$ to $C_3$ and a $C_5$ to $C_7$ alkyl, and so forth. When describing a range in which the end points of the range have different numbers of significant digits, for example, a molar ratio from 1:1 to 1.2:1, every possible number that such a range could reasonably encompass can, for example, refer to values within the range with one significant digit more than is present in the end point of a range having the greatest number of significant digits, in this case 1.2:1. In this example, a molar ratio from 1:1 to 1.2:1 includes individually molar ratios of 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, and 1.20, all relative to 1, and any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

For any particular compound disclosed herein, the general structure presented is also intended to encompass all conformational isomers and stereoisomers that can arise from a particular set of substituents, unless indicated otherwise. Thus, the general structure encompasses all structural isomer (e.g., a reference to a propyl group includes n-propyl and iso-propyl, or e.g., a reference to diazole include 1,2-diazole and 1,3-diazole), enantiomers, diastereomers, and other optical isomers whether in enantiomeric or racemic forms, as well as mixtures of stereoisomers, as the context permits or requires, unless specifically indicated otherwise. For any particular formula that is presented, any general formula presented also encompasses all conformational isomers, regioisomers, and stereoisomers that can arise from a particular set of substituents. Moreover and unless otherwise specified, the disclosure of a general compound or structure that can encompass more than one regioisomer is intended to encompass all possible regioisomers within such a general disclosure. For example, by the disclosure of L can be selected from diazepine, a diazepine, or diazepines, it is intended to reflect that L can be selected from 1,2-diazepine, 1,3-diazepine, or 1,4-diazepine.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims.

The data and descriptions provided in the following examples are given to show particular aspects and embodiments of the compounds, catalyst systems, and olefin oligomerization and/or olefin polymerization methods disclosed, and to demonstrate a number of the practices and advantages thereof. The examples are given as a more detailed demonstration of some of the aspects and embodiments described herein and are not intended to limit the disclosure or claims in any manner.

EXAMPLES

In the following examples, unless otherwise specified, the syntheses and preparations described herein were carried out under an inert atmosphere such as nitrogen and/or argon. All coordinating solvents were purchased from Sigma-Aldrich as anhydrous grade solvent and were stored over freshly activated 5 Å molecular sieves prior to use. Unless otherwise specified, reagents were obtained from commercial sources. All glassware was dried in an oven at 100° C. for 4 hr and brought into an inert atmosphere glove box (dry box) while warm.

$CrCl_3 \cdot 6H_2O$. Commercial samples of chromium(III) chloride hexahydrate $CrCl_3 \cdot 6H_2O$ were purchased from Aldrich, catalog number 23,072-3, and obtained as a green crystalline solid. $CrCl_3 \cdot 6H_2O$ is also written as, and generally considered to contain primarily, $[CrCl_2(H_2O)_4]Cl \cdot 2; H_2O$. Karl-Fischer titration of 0.1 grams of the green compound in 9.0 grams of THF indicated a water content of 4244 ppm water versus a predicted water content of 4459 ppm water in the sample.

$CrCl_3(THF)_2(H_2O)$. This compound was purchased from Sigma-Aldrich as the chromium(III) chloride tetrahydrofuran complex (1:3), $CrCl_3(THF)_3$. However, elemental analysis, IR spectroscopy, and Karl-Fischer titration showed that the commercial material sold as the anhydrous $CrCl_3(THF)_3$ was actually the monohydrate complex, $CrCl_3(THF)_2(H_2O)$. Elemental analysis; found (calculated): % C, 30.09 (29.97); % H, 5.64 (5.66); % Cl, 34.42 (33.18). Karl-Fischer titration of 0.1 grams of the purple compound in 9.0 grams of THF indicated a water content of 438 ppm water versus a predicted content of 618 ppm water. The IR spectrum of $CrCl_3(THF)_2(H_2O)$ (KBr window) is provided in FIG. 1.

Activated 5 Å molecular sieves. Samples of 5 Å molecular sieves were purchased from Aldrich as $1/16^{th}$ inch pellets and activated by heating in a vacuum oven at 200° C. overnight.

Anhydrous THF. Anhydrous tetrahydrofuran was purchased from Aldrich and stored over activated 5 Å molecular sieves. The THF was analyzed by Karl-Fischer titration and typically a water content of less than 15 ppm water was measured.

KBr Pellet Preparation. IR samples were prepared in a dry box by adding 5 mg material to 500 mg anhydrous KBr followed by extensive grinding by mortar and pestle. A 10-mm KBr pellet was then formed by placing 100 mg of sample in a Spectra-Tech® Econo-Press Kit. The pellets were then transferred to the IR via an airtight receptacle and the IR sample space was maintained under a nitrogen purge. A background IR spectrum using a pure KBr pellet was collected prior to collecting the sample spectrum.

Example 1

Substantially Anhydrous $CrCl_3(THF)_3$ Prepared from $CrCl_3(THF)_2(H_2O)$

Comparative Method

Substantially anhydrous $CrCl_3(THF)_3$ was prepared from the hydrate from $CrCl_3(THF)_2(H_2O)$, using $Me_3SiCl$ as the drying agent, as follows. A 500 mL round bottom flask was charged with a stir bar, 50 g of $CrCl_3(THF)_2(H_2O)$, 200 mL of anhydrous THF, and 50 mL of trimethylchlorosilane (Me$_3$SiCl). This mixture was stirred under an inert atmosphere (in the dry box) for 4 days. The resulting purple solid was collected by filtration using a glass frit, washed with 100 mL of THF followed by 100 mL of pentane, and dried under vacuum. Yield, 47.5 g CrCl$_3$(THF)$_3$. Elemental analysis, IR spectra, and Karl-Fischer titration confirmed that the material was substantially anhydrous CrCl$_3$(THF)$_3$. Elemental analysis; found (calculated): % C, 38.17 (38.47); % H, 6.52 (6.46); % Cl, 28.66 (28.39). Karl-Fisher titration of 0.1 grams of the purple solid in 9.0 grams of THF indicated a water content of 17 ppm water versus a predicted content of 0 ppm water.

Example 2

Substantially Anhydrous CrCl$_3$(THF)$_3$ Prepared from CrCl$_3$(THF)$_2$(H$_2$O)

Figure 2:
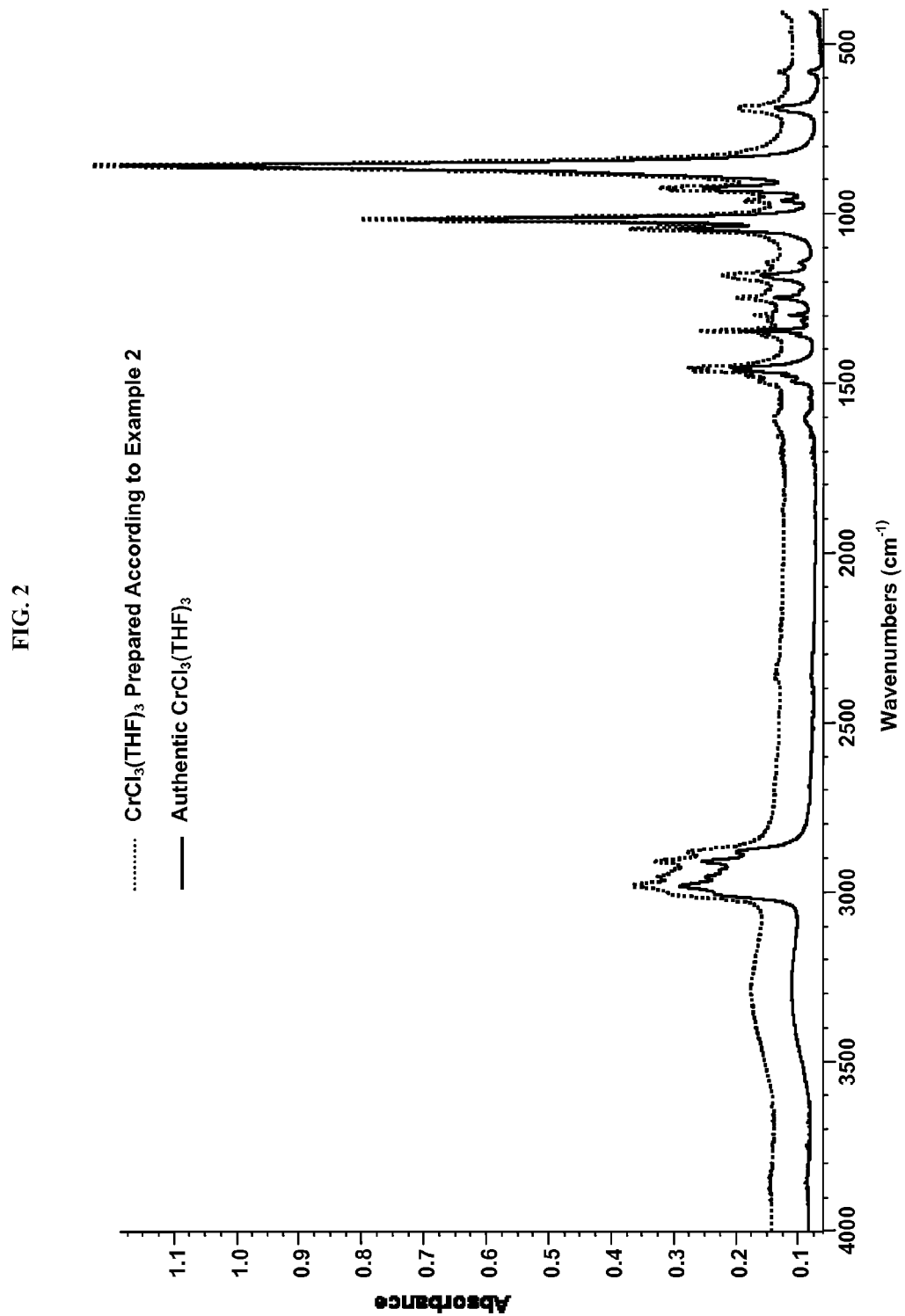
FIG. 2 provides an overlay of the infrared spectrum of $CrCl_3(THF)_3$ produced by contacting $CrCl_3(THF)_2(H_2O)$, THF, and 5 Å molecular sieves, and the infrared spectrum of an authentic sample of $CrCl_3(THF)_3$. Each infrared sample was analyzed as an admixture with KBr pressed into a 10 mm pellet.

Substantially anhydrous CrCl$_3$(THF)$_3$ was prepared from the hydrate from CrCl$_3$(THF)$_2$(H$_2$O), using molecular sieves as the drying agent, as follows. A 20 mL glass vial was charged with 0.5 g of CrCl$_3$(THF)$_2$(H$_2$O), 10 g of anhydrous THF, and 0.7 g of activated 5 Å molecular sieves. This mixture was stirred for 3 days, over which time a purple solution, purple solid, and crushed molecular sieves formed. This mixture was filtered through a 0.25 micron syringe filter disk, and the purple solution was cooled to −10° C., producing 0.25 g of purple crystals of substantially anhydrous CrCl$_3$(THF)$_3$. Formation of substantially a CrCl$_3$(THF)$_3$ was confirmed by IR spectroscopy (KBr window), by comparing this sample with an authentic sample of substantially anhydrous CrCl$_3$(THF)$_3$, FIG. 2.

Example 3

Substantially Anhydrous CrCl$_3$(THF)$_3$ Prepared from CrCl$_3$.6H$_2$O

Substantially anhydrous CrCl$_3$(THF)$_3$ was prepared from CrCl$_3$.6H$_2$O (also written [Cr(H$_2$O)$_4$Cl$_2$]Cl.2; H$_2$O), as follows. A 250 mL round bottom flask was charged with 10.0 g [Cr(H$_2$O)$_4$Cl$_2$]Cl.2H$_2$O, 100 mL of anhydrous THF, and 25.0 g of activated 5 Å molecular sieves. The mixture was stirred for 3 days, over which time its color turned from green to purple. The mixture then was filtered through a glass frit, the filtrate was concentrated to about one-quarter of its original volume, and the concentrated filtrate was layered with approximately an equal volume of pentanes. The purple solid that resulted from this procedure was collected by filtration and dried under vacuum. Karl-Fischer titration confirmed that the purple solid was the mono-hydrate CrCl$_3$(THF)$_2$(H$_2$O). Thus, Karl-Fischer titration of 0.1 grams of the purple solid in 9.0 grams of THF indicated a water content of 538 ppm water, versus a predicted content of 618 ppm water for the compound CrCl$_3$(THF)$_2$(H$_2$O).

It is noted that 10 g of [Cr(H$_2$O)$_4$Cl$_2$]Cl.2H$_2$O used in this example contains at least 4.06 g of H$_2$O, assuming no additional water is absorbed by the solid. Further, 25.0 g of activated 5 Å molecular sieves will hold a theoretical maximum of 21.7% of its weight as water (5.43 g). Accordingly, the reaction required more molecular sieves that the theoretical equivalent amount to drive the dehydration to completion.

Example 4

Substantially anhydrous CrCl$_3$(THF)$_3$ Prepared from CrCl$_3$.6H$_2$O

Substantially anhydrous CrCl$_3$(THF)$_3$ was prepared from the hydrate from CrCl$_3$.6H$_2$O, using molecular sieves as the drying agent, as follows. A 20 mL glass vial was charged with 1.00 g of CrCl$_3$.6H$_2$O, 20 g of anhydrous THF, and 5.0 g of activated 5 Å molecular sieves. This mixture was stirred for 18 hours, over which time a purple solution, purple solid, and crushed molecular sieves formed. This mixture was filtered through a 0.25 micron syringe filter disk, and the purple solution was cooled to −10° C., producing 0.2 g of purple crystals of substantially anhydrous CrCl$_3$(THF)$_3$. The remaining purple solid and molecular sieves were washed three times with 10 mL aliquots of anhydrous THF. The aliquots were combined and the resultant mixture and aliquots were filtered through a 0.25 micron syringe filter disk, and the purple solution was cooled to −10° C., producing 0.3 g of purple crystals of substantially anhydrous CrCl$_3$(THF)$_3$. The overall yield was 36% (0.5 g collected product/1.4 g theoretical yield x 100%). Elemental analysis and Karl-Fischer titration confirmed that the material was substantially anhydrous CrCl$_3$(THF)$_3$. Elemental analysis; found (calculated): % C, 37.69 (38.47); % H, 6.52 (6.46); % Cl, 28.25 (28.39). Karl-Fisher titration of 0.1 grams of the purple solid in 9.0 grams of THF indicated a water content of 29 ppm water versus a predicted content of 0 ppm water.

I claim:

1. A process for preparing a chromium(III) halide complex, comprising:
   contacting 1) a chromium(III) halide hydrate, 2) a water absorption agent, and 3) a coordinating compound, L, to form a solution comprising a chromium(III) halide complex having the formula CrX$_3$.mL and the coordinating compound, where X is a halide, and m is the number of moles of L per mole of chromium and is a number from 1 to 10.

2. The process of claim 1, wherein the chromium(III) halide complex is isolated and the isolated chromium(III) halide complex has a water content of less than or equal to 100 ppm by weight of the isolated chromium(III) halide complex.

3. The process of claim 1, wherein the chromium(III) halide complex is isolated by
   a) filtering the solution;
   b) any one of
      i) concentrating the filtered chromium(III) halide complex solution,
      ii) cooling the filtered chromium(III) halide complex solution,
      iii) contacting the filtered chromium(III) halide complex solution with a non-coordinating solvent, or
      iv) any combination thereof; and
   c) filtering the result of step b) to provide the chromium(III) halide complex.

4. The process of claim 1, wherein the chromium(III) halide hydrate has the formula CrX$_3$(L$^1$)$_q$.nH$_2$O, wherein X is a halide, L$^1$ is a coordinating ligand, q is the number of coordinating ligands and is a number ranging from 0 to 10, n is the number of moles of H$_2$O per mole of chromium, and n is a number from 0.25 to 10.

5. The process of claim 1, wherein the chromium(III) halide hydrate has the formula CrX$_3$.H$_2$O, wherein X is a 6. The process of claim 1, wherein the chromium(III) halide hydrate is selected from $CrF_3 \cdot 4H_2O$, $CrCl_3 \cdot 6H_2O$, $CrBr_3 \cdot 6H_2O$, $CrI_3 \cdot 9H_2O$, or any combination thereof.

7. The process of claim 1, wherein the coordinating compound is a $C_2$-$C_{20}$ acyclic ether, a $C_4$-$C_{20}$ cyclic ether, a $C_2$-$C_{20}$ acyclic thioether, a $C_4$-$C_{20}$ cyclic thioether, a $C_2$-$C_{20}$ aliphatic nitrile, a $C_6$-$C_{20}$ aromatic nitrile, a $C_1$-$C_{20}$ acyclic amine, a $C_4$-$C_{20}$ cyclic amine, or any combination thereof.

8. The process of claim 1, wherein the coordinating compound is a substituted or an unsubstituted cyclic ether.

9. The process of claim 1, wherein the coordinating compound is tetrahydrofuran.

10. The process of claim 1, wherein the water absorption agent is an alumina, a silica gel, a silica-alumina, gypsum, montmorillonite, a molecular sieve, a zeolite, or any combination thereof.

11. The process of claim 1, wherein the water absorption agent is a 3 Å molecular sieve, a 4 Å molecular sieve, a 5 Å molecular sieve, a 10× molecular sieve, a 13× molecular sieve, or any combination thereof.

12. A continuous process for preparing a chromium(III) halide complex, comprising:
flowing a mixture comprising 1) a chromium(III) halide hydrate and 2) a coordinating compound, L, through a bed comprising a solid water absorption agent to form a solution comprising a chromium chromium(III) halide complex having the formula $CrX_3 \cdot mL$ and the coordinating compound, where X is a halide, m is the number of moles of L per mole of chromium, and is a number from 1 to 10.

13. The process of claim 12, wherein the chromium(III) halide hydrate to water absorption agent weight hourly space velocity ranges from 0.1 to 10.

14. The process of claim 12, wherein the chromium(III) halide hydrate has the formula $CrX_3(L^1)_q \cdot nH_2O$, wherein X is a halide, $L^1$ is a coordinating ligand, q is the number of coordinating ligands and is a number ranging from 0 to 10; the halide, n is the number of moles of $H_2O$ per mole of chromium, and n is a number from 0.25 to 10.

solid water absorption agent is a 3 Å molecular sieve, a 4 Å molecular sieve, a 5 Å molecular sieve, a 10× molecular sieve, a 13× molecular sieve, or any combination thereof; the coordinating solvent is a substituted or an unsubstituted cyclic ether; the chromium(III) halide complex is isolated and the isolated chromium(III) halide complex has a water content of less than or equal to 100 ppm by weight of the isolated chromium(III) halide complex.

15. A process for preparing $CrCl_3(THF)_3$, comprising:
contacting 1) a chromium chloride hydrate, 2) tetrahydrofuran, and 3) a 3 Å, 4 Å, 5 Å, 10×, or 13× molecular sieve to form a solution comprising $CrCl_3(THF)_3$ and tetrahydrofuran.

16. The process of claim 15, wherein the $CrCl_3(THF)_3$ is isolated and the isolated $CrCl_3(THF)_3$ has a water content of less than or equal to 100 ppm by weight of the isolated chromium(III) halide complex.

17. The process of claim 15, wherein the $CrCl_3(THF)_3$ is isolated by
a) filtering the solution;
b) any one of
  i) concentrating the filtered $CrCl_3(THF)_3$ solution,
  ii) cooling the filtered $CrCl_3(THF)_3$ solution,
  iii) contacting the filtered $CrCl_3(THF)_3$ solution with a non-coordinating solvent, or
  iv) any combination thereof;
c) filtering the result of step b) to provide a solid $CrCl_3(THF)_3$ and the isolated solid $CrCl_3(THF)_3$ has a water content of less than or equal to 100 ppm by weight of the isolated solid $CrCl_3(THF)_3$.

18. The process of claim 15, wherein the chromium(III) chloride hydrate is $CrCl_3 \cdot 6H_2O$.

19. The process of claim 15, wherein the contacting step occurs by flowing a solution comprising 1) $CrCl_3 \cdot 6H_2O$ and 2) tetrahydrofuran through or over a fixed bed of the molecular sieves.

20. The process of claim 15, wherein $CrCl_3(THF)_3$ is formed at a temperature ranging from 5° C. to about 100° C.

* * * * *